United States Patent
Osborne et al.

(10) Patent No.: US 12,365,882 B2
(45) Date of Patent: Jul. 22, 2025

(54) P450-BM3 VARIANTS WITH IMPROVED ACTIVITY

(71) Applicant: Codexis, Inc., Redwood City, CA (US)

(72) Inventors: Robert Osborne, Raleigh, NC (US); Vesna Mitchell, Santa Clara, CA (US); Khin Yu Naing Htwe, Daly City, CA (US); Xiyun Zhang, Fremont, CA (US); Erika M. Milczek, New York, NY (US); Jeffrey C. Moore, Westfield, NJ (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 18/476,753

(22) Filed: Sep. 28, 2023

(65) Prior Publication Data

US 2024/0026313 A1  Jan. 25, 2024

Related U.S. Application Data

(60) Continuation of application No. 17/672,542, filed on Feb. 15, 2022, now Pat. No. 11,807,874, which is a continuation of application No. 15/931,310, filed on May 13, 2020, now Pat. No. 11,279,917, which is a continuation of application No. 16/131,252, filed on Sep. 14, 2018, now Pat. No. 10,689,627, which is a continuation of application No. 15/619,176, filed on Jun. 9, 2017, now Pat. No. 10,100,289, which is a division of application No. 14/794,249, filed on Jul. 8, 2015, now Pat. No. 9,708,587.

(60) Provisional application No. 62/022,442, filed on Jul. 9, 2014.

(51) Int. Cl.
| | | |
|---|---|---|
| *C12N 9/02* | (2006.01) | |
| *C07K 14/80* | (2006.01) | |
| *C12N 1/21* | (2006.01) | |
| *C12N 15/53* | (2006.01) | |
| *C12P 13/00* | (2006.01) | |

(52) U.S. Cl.
CPC ............ *C12N 9/0071* (2013.01); *C07K 14/80* (2013.01); *C12N 9/0042* (2013.01); *C12P 13/001* (2013.01); *C12Y 114/14001* (2013.01); *C12Y 106/02004* (2013.01)

(58) Field of Classification Search
None
See application file for complete search history.

(56) References Cited

U.S. PATENT DOCUMENTS

| | | |
|---|---|---|
| 5,538,867 A | 7/1996 | Durliat et al. |
| 5,605,793 A | 2/1997 | Stemmer |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |

(Continued)

FOREIGN PATENT DOCUMENTS

| | | |
|---|---|---|
| WO | 95/22625 A1 | 8/1995 |
| WO | 95/33836 A1 | 12/1995 |

(Continued)

OTHER PUBLICATIONS

Altschul, S., et al., "Basic local alignment search tool," J. Mol. Biol., 215: 403-410 (1990).

(Continued)

*Primary Examiner* — David Steadman
(74) *Attorney, Agent, or Firm* — FisherBroyles, LLP; Adam K. Whiting

(57) ABSTRACT

The present invention provides improved P450-BM3 variants with improved activity. In some embodiments, the P450-BM3 variants exhibit improved activity over a wide range of substrates.

13 Claims, 3 Drawing Sheets
Specification includes a Sequence Listing.

(56) References Cited

U.S. PATENT DOCUMENTS

| | | |
|---|---|---|
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,524,664 B2 | 4/2009 | Arnold et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 9,683,220 B2 | 6/2017 | Osborne et al. |
| 9,708,587 B2 | 7/2017 | Osborne et al. |
| 10,100,289 B2 | 10/2018 | Osborne et al. |
| 10,113,153 B2 | 10/2018 | Osborne et al. |
| 10,450,550 B2 | 10/2019 | Osborne et al. |
| 10,689,627 B2 | 6/2020 | Osborne et al. |
| 10,704,030 B2 | 7/2020 | Osborne et al. |
| 10,982,197 B2 | 4/2021 | Osborne et al. |
| 11,279,917 B2 | 3/2022 | Osborne et al. |
| 11,591,578 B2 * | 2/2023 | Osborne ............... C12N 15/63 |
| 11,807,874 B2 * | 11/2023 | Osborne ............... C12P 13/001 |
| 2008/0220990 A1 | 9/2008 | Fox |
| 2008/0268517 A1 | 10/2008 | Arnold et al. |
| 2009/0124515 A1 * | 5/2009 | Arnold .................... C12P 19/02 |
| | | 435/189 |
| 2009/0312196 A1 | 12/2009 | Colbeck et al. |
| 2010/0240106 A1 | 9/2010 | Wong et al. |
| 2011/0244537 A1 | 10/2011 | Arnold et al. |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 2000/42651 A1 | 7/2000 |
| WO | 2001/75767 A2 | 10/2001 |
| WO | 2005/017105 A2 | 2/2005 |
| WO | 2009/152336 A1 | 12/2009 |
| WO | 2014/070673 A1 | 5/2014 |

OTHER PUBLICATIONS

Altschul, S.F., et al., "Gapped BLAST and PSI-BLAST: a new generation of protein database search programs," Nucleic Acids Res., 25(17):3389-3402 (1997).

Beaucage, S.L., et al., "Deoxynucleoside phosphoamidites—A new class of key intermediates for deoxypolynucleotide synthesis," Tetrahedron Letters, 22(20):1859-62 (1981).

Black, M.E., et al., "Creation of drug-specific herpes simplex virus type 1 thymidine kinase mutants for gene therapy," Proc Natl Acad Sci USA, 93:3525-3529 (1996).

Botstein, D., et al., "Strategies and applications of in vitro mutagenesis," Science, 229(4719):1193-1201 [1985].

Caldwell, R.C., et al., "Mutagenic PCR," PCR Methods Appl., 3:S136-S140 (1994).

Capdevila, J.H, et al., "The Highly Stereoselective Oxidation of Polyunsaturated Fatty Acids by Cytochrome P450BM-3," J. Biol. Chem., 271:22663-226671 [1996].

Carter, P., "Site-directed mutagenesis," Biochem. J., 237:1-7 (1986).

Christians, F.C., et al., "Directed evolution of thymidine kinase for AZT phosphorylation using DNA family shuffling," Nat. Biotechnol., 17:259-264 (1999).

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15 (5):436-438 (1997).

Dale, S.J., et al., "Oligonucleotide-directed random mutagenesis using the phosphorothioate method," Methods Mol. Biol., 57:369-74 (1996).

Damsten, M.C., et al., "Application of drug metabolising mutants of cytochrome P450 BM3 (CYP102A1) as biocatalysts for the generation of reactive metabolites," Chem. Biol. Interact., 171:96-107 [2008].

De Boer, H.A., et al., "The tac promoter: A functional hybrid derived from the trp and lac promoters," Proc. Natl Acad. Sci. USA, 80: 21-25 (1983).

Di Nardo, G., et al., "Optimization of the Bacterial Cytochrome P450 BM3 System for the Production of Human Drug Metabolites," Int. J. Mol. Sci., 13(12):15901-15924 [2012].

Guo, Z., et al., "3'-End-Forming Signals of Yeast mRNA," Mol. Cell. Biol., 15(11):5983-5990 [1995].

Henikoff, S., et al., "Amino acid substitution matrices from protein blocks," Proc. Natl. Acad. Sci., 89: 10915-10919 (1992).

Kramer, B., et al., "Different base/base mismatches are corrected with different efficiencies by the methyl-directed DNA mismatch-repair system of E. coli," Cell, 38(3):879-887, 1984.

Ling, M., et al., "Approaches to DNA Mutagenesis:An Overview," Anal. Biochem., 254:157-78 (1997).

Matthes, H.W.D., et al., "Simultaneous rapid chemical synthesis of over one hundred oligonucleotides on a microscale," EMBO J., 3(4):801-05 (1984).

Minshull, J., et al., "Protein evolution by molecular breeding," Curr. Op. Chem. Biol., 3(3):284-290 (1999).

Munro, A.W., et al., "Probing electron transfer in flavocytochrome P-450 BM3 and its component domains," Eur. J. Biochem., 239:403-409 [1996].

(56) References Cited

OTHER PUBLICATIONS

Narhi, L.O., et al., "Characterization of a catalytically self-sufficient 119,000-dalton cytochrome P-450 monooxygenase induced by barbiturates in Bacillus megaterium," J. Biol. Chem., 261(18):7160-7169 [1986].

Needleman, S., et al., "A general method applicable to the search for similarities in the amino acid sequence of two proteins," J. Mol. Biol. 48:443-453 (1970).

Noble, M.A., et al., "Roles of key active-site residues in flavocytochrome P450 BM3," Biochem. J., 339:371-379 [1999].

Otey, C.R., et al., "Preparation of human metabolites of propranolol using laboratory-evolved bacterial cytochromes P450," Biotechnol. Bioeng., 93(3):494-499 [2006].

Pearson, W.R., "Improved tools for biological sequence comparison," Proc. Nat'l. Acad. Sci. USA, 85:2444-2448 (1988).

Romanos, M.A., et al., "Foreign gene expression in yeast: a review," Yeast 8:423-488 [1992].

Sawayama, A.M., et al., "A panel of cytochrome P450 BM3 variants to produce drug metabolites and diversify lead compounds," Chem., 15(43):11723-11729 [2009].

Simonen, M., et al., "Protein Secretion in *bacillus* Species," Microbiological Reviews, 57:109-137 (1993).

Smith, M., "In vitro mutagenesis," Ann. Rev. Genet., 19:423-462 (1985).

Smith, T., et al., "Comparison of Biosequences," Adv. Appl. Math, 2:482-489 (1981).

Stemmer, W., "Dna Shuffling by Random Fragmentation and Reassembly: In vitro Recombination for Molecular Evolution," Proc. Natl. Acad. Sci. USA, 91:10747-10751 (1994).

Stemmer, W.P.C., "Rapid evolution of a protein in vitro by DNA shuffling", Nature, 370:389-391 (1994).

Villa-Komaroff, L., et al., "A bacterial clone synthesizing proinsulin," Proc. Natl Acad. Sci. USA, 75:3727-3731 (1978).

Wells, J.A., et al., "Cassette mutagenesis: an efficient method for generation of multiple mutations at defined sites," Gene, 34:315-323 (1985).

Zhang, J-H., et al., "Directed evolution of a fucosidase from a galactosidase by DNA shuffling and screening ," Proc. Nat. Acad. Sci., U.S.A., 94:4504-4509 (1997).

Zhao, H., et al., "Molecular evolution by staggered extension process (StEP) in vitro recombination," Nat. Biotechnol., 16:258-261 (1998).

Ruettinger, R.T., et al., "Coding nucleotide, 5' regulatory, and deduced amino acid sequences of P-450BM-3, a single peptide cytochrome P-450:NADPH-P-450 reductase from Bacillus megaterium," J. Biol. Chem., 264 (19):10987-10995 [1989].

Wen, L-P., et al., "Cloning of the gene encoding a catalytically self-sufficient cytochrome P-450 fatty acid monooxygenase induced by barbiturates in Bacillus megaterium and its functional expression and regulation in heterologous (*Escherichia coli*) and homologous (Bacillus megaterium) hosts," J. Biol. Chem., 262(14):6676-6682 [1987].

Tsotsou, G.E., et al., "Identification of Mutant Asp251Gly/Gln307His of Cytochrome P450 BM3 for the Generation of Metabolites of Diclofenac, Ibuprofen and Tolbutamide," Chem. Eur. J., 18:3582-3588 [2012].

Sang, H., "Prospects for transgenesis in the chick," Mechanisms of Development, 121:1179-1186 [2004].

Yun, C., et al., "The bacterial P450 BM3: a prototype for a biocatalyst with human P450 activities," Trends in Biotechnology, 25(7):289-298 [2007].

Goswami, R., et al., "Gene Therapy Leaves a Vicious Cycle," Frontiers in Oncology, 9(297):1-25 [2019].

Zhang, M., et al., "Propagated Perturbations from a Peripheral Mutation Show Interactions Supporting WW Domain Thermostability," Structure, 26:1474-1485 [2018].

Singh, K.S., et al., "Protein Engineering Approaches in the Post-Genomic Era," Current Protein and Peptide Science, 18(4):1-11 [2017].

* cited by examiner p-Nitroanisole

Diclofenac

Nifedipine

Propranolol

Verapamil

```
                        SEQUENCE LISTING

Sequence total quantity: 68
SEQ ID NO: 1            moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 1
atgacaataa aggaaatgcc gcagccgaaa acgtttggag aacttaaaaa tttaccgtta  60
ttaaacacag ataaaccggt tcaagctttg atgaaaattg cggatgaatt aggagaaatc 120
tttaaattcg aggcgcctgg tttggtaacg atttacttat caagtcagcg tctaattaaa 180
gaagcatgcg atgaatcacg ctttgataaa aacttaagtc aggcgatgaa atttgcacgt 240
gattttctgg gagacgggtt agcaacaagc tggacgcatg aaataaattg gaaaaagcg  300
cataatatct tacttccaag ctttagtcag caggcaatga aaggctatca tgcgatgatg 360
gtcgatatcg ccgtgcagct tgtttcaaaag tgggagcgtc taaatgcaga tgagcatatt 420
gaagtatcgg aagacatgac acgtttaacg cttgataaca ttggtctttg cggctttaac 480
tatcgcttta acagctttta ccgagatcag cctcatccat ttattataag tatggtccgt 540
gcactggatg aagtaatgaa caagcgtcag cgagcaaatc cagacgaccc agcttatgat 600
gaaaacaagc gccagtgtca agaagatatc aaggtgatga acgacctagt agataaaatt 660
```

```
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat tggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatcaa tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccgaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaaa gggcagaaaa catcgctgac   1800
cgcggtgaag cagatgcaag cgacgacttt gaaggcacat atgaagaatg cgtgaacat   1860
atgtggagtg acgtagcagc ctactttaac ctcgacattg aaacagtgaa agataataaa   1920
tctactcttt cacttcaatt tgtcgacagc gccgcgaata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag   2340
cttgaagcct tgcttgaaaa gcaagcctac aaagaacaag tgctggcaaa acgtttaaca   2400
atgcttgaac tgcttgaaaa aatcccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag acgcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                     3150

SEQ ID NO: 2           moltype = AA  length = 1049
FEATURE                Location/Qualifiers
REGION                 1..1049
                       note = synthetic P450-BM3 variant polypeptide
source                 1..1049
                       mol_type = protein
                       organism = synthetic construct
SEQUENCE: 2
MTIKEMPQPK TFGELKNLPL LNTDKPVQAL MKIADELGEI FKFEAPGLVT IYLSSQRLIK    60
EACDESRFDK NLSQAMKFAR DFLGDGLATS WTHEINWKKA HNILLPSFSQ QAMKGYHAMM   120
VDIAVQLVQK WERLNADEHI EVSEDMTRLT LDTIGLCGFN YRFNSFYRDQ PHPFIISMVR   180
ALDEVMNKRQ RANPDDPAYD ENKRQCQEDI KVMNDLVDKI IADRKARGEQ SDDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVNVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPA TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQDAHFYIC GDGSQMAPAV EATLMKSYAD  1020
VHQVSEADAR LWLQQLEEKG RYAKDVWAG                                    1049

SEQ ID NO: 3           moltype = DNA  length = 3150
FEATURE                Location/Qualifiers
misc_feature           1..3150
                       note = synthetic P450-BM3 variant polynucleotide
source                 1..3150
                       mol_type = other DNA
                       organism = synthetic construct
SEQUENCE: 3
atgacaataa aggaaatgcc gcagccgaaa acgtttggag aacttaaaaa tttaccgtta    60
```

```
ttaaacacag ataaaccggt tcaagctttg atgaaaattg cggatgaatt aggagaaatc  120
tttaaattcg aggcgcctgg tttggtaacg atttacttat caagtcagcg tctaattaaa  180
gaagcatgcg atgaatcacg ctttgataaa aacttaagtc aggcgatgaa atttgcacgt  240
gattttctgg gagacgggtt agcaacaagc tggacgcatg aaccgaattg gaaaaaagcg  300
cataatatct taggcccaag cttttagtcag caggcaatga aacgttatca tgccgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta acagcttta ccgagatcag cctcatccat ttattataag tatggtccgt  540
gcactggatg aagtaatgaa caagcgtcag cgagcaaatc cagacgaccc agcttatgat  600
gaaaacaagc gccagtgtca agaagatatc aaggtgatga acgaccagt agataaaatt  660
attgcagatc gcaaagcaag gggtgaacaa agccatgatt tattaacgca gatgctaaac  720
ggaaaagatc cagaaacggg tgagccgctt gatgacggga acattagcta tcaaattatt  780
acattcttaa ttgcgggaca cgaaacaaca agtggtcttt atcatttgc gctgtatttc  840
ttagtgaaaa atccacatgt attacaaaaa gtagcagaa aagcagcacg agttctagta  900
gatcctgttc caagctacaa acaagtcaaa cagcttaaat atgtcggcat ggtcttaaac  960
gaagcgctgc gcttatggcc aactgctcct gcgttttccc tatatgcaaa agaagatacg 1020
gtgcttggag gagaatatcc tttagaaaaa ggcgacgaag taaatgttct gattcctcag 1080
cttcaccgtg ataaaacaat ttggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact tgaagatca tacaaactac gagctcgata ttaaagaaac tttaacgtta 1320
aaacctgaag gctttgtggt aaaagcaaaa tcgaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccggaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctgg cacgtatcaa 1740
aaagtgcctg ctttatcga tgaaacgctt gccgctaaag gggcagaact gatcgctgac 1800
cgcggtgaag cagatgcaag cgacgacttt gaaggcccgt atgaagaatg gcgtgaactan 1860
atgtggagtg acgtagcagc ctactttaac ctcgacattg aaaacagtga agataataaa 1920
tctactcttt cacttcaatt tgtcgacagc gccgcggata tgccgcttgc gaaaatgcac 1980
ggtgcgtttt caacgaacgt cgtagcagcc aagaacttc aacagccagg cagtgcacga 2040
agcacgcgac atcttgaaat tgaacttcca aagaagctt cttatcaaga aggagatcat 2100
ttaggtgtta ttcctcgcaa ctatgaagga atagtaaacc gtgtaacagc aaggttcggc 2160
ctagatgcac cgcagcaaat ccgtctggaa gcagaagaag aaaaaattag tcatttgcca 2220
ctcgctaaaa cagtatccgt agaagagctt ctgcaatacg tggagcttca agatcctgcg 2280
acgcgcacgc agcttcgcgc aatggctgct aaaacggtct gcccgccgca taagtagag 2340
cttgaagcct tgcttgaaaa gcaagcctac aaagaacaag tgctggcaaa acgtttaaca 2400
atgcttgaac tgcttgaaaa ataccccggc tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggagaag cgtggagcgg atatggagaa 2580
tataaaggaa ttgcgtcgaa ctatcttgcc gagctgcaag aaggagatac gattacgtgc 2640
tttatttcca caccgcagtc agaatttacg ctgccaaaag accctgaaac gccgcttatc 2700
atggtcggac cgggaacagg cgtcgcgccg tttagaggct tgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcataccg ctttttctcg catgccaaat cagccgaaaa catacgttca gcacgtaatg 2940
gaacaagacg gcaagaaatt gattgaactt cttgatcaag gagcgcactt ctatatttgc 3000
ggagacggaa gccaaatggc acctgccgtt gaagcaacgc ttatgaaaag ctatgctgac 3060
gttcaccaag tgagtgaagc agacgctcgc ttatggctgc agcagctaga agaaaaaggc 3120
cgatacgcaa aagacgtgtg ggctgggtaa                                  3150
```

```
SEQ ID NO: 4           moltype = AA   length = 1049
FEATURE                Location/Qualifiers
REGION                 1..1049
                       note = synthetic P450-BM3 variant polypeptide
source                 1..1049
                       mol_type = protein
                       organism = synthetic construct
SEQUENCE: 4
MTIKEMPQPK TFGELKNLPL LNTDKPVQAL MKIADELGEI FKFEAPGLVT IYLSSQRLIK   60
EACDESRFDK NLSQAMKFAR DFLGDGLATS WTHEPNWKKA HNILGPSFSQ QAMKRYHAMM  120
VDIAVQLVQK WERLNADEHI EVSEDMTRLT LDTIGLCGFN YRFNSFYRDQ PHPFIISMVR  180
ALDEVMNKRQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWAGTYQ KVPAFIDETL AAKGAELIAD  600
RGEADASDDF EGPYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDAPQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049
```

```
SEQ ID NO: 5            moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 5
atgacaataa aggaaatgcc gcagccgaaa acgtttggag aacttaaaaa tttaccgtta      60
ttaaacacag ataaaccggt tcaagctttg atgcgtattg cggatgaatt aggagaaatc     120
tttaaattcg aggcgcctgg tttggtaacg atttactat caagtcagcg tctaattaaa      180
gaagcatgcg atgaatcacg ctttgataaa aacttaagtc aggcgatgaa atttgcacgt     240
gatttctgg gagacggggtt agcaacaagc tggacgcatg aaccgaattg gaaaaaagcg     300
cataatatct tacttccaag ctttagtcag caggcaatga aacgttatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagcttta ccgagatcag cctcatccat ttattataag tatggtccgt      540
gcactggatg aagtaatgaa caagcgtcag cgagcaaatc cagacgaccc agcttatgat     600
gaaaacaagc gccagtgtca agaagatatc aaggtgatga cgaccagt agataaaatt       660
attgcagatc gcaaagcaag gggtgaacaa agccatgatt tattaacgca gatgctaaac     720
ggaaaagatc cagaaacggg tgagccgctt gatgacgga acattagcta tcaaatatt      780
acattcttaa ttgcgggaca cgaaacaaca agtggtcttt tatcatttgc gctgtatttc     840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct cgttttccc tatatgcaaa agaagatacg    1020
gtgcttggag gagaatatcc tttacataaa ggcgacgaag taaatgttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctag tacttggtat gatgctaaaa    1260
cactttgact tgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccgaaatc ttccgcgcga aggagctgta ttaattgtaa cggcgtctta taacggtcat     1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat     1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtcgtttt caacgaacgt cgtagcaagc aagaacttc aacagccagg cagtgcacga     2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctgaa gcagaagaag aaaaattagc tcatttgcca    2220
ctcgctaaaa cagtatccgt agaagagctt ctgcaatacg tggagcttca agatcctgca    2280
acgcgcacgc agcttcgcgc aatggctgct aaaacggtct gcccgccgca taaagtagag    2340
cttgaagcct tgcttgaaaa gcaagcctac aaagaacaag tgttagcaaa cgtttaaca    2400
atgcttgaac tgcttgaaaa ataccgcgcg tgtgaaatga aattcagcga atttatcgcc    2460
cttctgccaa gcatacgccc gcgctattac tcgatttctt catcacctcg tgtcgataaa    2520
aaacaagcaa gcatcacggt cagcgttgtc tcaggagaac gtggagcgg atatggaaga    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtggac cgggaacagg cgtcgcgcc tttagagcgt ttgtgcaggc gcgcaaacag     2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttttctcg catgccaaat cagccgaaaa catacgttca gcacgtaatg    2940
gaacaagacg gcagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaggc    3120
cgatacgcaa aagacgtgtg ggctgggtaa                                     3150

SEQ ID NO: 6            moltype = AA  length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 6
MTIKEMPQPK TFGELKNLPL LNTDKPVQAL MRIADELGEI FKFEAPGLVT IYLSSQRLIK      60
EACDESRFDK NLSQAMKFAR DFLGDGLATS WTHEPNWKKA HNILLPSFSQ QAMKRYHAMM    120
VDIAVQLVQK WERLNADEHI EVSEDMTRLT LDTIGLCGFN YRFNSFYRDQ PHPFIISMVR    180
ALDEVMNKRQ RANPDDPAYD ENKRQCQEDI KVMNDLVDKI IADRKARGEQ SHDLLTQMLN    240
GKDPETGEPL DDGNISYQII TFLIAGHETT SGLLSFALYF LVKNPHVLQK VAEEAARVLV    300
DPVPSYKQVK QLKYVGMVLN EALRLWPTAP AFSLYAKEDT VLGGEYPLHK GDEVNVLIPQ    360
LHRDKTIWGD DVEEFRPERF ENPSAIPQHA FKPFGNGQRA CIGQQFALHE ATLVLGMMLK    420
HFDFEDHTNY ELDIKETLTL KPEGFVVKAK SKKIPLGGIP SPSTEQSAKK VRKKAENAHN    480
```

```
TPLLVLYGSN MGTAEGTARD LADIAMSKGF APQVATLDSH AGNLPREGAV LIVTASYNGH    540
PPDNAKQFVD WLDQASADEV KGVRYSVFGC GDKNWATTYQ KVPAFIDETL AAKGAENIAD    600
RGEADASDDF EGTYEEWREH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LDASQQIRLE AEEEKLAHLP LAKTVSVEEL LQYVELQDPA TRTQLRAMAA KTVCPPHKVE    780
LEALLEKQAY KEQVLAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 7                moltype = DNA   length = 3150
FEATURE                     Location/Qualifiers
misc_feature                1..3150
                            note = synthetic P450-BM3 variant polynucleotide
source                      1..3150
                            mol_type = other DNA
                            organism = synthetic construct
SEQUENCE: 7
atgacaataa aggaaatgcc gcagccgaaa acgtttggag aacttaaaaa tttaccgtta     60
ttaaacacag ataaaccggt tcaagctttg atgcgtattg cggatgaatt aggagaaatc    120
tttaaattcg aggcgcctgg tttggtaacg atttacttat caagtcagcg tctaattaaa    180
gaagcatgcg atgaatcacg ctttgataaa aacttaagtc aggcgatgaa atttgcacgt    240
gattttctgg gagacgggtt agcaacaagc tggacgcatg aaccgaattg gaaaaaagcg    300
cataatatct taggcccaag ctttagtcag caggcaatga aaggctatca tgcgatgatg    360
gtcgatatcg ccgtgcagct tgttcaaaag tgggagcgtc taaatgcaga tgagcatatt    420
gaagtatcgc aagacatgac acgtttaacg cttgatacaa ttggtctttg cggctttaac    480
tatcgcttta acagcttta ccgagatcag cctcatccat ttattataag tatggtccgt    540
gcactggatg aagtaatgaa caagcgtcag cgagcaaatc cagacgaccc acgttatgat    600
gaaaacaagc gccagtgtca agaagatatc aaggtgatca cgacctagt agataaaatt    660
attgcagatc gcaaagcaag gggtgaacaa agccatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcagg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaacaat tgggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgtga ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccgaaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctgg cacgtatcaa   1740
aaagtgcctg cttttatcga tgaaacgctt gccgctaaag ggcagaact gatcgctgac   1800
cgcggtgaag cagatgcaag cgacgacttt gaaggcccgt atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcagcc aaagaacttc aacagccagg cagtgcacga   2040
agcacgcgac atcttgaaat tgaacttcca aagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctgaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag   2340
cttgaagcct tgcttgaaaa gcaagcctac aaagaacaag tgtcagcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaattacg ctgccaaatc ccgaaac gccgcttatc   2700
atggtcggac cgggaacagg cgtcgcgccg tttagaggct tgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgt   3000
ggagacggaa gccaaatggc acctaccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                   3150

SEQ ID NO: 8                moltype = AA   length = 1049
FEATURE                     Location/Qualifiers
REGION                      1..1049
                            note = synthetic P450-BM3 variant polypeptide
source                      1..1049
                            mol_type = protein
```

```
                    organism = synthetic construct
SEQUENCE: 8
MTIKEMPQPK TFGELKNLPL LNTDKPVQAL MRIADELGEI FKFEAPGLVT IYLSSQRLIK    60
EACDESRFDK NLSQAMKFAR DFLGDGLATS WTHEPNWKKA HNILGPSFSQ QAMKGYHAMM   120
VDIAVQLVQK WERLNADEHI EVSEDMTRLT LDTIGLCGFN YRFNSFYRDQ PHPFIISMVR   180
ALDEVMNKRQ RANPDDPRYD ENKRQCQEDI KVMNDLVDKI IADRKARGEQ SHDLLTQMLN   240
GKDPETGEPL DDGNISYQII TFLIAGHETT SGLLSFALYF LVKNPHVLQK VAEEAARVLV   300
DPVPSYKQVL QLKYVGMVLN EALRLWPTAP AFSLYAKEDT VLGGEYPLEK GDEVNVLIPQ   360
LHRDKTIWGD DVEEFRPERF ENPSAIPQHA FKPFGNGQRA CIGQQFALHE ATLVLGMMLK   420
HFDFEDHTNY ELVIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWAGTYQ KVPAFIDETL AAKGAELIAD   600
RGEADASDDF EGPYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPA TRTQLRAMAA KTVCPPHKVE   780
LEALLEKQAY KEQVSAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPTV EATLMKSYAD  1020
VHQVSEADAR LWLQQLEEKG RYAKDVWAG                                   1049

SEQ ID NO: 9           moltype = DNA   length = 3150
FEATURE                Location/Qualifiers
misc_feature           1..3150
                       note = synthetic P450-BM3 variant polynucleotide
source                 1..3150
                       mol_type = other DNA
                       organism = synthetic construct
SEQUENCE: 9
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg tttggtaacg atttactat caagtcagcg tctaattaaa   180
gaagcatgcg atgaatcacg ctttgataaa aacttaagtc aggcgatgaa atttgcacgt   240
gattttctgg gagacgggtt agcaacaagc tggacgcaatg aaccgaattg gaaaaaagcg   300
cataatatct tacttccaag ctttagtcag caggcaatga aagcctatca tgccgatgcg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta acagctttta ccgagatcag cctcatccat ttattataag tatggtccgt   540
gcactggatg aagtaatgaa caagcgtcag cgagcaaatc cagacgaccc agcttatgat   600
gaaaacaagc gccagtgtca agaagatatc aaggtgatga acgaccgtag atataaaatt   660
attgcagatc gcaaagcaag gggtgaacaa agccatgatt tattaacgca gatgctaaac   720
ggaaaagatc cagaaacggg tgagccgctt gatgacggga acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaag taaatgttct gattcctcag  1080
cttcaccgtg ataaaacaat tggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact tgaagatca tacaaactac gagctcgata ttaaagaaac tttaacgtta  1320
aaacctgaag gctttgtggt aaaagcaaaa tcgaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa actgggctac tacgtatcaa  1740
aaagtgcctg cttttatcga tgaaacgctt gccgctaaag gggcagaaaa catcgctgac  1800
cgcggtgaag cagatgcaag cgacgacttt gaaggcacat atgaagaatg cgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagatc cttatcaaga aggatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattagc tcatttgcca  2220
ctcgctaaaa cagtatccgt agaagagctt ctgcaatacg tggagcttca agatcctgcg  2280
acgcgcacgc agcttcgcgc aatggctgct aaaacggtct gcccgccgca taagtagag  2340
cttgaagcct tgcttgaaaa gcaagcctac aaagaacaag tgtcagcaaa acgtttaaca  2400
atgcttgaac tgcttgaaaa ataccccggc tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttattcca caccgcagtc agaatttacg cccgaaacc ctgaacgttatc  2700
atggtcggac cgggaacagg cgtcgcgccg tttagaggct tgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg cttttctcg catgccaaat cagccgaaaa catacgttca gcacgtaatg  2940
gaacaagacg gcaagaaatt gattgaactt cttgatcaag gagcgcactt ctatatttgc  3000
```

```
ggagacggaa gccaaatggc acctgccgtt gaagcaacgc ttatgaaaag ctatgctgac 3060
gttcaccaag tgagtgaagc agacgctcgc ttatggctgc agcagctaga agaaaaaggc 3120
cgatacgcaa aagacgtgtg ggctgggtaa                                  3150

SEQ ID NO: 10           moltype = AA   length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 10
MTIKEMPQPK TFGELKNLPL LNTDKPVQAL MKIADELGEI FKFEAPGLVT IYLSSQRLIK    60
EACDESRFDK NLSQAMKFAR DFLGDGLATS WTHEPNWKKA HNILLPSFSQ QAMKGYHAMM   120
VDIAVQLVQK WERLNADEHI EVSEDMTRLT LDTIGLCGFN YRFNSFYRDQ PHPFIISMVR   180
ALDEVMNKRQ RANPDDPAYD ENKRQCQEDI KVMNDLVDKI IADRKARGEQ SHDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVNVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPA TRTQLRAMAA KTVCPPHKVE   780
LEALLEKQAY KEQVSAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                   1049

SEQ ID NO: 11           moltype = DNA   length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 11
atgacaataa aggaaatgcc gcagccgaaa acgtttggag aacttaaaaa tttaccgtta   60
ttaaacacag ataaaccggt tcaagctttg atgcgtattg cggatgaatt aggagaaatc  120
tttaaattcg aggcgcctgg ttttggtaacg atttacttat caagtcagcg tctaattaaa  180
gaagcatgcg atgaatcacg cttttgataaa aacttaagcg aggcgatgaa attgcacgt   240
gattttctgg gagacgggtt agcaacaagc tggacgcatg aaccgaattg gaaaaaagcg  300
cataatatct tacttccaag cttttagtcag caggcaatga aaggctatca tgcgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta acagctttta ccgagatcag cctcatccat ttattataag tatggtccgt  540
gcactggatg aagtaatgaa caagcgtcag cgagcaaatc cagacgaccc acgttatgat  600
gaaaacaagc gccagtgtca agaagatatc aaggtgatga cgaccctagt agataaaatt  660
attgcagatc gcaaagcaag gggtgaacaa agccatgatt tattaacgca gatgctaaac  720
ggaaaagatc cagaaacggg tgagccgctt gatgacggga acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttaaaa tatgtcggcat ggtcttaaac  960
gaagcgctgc gcttatggcc aactgctcct gcgttttccc tatatgcaaa agaagatacg 1020
gtgcttggag agaatatcc tttagaaaaa ggcgacgaag taaatgttct gattcctcag 1080
cttcaccgtg ataaaacaat ttggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttgttat gatgctaaaa 1260
cactttgact tgaagatca tacaaactac gagctcgata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacgg ctgaaggaac ggcgcgtgat 1500
ttagcagata ttgcaatgag caaaggattt gcaccgcagg tcgcaacgct tgattcacac 1560
gccgaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaa actgggctac tacgtatcaa 1740
aaagtgcctg cttttatcga tgaaacgctt gccgctaaag gggcagaaaa catcgctgac 1800
cgcggtgaag cagatgcaag cgacgacttt gaaggcacat atgaagaatg cgtgaacat 1860
atgtggagtg acgtagcagc ctactttaac ctcgacattg aaacagtga gataataaa 1920
tctactcttt cacttcaatt tgtcgacagc gccgcggata tgccgcttgc gaaaatgcac 1980
ggtgcgtttt caacgaacgt cgtagcaagc aagaacttc aacagccagg cagtgcacga 2040
agcacgcgga atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcac cgcagcaaat ccgtctggaa gcagaagaag aaaaattagc tcatttgcca 2220
ctcgctaaaa cagtatccgt agaagagctt ctgcaatacg tggagcttca agatcctgcg 2280
acgcgcacgc agcttcgcgc aatggctgct aaaacggtct gcccgccgca taagtagag 2340
cttgaagcct tgcttgaaaa gcaagcctac aaagaacaag tgctggcaaa acgtttaaca 2400
```

-continued

```
atgcttgaac tgcttgaaaa atacccggcg tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttattcca caccgcagtc agaatttacg ctgccaaaag accctgaaac gccgcttatc  2700
atggtcggac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcatacg cttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctaccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                  3150
```

SEQ ID NO: 12          moltype = AA   length = 1049
FEATURE                Location/Qualifiers
REGION                 1..1049
                       note = synthetic P450-BM3 variant polypeptide
source                 1..1049
                       mol_type = protein
                       organism = synthetic construct
SEQUENCE: 12
MTIKEMPQPK TFGELKNLPL LNTDKPVQAL MRIADELGEI FKFEAPGLVT IYLSSQRLIK   60
EACDESRFDK NLSQAMKFAR DFLGDGLATS WTHEPNWKKA HNILLPSFSQ QAMKGYHAMM  120
VDIAVQLVQK WERLNADEHI EVSEDMTRLT LDTIGLCGFN YRFNSFYRDQ PHPFIISMVR  180
ALDEVMNKRQ RANPDDPRYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDAPQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPTV EATLMKSYAD 1020
VHQVSEADAR LWLQQLEEKG RYAKDVWAG                                  1049

SEQ ID NO: 13          moltype = DNA   length = 3150
FEATURE                Location/Qualifiers
misc_feature           1..3150
                       note = synthetic P450-BM3 variant polynucleotide
source                 1..3150
                       mol_type = other DNA
                       organism = synthetic construct
SEQUENCE: 13

```
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg tttggtaacg atttacttat caagtcagcg tctaattaaa  180
gaagcatgcg atgaatcacg ctttgataaa aacttaagtc aggcgatgaa atttgcacgt  240
gattttctgg gagacgggtt agcaacaagc tggacgcatg aaccgaattg gaaaaaagcg  300
cataatatct taggcccaag cttttagtcag caggcaatga aggctatca tgcgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta cagctttta ccgagatcag cctcatccat ttattataag tatggtccgt  540
gcactggatg aagtaatgaa caagcgtcag gcgaacaatc cagacgaccc agcttatgat  600
gaaaacaagc gccagtgtca agaagatatc aaggtgatga acgacctagt agataaaatt  660
attgcagatc gcaaagcaag gggtgaacaa agccatgatt tattaacgca gatgctaaac  720
ggaaaagatc cagaaacggg tgagccgctt gatgacggga cattagcta tcaaattatt  780
acattcttaa ttgcgggaca cgaaacaaca agtggtcttt atcattgc gctgtatttc  840
ttagtgaaaa atccacatgt attacaaaaa gtagcagaag aagcagcag agttctagta  900
gatcctgttc caagctacaa acaagtcaaa cagcttaaat atgtcggcat ggtcttaaac  960
gaagcgctgc gcttatggcc aactgctcct gcgttttccc tatatgcaaa agaagatacg 1020
gtgcttggag gagaatatcc tttagaaaaa ggcgacgaag taaatgttct gattcctcag 1080
cttcaccgtg ataaaacaat ttggggagac gatgtggagg agttccgtcc agagcgtttt 1140
gaaaatccaa gtgcgattcc gcagcatgcg tttaaaccgt ttggaaacgg tcagcgttgg 1200
tgtatccggtc agcagttcgc tcttcatgaa gcaacgctgg tacttggtat gatgctaaaa 1260
cactttgact tgaagatcca tacaaactac gagctcgata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctg ttgtgctata cggttcaaat atgggaacag ctgaaggaac ggcacgtgat 1500
ttagcagata ttgcaatgag caaaggattt gcaccgcagg tcgcaacgct tgattcacac 1560
gccgaaaatc ttccgcgcga aggagctgta ttaattgtaa cggcgtctta taacggtcat 1620
ccgcctgata cgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag gggcagaaaa catcgctgac 1800
```

```
cgcggtgaag cagatgcaag cgacgacttt gaaggcacat atgaagaatg gcgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcac cgcagcaaat ccgtctggaa cagaagaag aaaaattagc tcatttgcca  2220
ctcgctaaaa cagtatccgt agaagagctt ctgcaatacg tggagcttca agatcctgcg  2280
acgcgcacgc agcttcgcgc aatggctgct aaaacggtc gcccgccgca taaagtagag  2340
cttgaagcct tgcttgaaaa gcaagcctac aaagaacaag tgttagcaaa acgtttaaca  2400
atgcttgaac tgcttgaaaa ataccccggcg tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaaa aggagatac gattacgtgc  2640
tttatttcca caccgcagtc agaatttacg ctgccaaaag accctgaaac gccgcttatc  2700
atggtcggac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg cttttcctcg catgccaaat cagccgaaaa catacgttca gcacgtaatg  2940
gaacaagacg gcaagaaatt gattgaactt ctgatcaag gagcgcactt ctatatttgc  3000
ggagacggaa gccaaatggc acctaccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                    3150

SEQ ID NO: 14           moltype = AA  length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 14
MTIKEMPQPK TFGELKNLPL LNTDKPVQAL MKIADELGEI FKFEAPGLVT IYLSSQRLIK   60
EACDESRFDK NLSQAMKFAR DFLGDGLATS WTHEPNWKKA HNILGPSFSQ QAMKGYHAMM  120
VDIAVQLVQK WERLNADEHI EVSEDMTRLT LDTIGLCGFN YRFNSFYRDQ PHPFIISMVR  180
ALDEVMNKRQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAT  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDAPQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPTV EATLMKSYAD  1020
VHQVSEADAR LWLQQLEEKG RYAKDVWAG                                    1049

SEQ ID NO: 15           moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 15
atgacaataa aggaaatgcc gcagccgaaa acgtttggag aacttaaaaa tttaccgtta   60
ttaaacacag ataaaccggt tcaagctttg atgcgtattg cggatgaatt aggagaaatc  120
tttaaattcg aggcgcctgg tttggtaacg atttactat caagtcagcg tctaattaaa  180
gaagcatgcg atgaatcacg ctttgataaa aacttaagtc aggcgatgaa atttgcacgt  240
gattttctgg gagacgggtt agcaacaagc tggacgcaca aatcaaattg gaaaaaagcg  300
cataatatct tacttccaag ctttagtcag caggcaatga aacgttatca tgccgatgatg  360
gtcgatatcg ccgtgcagct tgttcaaaag tgggagcgtc taaatgcaga tgagcatatt  420
gaagtatcgg aagacatgac acgtttaacg cttgataaa ttggtctttg cggctttaac  480
tatcgcttta caagctttta ccgagatcag cctcatccat ttattataag tatggtccgt  540
gcactggatg aagtaatgaa caagcgtcag cgagcaaatc cagacgaccc agcttatgat  600
gaaaacaagc gccagtgtca agaagatatc aaggtgatga cgacctagt agataaaatt  660
attgcagatc gcaaagcaag gggtgaacaa gccatgatt tattaacgca gatgctaaac  720
ggaaaagatc cagaaacggg tgagccgctt gatgacggaa acattagcta tcaaattatt  780
acattcttaa ttgcgggaca cgaaacaaca agtggtcttt tatcatttgc gctgtatttc  840
ttagtgaaaa atccacatgt attacaaaaa gtagcagcag agttctagta  900
gatcctgttc caagctacaa acaagtcaaa cagcttaaat atgtcggcat ggtcttaaac  960
gaagcgctgc gcttatggcc aactgctcct gcgtttttcc tatatgcaaa agaagatacg 1020
gtgcttggag agaatatcc tttagaaaaa ggcgacgaag taaatgttct gattcctcag 1080
cttcaccgtg ataaaacaat tgggagac gatgtggagg agttccgtcc agagcgtttt 1140
gaaaatccaa gtgcgattcc gcagcatgcg tttaaaccgt ttggaaacgg tcagcgtgcg 1200
```

-continued

```
tgtatcggtc agcagttcgc tcttcatgaa gcaacgctgg tacttggtat gatgctaaaa 1260
cactttgact ttgaagatca tacaaactac gagctcgata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacgc tgaaggaacg ggcgcgtgat 1500
ttagcagata ttgcaatgag caaaggattt gcaccgcagg tcgcaacgct tgattcacac 1560
gccggaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag ggggcagaaa catcgctgac 1800
cgcggtgaag cagatgcaag cgacgacttt gaaggcacat atgaagaatg gcgtgaacat 1860
atgtggagtg acgtagcagc ctactttaac ctcgacattg aaacagtgaa agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctggaa gcagaagaag aaaaattagc tcatttgcca 2220
ctcgctaaaa cagtatccgt agaagagctt ctgcaatacg tggagcttca agatcctgcg 2280
acgcgcacgc agcttcgcgc aatggctgct aaaacggtct gcccgccgca taaagtagag 2340
cttgaagcct tgcttgaaaa gcaagcctac aagaacaag tgctggcaaa acgtttaaca 2400
atgcttgaac tgcttgaaaa ataccccggcg tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggagaag cgtggagcgg atatggagaa 2580
tataaaggaa ttgcgtcgaa ctatcttgcc gagctgcaag aaggagatac gattacgtgc 2640
tttatttcca caccgcagtc agaatttacg ctgccaaaag accctgaaac gccgcttatc 2700
atggtcggac cgggaacagg cgtcgcgccc tttagaggct ttgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcataccg ctttttctcg catgccaaat cagccgaaaa catacgttca gcacgtaatg 2940
gaacaagacg gcaagaaatt gattgaactt cttgatcaag gagcgcactt ctatatttcg 3000
ggagacggaa gccaaatggc aacctgccgtt gaagcaacgc ttatgaaaag ctatgctgac 3060
gttcaccaag tgagtgaagc agacgctcgc ttatggctgc agcagctaga gaaaaaggc 3120
cgatacgcaa aagacgtgtg ggctgggtaa 3150
```

```
SEQ ID NO: 16              moltype = AA   length = 1049
FEATURE                    Location/Qualifiers
REGION                     1..1049
                           note = synthetic P450-BM3 variant polypeptide
source                     1..1049
                           mol_type = protein
                           organism = synthetic construct
SEQUENCE: 16
MTIKEMPQPK TFGELKNLPL LNTDKPVQAL MRIADELGEI FKFEAPGLVT IYLSSQRLIK  60
EACDESRFDK NLSQAMKFAR DFLGDGLATS WTHEINWKKA HNILLPSFSQ QAMKRYHAMM  120
VDIAVQLVQK WERLNADEHI EVSEDMTRLT LDTIGLCGFN YRFNSFYRDQ PHPFIISMVR  180
ALDEVMNKRQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                   1049
```

```
SEQ ID NO: 17              moltype = DNA   length = 3150
FEATURE                    Location/Qualifiers
misc_feature               1..3150
                           note = synthetic P450-BM3 variant polynucleotide
source                     1..3150
                           mol_type = other DNA
                           organism = synthetic construct
SEQUENCE: 17
atgacaataa aggaaatgcc gcagccgaaa acgtttggag aacttaaaaa tttaccgtta  60
ttaaacacag ataaaccggt tcaagctttg atgaaaattg cggatgaatt aggagaaatc  120
tttaaattcg aggcgcctgg ttttggtaac atttacttat caagtcagcg tctaattaaa  180
gaagcatgcg atgaatcacg ctttgataaa aacttaagtc aggcgatgaa atttgcacgt  240
gattttctgg gagacggtt agcaacaagc tggacagaaa ttaactggaa gaaaagcg  300
cataatatct taggcccaag ctttagtcag caggcaatga aaggctatca tgcgatgatg  360
gtcgatatcg ccgtgcagct tgttcaaaag tgggagcgtc taaatgcaga tgagcatatt  420
gaagtatcg aagacatgac acgtttaacg cttgatacaa ttggtctttg cggctttaac  480
tatcgcttta acagctttta ccgagatcag cctcatccat ttattataag tatggtccgt  540
gcactggatg aagtaatgaa caagcgtcag cgagcaaatc cagacgaccc acgttatgat  600
```

```
gaaaacaagc gccagtgtca agaagatatc aaggtgatga acgacctagt agataaaatt  660
attgcagatc gcaaagcaag gggtgaacaa agcgatgatt tattaacgca gatgctaaac  720
ggaaaagatc cagaaacggg tgagccgctt gatgacggga acattagcta tcaaattatt  780
acattcttaa ttgcgggaca cgaaacaaca agtggtcttt atcatttgc gctgtatttc   840
ttagtgaaaa atccacatgt attacaaaaa gtagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgttttccc tatatgcaaa agaagatacg  1020
gtgcttggag gagaatatcc tttagaaaaa ggcgacgaag taaatgttct gattcctcag  1080
cttcaccgtg ataaaacaat tggggagac gatgtggagg agttccgtcc agagcgtttt   1140
gaaaatccaa gtgcgattcc gcagcatgcg tttaaccgt ttggaaacgg tcagcgtgcg   1200
tgtatcggtc agcagttcgc tcttcatgaa gcaacgctgg tacttggtat gatgctaaaa  1260
cactttgact tgaagatca tacaaactac gagctcgata ttaaagaaac tttaacgtta   1320
aaacctgaag gctttgtggt aaaagtcaaa tcgaaaaaa ttccgcttgg cggtattcct   1380
tcacctagca ctgaacagtc tgctaaaaaa gtacgcaaaa agctcataat                1440
acgccgctgc ttgtgctata cggttcaaat atgggaacag ctgaaggaac ggcgcgtgat  1500
ttagcagata ttgcaatgag caaggattt gcaccgcagg tcgcaacgct tgattcacac   1560
gccggaaatc ttccgcgcga aggagctgta ttaattgtaa cggcgtctta taacggtcat   1620
ccgcctgata acgcaaaggg cttttgtcga tggttagaca aagcgtctgc tgatgaagta  1680
aaaggcgttc gctactccgt atttggatgc ggcgataaaa actgggctgg cacgtatcaa  1740
aaagtgcctg cttttatcga tgaaacgctt gccgctaaag gggcagaact gatcgctgac  1800
cgcggtgaag cagatgcaag cgacgacttt gaaggcacat atgaagaatg gcgtgaacat  1860
atgtggagtg acgtagcagc ctactttaac ctcgacattg aaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aagaagctt cttatcaaga aggagatcat  2100
ttaggtgtta ttcctcgcaa ctatgaagga atagtaaacc gtgtaacagc aaggttcggc  2160
ctagatgcac cgcagcaaat ccgtctgaaa gcagaagaag aaaaattagc tcatttgcca  2220
ctcgctaaaa cagtatccgt agaagagctt ctgcaatacg tggagcttca agatcctgcg  2280
acgcgcacga gcttcgcgc aatggctgct aaaacggtct gcccgccgca taagtagag   2340
cttgaagcct tgcttgaaaa gcaagcctac aaagaacaag tgttagcaaa acgtttaaca  2400
atgcttgaac tgcttgaaaa ataccccggcg tgtgaaatga aattcagcga atttatcgcc  2460
cttctgccaa gcatacgccc cgcgctattac tcgatttctt catcacctcg tgtcgatgaa  2520
aaacaagcaa gcatcacggt cagcgttgtc tcaggaaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag acctgaaac gccgcttatc  2700
atggtcggac cgggaacagg cgtcgcgccc tttagaggct ttgtgcaggc gcgcaaacag  2760
ctaaagaac aaggacagtc acttggagaa gcacatttat acttcggctg ccgttccacct  2820
catgaagact atctgtatca agaagagctt gaaaacgccc aaagcgaagg catcattacg  2880
cttcataccg ctttttctcg catgccaaat cagccgaaaa cagtcgcacg tgatg       2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                  3150
```

SEQ ID NO: 18            moltype = AA  length = 1049
FEATURE                  Location/Qualifiers
REGION                   1..1049
                         note = synthetic P450-BM3 variant polypeptide
source                   1..1049
                         mol_type = protein
                         organism = synthetic construct SEQUENCE: 18
MTIKEMPQPK TFGELKNLPL LNTDKPVQAL MKIADELGEI FKFEAPGLVT IYLSSQRLIK   60
EACDESRFDK NLSQAMKFAR DFLGDGLATS WTHEPNWKKA HNILGPSFSQ QAMKGYHAMM  120
VDIAVQLVQK WERLNADEHI EVSEDMTRLT LDTIGLCGFN YRFNSFYRDQ PHPFIISMVR  180
ALDEVMNKRQ RANPDDPRYD ENKRQCQEDI KVMNDLVDKI IADRKARGEQ SDDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKGFVD WLDQASADEV KGVRYSVFGC GDKNWAGTYQ KVPAFIDETL AAKGAELIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDAPQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDAKKLIEL LDQGAHFYIC GDGSQMAPAV EATLMKSYAD 1020
VHQVSEADAR LWLQQLEEKG RYAKDVWAG                                   1049

SEQ ID NO: 19            moltype = DNA  length = 3150
FEATURE                  Location/Qualifiers
misc_feature             1..3150
                         note = synthetic P450-BM3 variant polynucleotide
source                   1..3150
                         mol_type = other DNA
                         organism = synthetic construct

SEQUENCE: 19

-continued

```
atgacaataa aggaaatgcc gcagccgaaa acgtttggag aacttaaaaa tttaccgtta    60
ttaaacacag ataaaccggt tcaagctttg atgcgtattg cggatgaatt aggagaaatc   120
tttaaattcg aggcgcctgg tttggtaacg atttacttat caagtcagcg tctaattaaa   180
gaagcatgcg atgaatcacg ctttgataaa aacttaagtc aggcgatgaa atttgcacgt   240
gattttctgg gagacggggtt agcaacaagc tggacgatga aaccgaattg gaaaaaagcg   300
cataatatct taggcccaag cttttagtcag caggcaatga aaggctatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta acagctttta ccgagatcag cctcatccat ttattataag tatggtccgt   540
gcactggatg aagtaatgaa caagcgtcag cgagcaaatc cagacgaccc agcttatgat   600
gaaaacaagc gccagtgtca agaagatatc aaggtgatga acgaccagt agataaaatt   660
attgcagatc gcaaagcaag gggtgaacaa agccatgatt tattaacgca gatgctaaac   720
ggaaaagatc cagaaacggg tgagccgctt gatgacggga acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaaa taaatgttct gattcctcag  1080
cttcaccgtg ataaaacaat ttggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact ttgaagatca tacaaactac gagctcgtga ttaaagaaac tttaacgtta  1320
aaacctgaag gctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa actgggctgg cacgtatcaa  1740
aaagtgcctg cttttatcga tgaaacgctt gccgctaaag gggcagaact gatcgctgac  1800
cgcggtgaag cagatgcaag cgacgacttt gaaggcacat atgaagaatg gcgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgttt caacgaacgt cgtagcaagc aaagaacttc aacagccagg cagtgcacga  2040
agcacgcgac atcttgaaat tgaacttcca aagaagcttc ttatcaaga aggagatcat  2100
ttaggtgtta ttcctcgcaa ctatgaagga atagtaaacc gtgtaacagc aaggttcggc  2160
ctagatgcat cacagcaaat ccgtctgaaa gcagaagaag aaaaattagc tcatttgcca  2220
ctcgctaaaa cagtatccgt agaagagctt ctgcaatacg tggagcttca agatcctgcg  2280
acgcgcacgc agcttcgcgc aatgcgctgct aaaacgtct gccgccgca taagtagag  2340
cttgaagcct tgcttgaaaa gcaagcctac catgaacaag tgttagcaaa acgtttaaca  2400
atgcttgaac tgcttgaaaa ataccgcgcg tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag gtgggagcgg atatgggaaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcgac cgggaacagg cgtcgcgccg tttagaggct tgtgcaggc gcgcaaacag  2760
ctaaaagaac aaggacagtc acttggagaa gcacattat acttcggctg ccgttcacct  2820
catgaagact atctgtatca agaagagctt gaaaacgccc aaagcgaagg catcattacg  2880
cttcataccg cttttctcg catgccaaat cagccgaaaa catacgttca gcacgtaatg  2940
gaacaagacg gcaagaaatt gattgaactt cttgatcaag agcgcactt ctatatttgc  3000
ggagacggaa gccaaatggc acctgccgtt gaagcaacgc ttatgaaaag ctatgctgac  3060
gttcaccaag tgagtgaagc agacgctcga ttatggctgc agcagctaga agaaaaaggc  3120
cgatacgcaa aagactgtgt ggctgggtaa                                    3150
```

```
SEQ ID NO: 20           moltype = AA   length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 20
MTIKEMPQPK TFGELKNLPL LNTDKPVQAL MRIADELGEI FKFEAPGLVT IYLSSQRLIK    60
EACDESRFDK NLSQAMKFAR DFLGDGDLATS WTHEPNWKKA HNILGPSFSQ QAMKGYHAMM  120
VDIAVQLVQK WERLNADEHI EVSEDMTRLT LDTIGLCGFN YRFNSFYRDQ PHPFIISMVR  180
ALDEVMNKRQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK DEVNVLIPQ   360
LHRDKTIWGD DVEEFRPERF ENPSAIPQHA FKPFGNGQRA CIGQQFALHE ATLVLGMMLK  420
HFDFEDHTNY ELVIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWAGTYQ KVPAFIDETL AAKGAELIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSEELL LQYVELQDPA TRTQLRAMAA KTVCPPHKVE  780
LEALLEKQAY HEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQERTFYIC GDGSQMAPAV EATLMKSYAD 1020
```

VHQVSEADAR LWLQQLEEKG RYAKDVWAG                                          1049

```
SEQ ID NO: 21          moltype = DNA   length = 3150
FEATURE                Location/Qualifiers
misc_feature           1..3150
                       note = synthetic P450-BM3 variant polynucleotide
source                 1..3150
                       mol_type = other DNA
                       organism = synthetic construct
SEQUENCE: 21
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg tttggtaacg atttacttat caagtcagcg tctaattaaa  180
gaagcatgcg atgaatcacg ctttgataaa aacttaagtc aggcgatgaa atttgcacgt  240
gattttctgg gagacgggtt agcaacaagc tggacgcatg aaataaattg gaaaaaagcg  300
cataatatct tagcgccaag ctttagtcac caggcaatga taggctatca tgcgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta acagctttta ccgagatcag cctcatccat ttattataag tatggtccgt  540
gcactggatg aagtaatgaa caagcgtcag cgagcaaatc cagacgaccc agcttatgat  600
gaaaacaagc gccagtgtca agaagatatc aaggtgatga cgactatgt agataaaatt  660
attgcagatc gcaaagcaag gggtgaacaa agcgatgatt attaacgaca gatgctaaac  720
ggaaaagatc cagaaacggg tgagccgctt gatgacggga acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttataa atgtcggcat ggtcttaaac  960
gaagcgctgc gcttatggcc aactgctcct gcgttttccc tatatgcaaa agaagatacg 1020
gtgcttggag gagaatggcc tttacgtaaa ggcgacgaag taaatgttct gattcctcag 1080
cttcaccgtg ataaaacaat ttggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact tgaagatcat acaaactac gagctcgata ttaaagaaac tttaacgtta 1320
aaacctgaag gctttgtggt aaaagcaaaa tcgaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccgaaatc ttccgcgcga aggagctgta ttaattgtaa cggcgtctta taacggtcat 1620
ccgcctgata acgcaaagaa ctttgtcgac tggttagacc aagcgtctgc tgatgaagta 1680
aaaggcgttc gctactccgt atttggatgc ggcgataaa actgggctac tacgtatcaa 1740
aaagtgcctg ctttatcga tgaaacgctt gccgctaaag gggcagaaaa catcgctgac 1800
cgcggtgaag cagatgcaag cgacgacttt gaaggccgtt atgaagaatg gcgtgaacat 1860
atgtggagtg acgtagcagc ctactttaac ctcgacattg aaaacagtga agataataaa 1920
tctactcttt cacttcaatt tgtcgacagc gccgcggata tgccgcttgc gaaaatgcat 1980
ggtgcgttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtgtgaa gcagaagaag aaaaattgac tcatttgcca 2220
ctcgctaaaa cagtatccgt agaagagctt ctgcaatacg tggagcttca agatcctgcg 2280
acgcgcacgc agcttcgcgc aatggctgct aaaacggtct gcccgccgca taagtagag 2340
cttgaagcct tgcttgaaaa gcaagcctac aaagaacaag tgctggcaaa cgtttaaca 2400
atgcttgaac tgcttgaaaa atacccggcg tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggaaag cgtggagcgg atatggagaa 2580
tataaaggaa ttgcgtcgaa ctatcttgcc gagctgcaag aaggagatac gattacgtgc 2640
tttatttcca caccgcagtc agaatttacg ctgccaaaag accctgaaac gccgcttatc 2700
atggtcggac cgggaacagg cgtcgcgccg tttagaggct ttgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcatacg ctttttctcg catgccaaat cagccgaaaa catacgttca gcacgtaatg 2940
gaacaagacg gcaagaaatt gattgaactt cttgatcaag gagcgcactt ctatatttgc 3000
ggagacggaa gccaaatggc acctgccgtt gaagcaacgc ttatgaaaag ctatgctgac 3060
gttcaccaag tgagtgaagc agacgctcgc ttatggctgc agcagctaga agaaaaaggc 3120
cgatacgcaa aagacgtgtg ggctgggtaa                                  3150

SEQ ID NO: 22          moltype = AA   length = 1049
FEATURE                Location/Qualifiers
REGION                 1..1049
                       note = synthetic P450-BM3 variant polypeptide
source                 1..1049
                       mol_type = protein
                       organism = synthetic construct
SEQUENCE: 22
MTIKEMPQPK TFGELKNLPL LNTDKPVQAL MKIADELGEI FKFEAPGLVT IYLSSQRLIK   60
EACDESRFDK NLSQAMKFAR DFLGDGLATS WTHEINWKKA HNILAPSFSH QAMIGYHAMM  120
VDIAVQLVQK WERLNADEHI EVSEDMTRLT LDTIGLCGFN YRFNSFYRDQ PHPFIISMVR  180
ALDEVMNKRQ RANPDDPAYD ENKRQCQEDI KVMNDYVDKI IADRKARGEQ SDDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEWPLRK GDEVNVLIPQ  360
LHRDKTIWGD DVEEFRPERF ENPSAIPQHA FKPFGNGQRA CIGQQFALHE ATLVLGMMLK  420
```

```
HFDFEDHTNY ELDIKETLTL KPEGFVVKAK SKKIPLGGIP SPSTEQSAKK VRKKAENAHN    480
TPLLVLYGSN MGTAEGTARD LADIAMSKGF APQVATLDSH AGNLPREGAV LIVTASYNGH    540
PPDNAKNFVD WLDQASADEV KGVRYSVFGC GDKNWATTYQ KVPAFIDETL AAKGAENIAD    600
RGEADASDDF EGRYEEWREH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LDASQQIRVE AEEEKLAHLP LAKTVSVEEL LQYVELQDPA TRTQLRAMAA KTVCPPHKVE    780
LEALLEKQAY KEQVLAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 23           moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct SEQUENCE: 23
atgacaataa aggaaatgcc gcagccgaaa acgtttggag aacttaaaaa tttaccgtta     60
ttaaacacag ataaaccggt tcaagctttg atgaaaattg cggatgaatt ggagaaatc    120
tttaaattcg aggcgcctgg tttggtaacg atttacttat caagtcagcg tctaattaaa   180
gaagcatgcg atgaatcacg ctttgataaa aacttaagtc aggcgatgaa atttgcacgt   240
gattttctgg agacgggtt agcaacaagc tggacgcatg aaataaattg gaaaaaagcg   300
cataatatct tagcgccaag cttttagtcac caggcaatga aaggctatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta acagctttta ccgagatcag cctcatccat ttattataag tatggtccgt   540
gcactggatg aagtaatgaa caagcgtcag cgagcaaatc cagacgaccc agcttatgat   600
gaaaacaagc gccagtgtca agaagatatc aaggtgatga acgacctagt agataaaatt   660
attgcagatc gcaaagcaag gggtgaacaa agcgatgatt tattaacgca gatgctaaac   720
ggaaaagatc cagaaacggg tgagccgctt gatgacggga cattagcta tcaaattatt   780
acattcttaa ttgcggggaca cgaaacaaca agtggtctt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag agaatggcc tttagagaaa ggcgacgaag taaatgttct gattcctcag  1080
cttcaccgtg ataaaacaat ttgggggac gatgtggaag agttccgtcc agaagcgttt  1140
gaaaatccaa gtgcgattcc gcagcatgcg tttaaaccgt ttggaaacg tcagcgtgcg  1200
tgtatcggtc agcagttcgc tcttcatgaa gcaacgctgg tacttggtat gatgctaaaa  1260
cactttgact ttgaagatca tacaaactac gagctcgata ttaagaaac tttaacgtta  1320
aaacctgaag gcttttgtgt aaaagcaaa tcgaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa actgggctca tacgtatcaa  1740
aaagtgcctg cttttatcga tgaaacgctt gccgctaaag gggcagaaaa catcgctgac  1800
cgcggtgaag cagatgcaag cgacgacttt gaaggccgtt atgaagaatg gcgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcgc  2160
ctagatgcat cacagcaaat ccgtgtgaaa gcagaagaag aaaaattagc tcatttgcca  2220
ctcgctaaaa cagtatccgt agaagagctt ctgcaatacg tggagcttca agatcctgcg  2280
acgcgcacgc agcttcgcgc aatggctgct aaaacggtct gcccgccgca taagtagag  2340
cttgaagcct tgcttgaaaa gcaagcctac aaagaacaag tgctggcaaa acgtttaaca  2400
atgcttgaac tgcttgaaaa ataccccggc tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cggaacagg cgtcgcgccg tttagaggct tgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg cttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                   3150

SEQ ID NO: 24           moltype = AA  length = 1049
FEATURE                 Location/Qualifiers
REGION                  1..1049
                        note = synthetic P450-BM3 variant polypeptide
source                  1..1049
```

```
                        mol_type  =  protein
                        organism  =  synthetic construct
SEQUENCE: 24
MTIKEMPQPK  TFGELKNLPL  LNTDKPVQAL  MKIADELGEI  FKFEAPGLVT  IYLSSQRLIK   60
EACDESRFDK  NLSQAMKFAR  DFLGDGLATS  WTHEINWKKA  HNILAPSFSH  QAMKGYHAMM  120
VDIAVQLVQK  WERLNADEHI  EVSEDMTRLT  LDTIGLCGFN  YRFNSFYRDQ  PHPFIISMVR  180
ALDEVMNKRQ  RANPDDPAYD  ENKRQCQEDI  KVMNDLVDKI  IADRKARGEQ  SDDLLTQMLN  240
GKDPETGEPL  DDGNISYQII  TFLIAGHETT  SGLLSFALYF  LVKNPHVLQK  VAEEAARVLV  300
DPVPSYKQVK  QLKYVGMVLN  EALRLWPTAP  AFSLYAKEDT  VLGGEWPLEK  GDEVNVLIPQ  360
LHRDKTIWGD  DVEEFRPERF  ENPSAIPQHA  FKPFGNGQRA  CIGQQFALHE  ATLVLGMMLK  420
HFDFEDHTNY  ELDIKETLTL  KPEGFVVKAK  SKKIPLGGIP  SPSTEQSAKK  VRKKAENAHN  480
TPLLVLYGSN  MGTAEGTARD  LADIAMSKGF  APQVATLDSH  AGNLPREGAV  LIVTASYNGH  540
PPDNAKQFVD  WLDQASADEV  KGVRYSVFGC  GDKNWAHTYQ  KVPAFIDETL  AAKGAENIAD  600
RGEADASDDF  EGRYEEWREH  MWSDVAAYFN  LDIENSEDNK  STLSLQFVDS  AADMPLAKMH  660
GAFSTNVVAS  KELQQPGSAR  STRHLEIELP  KEASYQEGDH  LGVIPRNYEG  IVNRVTARFG  720
LDASQQIRVE  AEEEKLAHLP  LAKTVSVEEL  LQYVELQDPA  TRTQLRAMAA  KTVCPPHKVE  780
LEALLEKQAY  KEQVLAKRLT  MLELLEKYPA  CEMKFSEFIA  LLPSIRPRYY  SISSSPRVDE  840
KQASITVSVV  SGEAWSGYGE  YKGIASNYLA  ELQEGDTITC  FISTPQSEFT  LPKDPETPLI  900
MVGPGTGVAP  FRGFVQARKQ  LKEQGQSLGE  AHLYFGCRSP  HEDYLYQEEL  ENAQSEGIIT  960
LHTAFSRMPN  QPKTYVQHVM  EQDGKKLIEL  LDQGAHFYIC  GDGSQMAPAV  EATLMKSYAD 1020
VHQVSEADAR  LWLQQLEEKG  RYAKDVWAG                                     1049

SEQ ID NO: 25             moltype = DNA   length = 3150
FEATURE                   Location/Qualifiers
misc_feature              1..3150
                          note = synthetic P450-BM3 variant polynucleotide
source                    1..3150
                          mol_type = other DNA
                          organism = synthetic construct
SEQUENCE: 25
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg tttggtaacg atttactttat caagtcagcg tctaattaaa  180
gaagcatgcg atgaatcacg ctttgataaa aacttaagtc aggcagatga atttgcacgt  240
gattttctgg gagacgggtt agcaacaagc tggacgcatg aaataaattg gaaaaaagcg  300
cataatatct tacttccaag cttttagtcag caggcaatga aaggctatca tgcgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggcttttac  480
tatcgcttta acagctttta ccgagatcag cctcatccat ttattcagag tatggtccgt  540
gcactggatg aagtaatgaa caagcgtcag cgagccaaatc cagacgaccc agcttatgat  600
gaaaacaagc gccagtgtca agaagatatc aaggtgatga acgaccagt acagaaaatt  660
attgcagatc gcaaagcaag gggtgaacaa agcgatgatt tattaacgca gatgctaaac  720
ggaaaagatc cagaaacggg tgagccgctt gatgacgggaa acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgtttttcc tatatgcaaa agaagatacg 1020
gtgcttggag gagaatatca attatccaaa ggcgacgaag taaatgttct gattcctcag 1080
cttcaccgtg ataaaacaat ttgggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact tgaagatcaa tacaaactac gagctcgata ttaaagaaac tttaacgtta 1320
aaacctgaag gctttgtggt aaaagcaaaa tcgaaaaaaa ttccgcttgg ctttattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccgaaatc ttccgcgcga aggagctgta ttaattgtaa cggcgtctta taacggtcat 1620
ccgcctgata acgcaaagca atttgtccgt tggttagacc aagcgtctgc tgatgaagta 1680
aaaggcgttc gctactccgt atttggatgc ggcgataaa actgggctcc gacgtatcaa 1740
aaagtgcctg cttttatcga tgaaacgctt gccgctaaag gggcagaaaa catcgctctg 1800
cgcggtgaag cagatgcaag cgacgacttt gaaggcacat atgaagaatg gcgtgaacat 1860
atgtggagtg acgtagcagc ctactttaac ctcgacattg aaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctgaa gcagaagaag aaaaattagc tcatttgcca 2220
ctcgctaaaa cagtatccgt agaagagctt ctgcaatacg tggagcttca agatcctgcg 2280
acgcgcacgc agcttcgcgc aatggctgct aaaacggtct gcccgccgca taagtagag 2340
cttgaagcct tgcttgaaaa gcaagcctac aaagaacaag tgctggcaaa cgtttaaca 2400
atgcttgaac tgcttgaaaa ataccegcg tgtgaaatga attcagcga tttatcgcc 2460
cttctgccaa gcatacgcc gcgctattac tcgatttctt catcacctcg tgtcgatgaa 2520
aaacaagcaa gcatcacggt cagcgttgtc tcaggagaag cgtggagcgg atatggagaa 2580
tataaagga ttgcgtcgaa ctatcttgcc gagctgcaag aaggagatac gattacgtgc 2640
tttatttcca caccgcagtc agaattacg ctgccaaaag accctgaaac gccgcttatc 2700
atggtcggac cgggaacagg cgtcgcgccg tttagaggct tgtgcaggc gcgcaaacag 2760
ctaaaagaac aaggacagtc acttggagaa gcacatttat acttcggctg ccgttcacct 2820
catgaagact atctgtatca agaagagctt gaaacgcccc aaagcgaagg catcattacg 2880
cttcataccg ctttttctcg catgccaaat cagccgaaaa catacgttca gcacgtaatg 2940
```

-continued

```
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                   3150
```

| SEQ ID NO: 26 | moltype = AA   length = 1049 |
|---|---|
| FEATURE | Location/Qualifiers |
| REGION | 1..1049 |
| | note = synthetic P450-BM3 variant polypeptide |
| source | 1..1049 |
| | mol_type = protein |
| | organism = synthetic construct |

SEQUENCE: 26

```
MTIKEMPQPK TFGELKNLPL LNTDKPVQAL MKIADELGEI FKFEAPGLVT IYLSSQRLIK   60
EACDESRFDK NLSQAMKFAR DFLGDGLATS WTHEINWKKA HNILLPSFSQ QAMKGYHAMM  120
VDIAVQLVQK WERLNADEHI EVSEDMTRLT LDTIGLCGFN YRFNSFYRDQ PHPFIQSMVR  180
ALDEVMNKRQ RANPDDPAYD ENKRQCQEDI KVMNDLVQKI IADRKARGEQ SDDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYQLSK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGFIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVR WLDQASADEV KGVRYSVFGC GDKNWAPTYQ KVPAFIDETL AAKGAENIAR  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049
```

| SEQ ID NO: 27 | moltype = DNA   length = 3150 |
|---|---|
| FEATURE | Location/Qualifiers |
| misc_feature | 1..3150 |
| | note = synthetic P450-BM3 variant polynucleotide |
| source | 1..3150 |
| | mol_type = other DNA |
| | organism = synthetic construct |

SEQUENCE: 27

```
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg tttggtaacg atttacttat caagtcagcg tctaattaaa  180
gaagcatgcg atgaatcacg ctttgataaa aacttaagtc aggcgatgaa atttgcacgt  240
gatttttctg gagacgggtt agcaacaagc tggacgcatg aaataaaatg gaaaaaagcg  300
cataatatct tacttccaag cttttagtcag caggcaatga aaggctatca tgcgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta acagctttta ccgagatcag cctcatccat ttattataag tatggtccgt  540
gcactggatg aagtaatgaa caagcgtcag cgagcaaatc cagacgaccc agcttatgat  600
gaaaacaagc gccagtgtca agaagatatc aaggtgatga acgacctagt agataaaatt  660
attgcagatc gcaaagcaag gggtgaacaa agcgatgatt tattaacgca gatgctaaac  720
ggaaaagatc cagaaacggg tgagccgctt gatgacggga acattagcta tcaaattatt  780
acattcttaa ttgcgggaca cgaaacaaca agtggtcttt tatcatttgc gctgtatttc  840
ttagtgaaaa atccacacgt attacaaaaa gtagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgttttccc tatatgcaaa agaagatacg 1020
gtgcttggag gagaatatca attatccaaa ggcgacgaag taaatgttct gattcctcag 1080
cttcaccgtg ataaaacaat tggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact tgaagatcca tacaaactac gagctcgata ttaaagaaac tttaacgtta 1320
aaacctgaag gctttgtggt aaaagcaaaa tcgaaaaaaa ttccgcttgg ctttattcct 1380
tcacctagca ctgaacagtc tgctaaaaaa gtacgcaaaa agcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccgaaaatc ttccgcgcga aggagctgta ttaattgtaa cggcgtctta taacggtcat 1620
ccgcctgata acgcaaagca atttgtccgt tggttagaac aagcgctgc tgatgaagta 1680
aaaggcgttc gctactccgt atttggatgc ggcgatcaaa actgggctac tacgtatcaa 1740
aaagtgcctg cttttatcga tgaaacgctt gccgctaaag ggcagaaaaa catcgctgac 1800
cgcggtgaag cagatgcaag cgacgacttt gaaggcacat atgaagaatg cgtgaacat 1860
atgtggagtg acgtagcagc ctactttaac ctcgacattg aaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctgaa gcagaagaag aaaaattagc tcatttgcca 2220
ctcgctaaaa cagtatccgt agaagagctt ctgcaatacg tggagcttca agatcctgcg 2280
acgcgcacga agcttcgcgc aatggctgct accacgtgtc gcccgccgca taagtagag 2340
```

-continued

```
cttgaagcct tgcttgaaaa gcaagcctac aaagaacaag tgctggcaaa acgtttaaca 2400
atgcttgaac tgcttgaaaa ataccccggcg tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggagaag cgtggagcgg atatggaaga 2580
tataaaggaa ttgcgtcgaa ctatcttgcc gagctgcaaa aaggagatac gattacgtac 2640
tttatttcca caccgcagtc agaatttacg ctgccaaaag accctgaaac gccgcttatc 2700
atggtcggac cgggaacagg cgtcgcgccg tttagaggct ttgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcataccg cttttttctcg catgccaaat cagccgaaaa catacgttca gcacgtaatg 2940
gaacaagacg gcaagaaatt gattgaactt cttgatcaag gagcgcactt ctatatttgc 3000
ggagacggaa gccaaatggc acctgccgtt gaagcaacgc ttatgaaaag ctatgctgac 3060
gttcaccaag tgagtaata  tgacgctcgc ttatggctgc agcagctaga agaaaaaggc 3120
cgatacgcaa aagacgtgtg ggctgggtaa                                  3150
```

SEQ ID NO: 28        moltype = AA    length = 1049
FEATURE              Location/Qualifiers
REGION               1..1049
                     note = synthetic P450-BM3 variant polypeptide
source               1..1049
                     mol_type = protein
                     organism = synthetic construct
SEQUENCE: 28

```
MTIKEMPQPK TFGELKNLPL LNTDKPVQAL MKIADELGEI FKFEAPGLVT IYLSSQRLIK  60
EACDESRFDK NLSQAMKFAR DFLGDGLATS WTHEINWKKA HNILLPSFSQ QAMKGYHAMM 120
VDIAVQLVQK WERLNADEHI EVSEDMTRLT LDTIGLCGFN YRFNSFYRDQ PHPFIISMVR 180
ALDEVMNKRQ RANPDDPAYD ENKRQCQEDI KVMNDLVDKI IADRKARGEQ SDDLLTQMLN 240
GKDPETGEPL DDGNISYQII TFLIAGHETT SGLLSFALYF LVKNPHVLQK VAEEAARVLV 300
DPVPSYKQVK QLKYVGMVLN EALRLWPTAP AFSLYAKEDT VLGGEYQLSK GDEVNVLIPQ 360
LHRDKTIWGD DVEEFRPERF ENPSAIPQHA FKPFGNGQRA CIGQQFALHE ATLVLGMMLK 420
HFDFEDHTNY ELDIKETLTL KPEGFVVKAK SKKIPLGFIP SPSTEQSAKK VRKKAENAHN 480
TPLLVLYGSN MGTAEGTARD LADIAMSKGF APQVATLDSH AGNLPREGAV LIVTASYNGH 540
PPDNAKQFVR WLDQASADEV KGVRYSVFGC GDKNWATTYQ KVPAFIDETL AAKGAENIAD 600
RGEADASDDF EGTYEEWREH MWSDVAAYFN LDIENSEDNK STLSLQFVDS AADMPLAKMH 660
GAFSTNVVAS KELQQPGSAR STRHLEIELP KEASYQEGDH LGVIPRNYEG IVNRVTARFG 720
LDASQQIRLE AEEEKLAHLP LAKTVSVEEL LQYVELQDPA TRTQLRAMAA TTVCPPHKVE 780
LEALLEKQAY KEQVLAKRLT MLELLEKYPA CEMKFSEFIA LLPSIRPRYY SISSSPRVDE 840
KQASITVSVV SGEAWSGYGE YKGIASNYLA ELQEGDTITC FISTPQSEFT LPKDPETPLI 900
MVGPGTGVAP FRGFVQARKQ LKEQGQSLGE AHLYFGCRSP HEDYLYQEEL ENAQSEGIIT 960
LHTAFSRMPN QPKTYVQHVM EQDGKKLIEL LDQGAHFYIC GDGSQMAPAV EATLMKSYAD 1020
VHQVSEYDAR LWLQQLEEKG RYAKDVWAG                                   1049
```

SEQ ID NO: 29        moltype = DNA    length = 3150
FEATURE              Location/Qualifiers
misc_feature         1..3150
                     note = synthetic P450-BM3 variant polynucleotide
source               1..3150
                     mol_type = other DNA
                     organism = synthetic construct
SEQUENCE: 29

```
atgacaataa aggaaatgcc gcagccgaaa acgtttggag aacttaaaaa tttaccgtta  60
ttaaacacag ataaaccggt tcaagctttg atgaaaattg cggatgaatt aggagaaatc 120
tttaaattcg aggcgcctgg ttttggtaacg atttactat caagtcagcg tctaattaaa 180
gaagcatgcg atgaatcacg ctttgataaa aacttaagtc aggcgatgaa atttgcacgt 240
gatttttctg gagacgggtt agcaacaagc tggacgcaca aaataaattg gaaaaaagcg 300
cataatatct tacttccaag ctttagtcag caggcaatga aaggctatca tgccgatatg 360
gtcgatatcg ccgtgcagct tgttcaaaag tgggagcgtc taaatgcaga tgagcatatt 420
gaagtatcgg aagacatgac acgtttaacg cttgatacaa ttggtcttttg cggctttaac 480
tatcgtttta caagctttta ccgagatcag cctcatccat ttattgtgag tatggtccgt 540
gcactggatg aagtaatgaa caagcgtcag cgagcaaatc cagacgaccc agcttatgat 600
gaaaacaagc gccagtgtca agaagatatc aaggtgatga acgaccagt agataaaatt 660
attgcagatc gcaaagcaag gggtgaacaa cgtgatgatt tattaacgca gatgctaaac 720
ggaaaagatc cagaaacggg tgagccgctt gatgacggga acattagcta tcaaattatt 780
acattcttaa ttgcgggaca cgaaacaaca agtggtcttt tatcatttgc gctgtatttc 840
ttagtgaaaa atccacatgt attacaaaaa gtagcagaag aagcagcacg agttctagta 900
gatcctgttc caagctacaa acaagtcaaa cagcttaaat atgtcggcat ggtcttaaac 960
gaagcgctgc gcttatggcc aactgctcct gcgttttccc tatatgcaaa agaagatacg 1020
gtgcttggag agaatatcc tttggggaaa ggcgacgtgg taaatgttct gattcctcag 1080
cttcaccgtg ataaaacaat ttggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact tgaagatcca tacaaactac gagctcgata ttaagaaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtaccgaaaa agcagaaaa cgctcataat 1440
acgccgctct tgtgctata cggttcaaat atgggaacag ctgaaggaac ggcgcgtgat 1500
ttagcagata ttgcaatgag caaaggattt gcaccgcagg tcgcaacgct tgattcacac 1560
gccgaaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctgc gacgtatcaa 1740
```

```
aaagtgcctg cttttatcga tgaaacgctt gccgctaaag gggcagaaaa catcgctgac   1800
cgcggtgaag cagatgcaag cgacgacttt gaaggcaact atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctaggcgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag    2340
cttgaagcct tgcttgaaaa gcaagcctac aaagaacaag tgatggcaaa acgtttaaca   2400
atgcttgaac tgcttgaaaa ataccgggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacattttt acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttggccaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg gatggggtaa                                    3150

SEQ ID NO: 30           moltype = AA   length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 30
MTIKEMPQPK TFGELKNLPL LNTDKPVQAL MKIADELGEI FKFEAPGLVT IYLSSQRLIK     60
EACDESRFDK NLSQAMKFAR DFLGDGLATS WTHEINWKKA HNILLPSFSQ QAMKGYHAMM    120
VDIAVQLVQK WERLNADEHI EVSEDMTRLT LDTIGLCGFN YRFNSFYRDQ PHPFIVSMVR    180
ALDEVMNKRQ RANPDDPAYD ENKRQCQEDI KVMNDLVDKI IADRKARGEQ RDDLLTQMLN    240
GKDPETGEPL DDGNISYQII TFLIAGHETT SGLLSFALYF LVKNPHVLQK VAEEAARVLV    300
DPVPSYKQVK QLKYVGMVLN EALRLWPTAP AFSLYAKEDT VLGGEYPLAK GDEVNVLIPQ    360
LHRDKTIWGD DVEEFRPERF ENPSAIPQHA FKPFGNGQRA CIGQQFALHE ATLVLGMMLK    420
HFDFEDHTNY ELDIKETLTL KPEGFVVKAK SKKIPLGGIP SPSTEQSAKK VRKKAENAHN    480
TPLLVLYGSN MGTAEGTARD LADIAMSKGF APQVATLDSH AGNLPREGAV LIVTASYNGH    540
PPDNAKQFVD WLDQASADEV KGVRYSVFGC GDKNWAATYQ KVPAFIDETL AAKGAENIAD    600
RGEADASDDF EGNYEEWREH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LGASQQIRLE AEEEKLAHLP LAKTVSVEEL LQYVELQDPA TRTQLRAMAA KTVCPPHKVE    780
LEALLEKQAY KEQVMAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LGQGAHFYIC GDGSQMAPAV EATLMKSYAD   1020
VHQVSEADAR LWLQQLEEKG RYAKDVWMG                                    1049

SEQ ID NO: 31           moltype = DNA   length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 31
atgacaataa aggaaatgcc gcagccgaaa acgtttggag aacttaaaaa tttaccgtta     60
ttaaacacag ataaaccggt tcaagctttg atgaaaattg cggatgaatt aggagaaatc    120
tttaaattcg aggcgcctgg tttggtaacg atttacttat caagtcagcg tctaattaaa    180
gaagcatgcg atgaatcacg ctttgataaa aacttaagtc aggcgatgaa atttgccagt    240
gattttctgg gagacgggtt agcaacaagc tggacgcatg aaataaattg gaaaaaagcg    300
cataatatct tacttccaag ctttagtcag caggcaatga aggctatcat gcgatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagctttta ccgagatcag cctcatccat ttattataag tatggtcgt    540
gcactggatg aagtaatgaa caagcgtcag cgagcaaatc cagacgaccc agcttatgat    600
gaaaacaagc gccagtgtca agaagatatc aaggtgatga cgaccagt agataaaatt    660
attgcagatc gcaaagcaag gggtgaacaa cgtgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttc tcatttgc gctgtatttc    840
ttagtgaaaa atccacatgt attacaaaaa gtagcagaaa aagcagcacg agttctagta    900
gatcctgttc caagctacaa acaagtcaaa cagcttaaat atgtcggcat ggtcttaaac    960
gaagcgctgc gcttatggcc aactgctcct gcgtttcccc tatatgcaaa agaagatacg   1020
gtgcttggag gagaatatcc tttagaaaaa ggcgacgaag taaatgttct gattcctcag   1080
cttcaccgtg ataaaacaat ttggggagac gatgtggagg agttccgtcc agagcgtttt   1140
```

```
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatcat acaaactac gagctcaaaa ttaaagaaac tttaacgtta   1320
aaacctgaag gctttgtggt aaaagcaaaa tcgaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggccgcgtgat  1500
ttagcagata ttgcaatgag caaaggattt gcaccgcagg tcgcaacgct tgattcacac   1560
gccgaaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaggcgttc gctactccgt atttggatgc ggcgataaaa actgggctac tacgtatcaa   1740
aaagtgcctg ctttatcga tgaaacgctt gccgctaaag gggcagaaaa catcgctgac   1800
cgcggtgaag cagatgcaag cgacgacttt gaaggcaact atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gccgccgca taagtagag    2340
cttgaagcct tgcttgaaaa gcaagcctac aagaacaag tgctggcaaa cgtttaaca    2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag acctgaaac gccgcttatc   2700
atggtcggac cgggaacagg cgtcgcgccg tttagaggcc ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg gatggggtaa                                    3150

SEQ ID NO: 32           moltype = AA   length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 32
MTIKEMPQPK TFGELKNLPL LNTDKPVQAL MKIADELGEI FKFEAPGLVT IYLSSQRLIK     60
EACDESRFDK NLSQAMKFAR DFLGDGLATS WTHEINWKKA HNILLPSFSQ QAMKGYHAMM   120
VDIAVQLVQK WERLNADEHI EVSEDMTRLT LDTIGLCGFN YRFNSFYRDQ PHPFIISMVR   180
ALDEVMNKRQ RANPDDPAYD ENKRQCQEDI KVMNDLVDKI IADRKARGEQ RDDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVNVLIPQ   360
LHRDKTIWGD DVEEFRPERF ENPSAIPQHA FKPFGNGQRA CIGQQFALHE ATLVLGMMLK   420
HFDFEDHTNY ELKIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGNYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPA TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWMG                                    1049

SEQ ID NO: 33           moltype = DNA   length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 33
atgacaataa aggaaatgcc gcagccgaaa acgtttggag aacttaaaaa tttaccgtta     60
ttaaacacag ataaaccggt tcaagctttg atgaaaattg cggatgaatt aggagaaatc   120
tttaaattcg aggcgcctgg ttttggtaac atttttttat caagtcagcg tctaattaaa   180
gaagcatgcg atgaatcacg ctttgataaa aacttaagtc aggcagatga atttgcacgt   240
gattttctgg gagacgggtt agcaacaagc tggacgcatg aaataaattg gaaaaaagcg   300
cataatatct tacttccaag cttttagtcag caggcaatga aaggctatca tgcgatgatg   360
gtcgatatcg ccgtgcagct tgttcaaaag tgggagcgtc taaatgcaga tgagcatatt   420
gaagtatcgg aagacatgac acgtttaacg cttgataaa ttggtctttg cggctttaac   480
tatcgcttta acagctttta ccgagatcag cctcatccat ttattataag tatggtccgt    540
```

```
gcactggatg aagtaatgaa caagcgtcag cgagcaaatc cagacgaccc agcttatgat    600
gaaaacaagc gccagtgtca agaagatatc aaggtgatga acgactatgt agatcgtatt    660
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatca tacaaactac gagctccgta ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagtatg gcgtgagcat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacggacg atcttgaaat tgaacttcca aagaagctt cttatcaaga aggagatcat   2100
ttaggtgtta ttcctcgcaa ctatgaagga atagtaaacc gtgtaacagc aaggttcgga   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatgcctgct aaaacggtct gcccgccgca taagtagag   2340
cttgaagcct tgcttgaaaa gcaagcctac aaagaacaag tgctggcaaa acgtttaaca   2400
atgcttgaac tgcttgaaaa ataccggcg tgtgaaatga attcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                    3150

SEQ ID NO: 34          moltype = AA  length = 1049
FEATURE                Location/Qualifiers
REGION                 1..1049
                       note = synthetic P450-BM3 variant polypeptide
source                 1..1049
                       mol_type = protein
                       organism = synthetic construct
SEQUENCE: 34
MTIKEMPQPK TFGELKNLPL LNTDKPVQAL MKIADELGEI FKFEAPGLVT IFLSSQRLIK     60
EACDESRFDK NLSQAMKFAR DFLGDGLATS WTHEINWKKA HNILLPSFSQ QAMKGYHAMM    120
VDIAVQLVQK WERLNADEHI EVSEDMTRLT LDTIGLCGFN YRFNSFYRDQ PHPFIISMVR    180
ALDEVMNKRQ RANPDDPAYD ENKRQCQEDI KVMNDYVDRI IADRKARGEQ SDDLLTQMLN    240
GKDPETGEPL DDGNISYQII TFLIAGHETT SGLLSFALYF LVKNPHVLQK VAEEAARVLV    300
DPVPSYKQVK QLKYVGMVLN EALRLWPTAP AFSLYAKEDT VLGGEYPLEK GDEVNVLIPQ    360
LHRDKTIWGD DVEEFRPERF ENPSAIPQHA FKPFGNGQRA CIGQQFALHE ATLVLGMMLK    420
HFDFEDHTNY ELRIKETLTL KPEGFVVKAK SKKIPLGGIP SPSTEQSAKK VRKKAENAHN    480
TPLLVLYGSN MGTAEGTARD LADIAMSKGF APQVATLDSH AGNLPREGAV LIVTASYNGH    540
PPDNAKQFVD WLDQASADEV KGVRYSVFGC GDKNWATTYQ KVPAFIDETL AAKGAENIAD    600
RGEADASDDF EGTYEVWREH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LDASQQIRLE AEEEKLAHLP LAKTVSVEEL LQYVELQDPA TRTQLRAMAA KTVCPPHKVE    780
LEALLEKQAY KEQVLAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 35          moltype = DNA  length = 3150
FEATURE                Location/Qualifiers
misc_feature           1..3150
                       note = synthetic P450-BM3 variant polynucleotide
source                 1..3150
                       mol_type = other DNA
                       organism = synthetic construct
```

```
SEQUENCE: 35
atgacaataa aggaaatgcc gcagccgaaa acgtttggag aacttaaaaa tttaccgtta    60
ttaaacacag ataaaccggt tcaagctttg atgcgtattg cggatgaatt aggagaaatc   120
tttaaattcg aggcgcctgg tttggtaacg atttacttat caagtcagcg tctaattaaa   180
gaagcatgcg atgaatcacg ctttgataaa aacttaagtc aggcgatgaa atttgcacgt   240
gattttctgg gagacgggtt agcaacaagc tggacgcatg aaccgaattg gaaaaaagcg   300
cataatatct tacttccaag ctttagtcag caggcaatga aacgttatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta acagctttta ccgagatcag cctcatccat ttattgtgag tatggtccgt   540
gcactggatg aagtaatgaa caagcgtcag cgagcaaatc cagacgaccc agcttatgat   600
gaaaacaagc gccagtgtca agaagatatc aaggtgatga acgaccagt agataaaatt   660
attgcagatc gcaaagcaag gggtgaacaa agccatgatt tattaacgca gatgctaaac   720
ggaaaagatc cagaaacggg tgagccgctt gatgacgggaa acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc aagctacaa acaagtcaaa cagcttaaat atgtcggcat ggtcttaaac   960
gaagcgctgc gcttatggcc aactgctcct cgtttttccc tatatgcaaa agaagatacg  1020
gtgcttggag gagaatatcc tttagaaaaa ggcgacgaag taaatgttct gattcctcag  1080
cttcaccgtg ataaaacaat ttggggagac gatgtggagg agttccgtcc agagcgtttt  1140
gaaaatccaa gtgcgattcc gcagcatgcg tttaaaccgt ttggaacgg tcagcgtgcg  1200
tgtatcggtc agcagttcgc tcttcatgaa gcaacgctg tacttggtat gatgctaaaa  1260
cactttgact tgaagatca tacaaactac gagctcgata ttaaagaaac tttaacgtta  1320
aaacctgaag gctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat gcgggaacga ctgaaggaac ggcgcgtgat  1500
ttagcagata ttgcaatgag caaaggattt gcaccgcagg tcgcaacgct tgattcacac  1560
gccgaaatc ttccgcgcga aggagctgta ttaattgtaa cggcgcttta taacggtcat  1620
ccgcctgata acgcaaagca atttgtcgac tggttagacc aagcgtctgc tgatgaagta  1680
aaaggcgttc gctactccgt atttggatgc ggcaataaa actgggctac tacgtatcaa  1740
aaagtgcctg cttttatcga tgaaacgctt gccgctaaag ggcagaaaa catcgctgac  1800
cgcggtgaag cagatgcaag cgacgacttt gaaggcacat atgaagatg gcgtgaacat  1860
atgtggagtc acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaaa aaaaattagc tcatttgcca  2220
ctcgctaaaa cagtatccgt agaagcgctt ctgcaatacg tggagcttca agatcctgcg  2280
acgcgcacgc agcttcgcgc aatggctgct aaaacggtct gcccgccgca taaagtagag  2340
cttgaagcct tgcttgaaaa gcaagcctac aagaacaag tgctggcaaa acgtttaaca  2400
atgcttgaac tgcttgaaaa ataccgcgcg tgtgaaatga aattcagcga atttatcgcc  2460
cttctgccaa gcatacgccc gcgctattac tcgatttctt catcacctcg tgtcgataaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cgggaacagg cgtcgcgccg tttagacgt ttgtgcaggc ggcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg ctttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                    3150

SEQ ID NO: 36         moltype = AA  length = 1049
FEATURE               Location/Qualifiers
REGION                1..1049
                      note = synthetic P450-BM3 variant polypeptide
source                1..1049
                      mol_type = protein
                      organism = synthetic construct
SEQUENCE: 36
MTIKEMPQPK TFGELKNLPL LNTDKPVQAL MRIADELGEI FKFEAPGLVT IYLSSQRLIK   60
EACDESRFDK NLSQAMKFAR DFLGDGLATS WTHEPNWKKA HNILLPSFSQ QAMKRYHAMM  120
VDIAVQLVQK WERLNADEHI EVSEDMTRLT LDTIGLCGFN YRFNSFYRDQ PHPFIVSMVR  180
ALDEVMNKRQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
```

-continued

```
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 37           moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 37
atgacaataa aggaaatgcc gcagccgaaa acgtttggag aacttaaaaa tttaccgtta   60
ttaaacacag ataaaccggt tcaagctttg atgcgtattg cggatgaatt aggagaaatc   120
tttaaattcg aggcgcctgg ttcagtaacg atttctttat caagtcagcg tctaattaaa   180
gaagcatgcg atgaatcacg ctttgataaa aacttaagtc aggcgatgaa atttgcacgt   240
gattttctgg gagacgggtt agcaacaagc tggacgcatg aaccgaattg gaaaaaagcg   300
cataatatct tacttccaag cttagtcag caggcaatga acgttatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta cagcttttta ccgagatcag cctcatccat ttattgtgag tatggtccgt   540
gcactggatg aagtaatgaa caagcgtcag cgagcaaatc cagacgaccc agcttatgat   600
gaaaacaagc gccagtgtca agaagatatc aaggtgatga acgactatgt agataaaatt   660
attgcagatc gcaaagcaag gggtgaacaa agccatgatt tattaacgca gatgctaaac   720
ggaaaagatc cagaaacggg tgagccgctt gatgacggga acattagcta tcaaattatt   780
acattcttaa ttgcgggaca cgaaacaaca agtggtcttt atcatttgc gctgtatttc   840
ttagtgaaaa atccacatgt attacaaaga gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgtttccc tatatgcaaa agaagatacg   1020
gtgcttggag gagaatatcc tttaagaaa ggcgacgaag taaatgttct gattcctcag   1080
cttcaccgtg ataaacaat tggggagac gatgtgaggg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat gcgggaacag ctgaaggaac ggcgcgtgat   1500
ttagcagata ttgcaatgag caaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaac cctgggctgc tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg gcgtgatcat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctgaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagagg   2340
cttgaagcct tgcttaaaaa gcaagcctac aaagaacaag tgctggcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cggaacagg cgtcgcgccg tttagaggct ttgtcaggc gcgcaaacag   2760
ctaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag agcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                   3150

SEQ ID NO: 38           moltype = AA   length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 38
MTIKEMPQPK TFGELKNLPL LNTDKPVQAL MRIADELGEI FKFEAPGSVT IFLSSQRLIK   60
EACDESRFDK NLSQAMKFAR DFLGDGLATS WTHEPNWKKA HNILLPSFSQ QAMKRYHAMM   120
VDIAVQLVQK WERLNADEHI EVSEDMTRLT LDTIGLCGFN YRFNSFYRDQ PHPFIVSMVR   180
ALDEVMNKRQ RANPDDPAYD ENKRQCQEDI KVMNDYVDKI IADRKARGEQ SHDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLKK GDEVNVLIPQ   360
```

```
LHRDKTIWGD DVEEFRPERF ENPSAIPQHA FKPFGNGQRA CIGQQFALHE ATLVLGMMLK    420
HFDFEDHTNY ELDIKETLTL KPEGFVVKAK SKKIPLGGIP SPSTEQSAKK VRKKAENAHN    480
TPLLVLYGSN AGTAEGTARD LADIAMSKGF APQVATLDSH AGNLPREGAV LIVTASYNGH    540
PPDNAKQFVD WLDQASADEV KGVRYSVFGC GDKTWAATYQ KVPAFIDETL AAKGAENIAD    600
RGEADASDDF EGTYEEWRDH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LDASQQIRLE AEEEKLAHLP LAKTVSVEEL LQYVELQDPA TRTQLRAMAA KTVCPPHKVE    780
LEALLEKQAY KEQVLAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 39              moltype = DNA  length = 3150
FEATURE                    Location/Qualifiers
misc_feature               1..3150
                           note = synthetic P450-BM3 variant polynucleotide
source                     1..3150
                           mol_type = other DNA
                           organism = synthetic construct
SEQUENCE: 39
atgacaataa aggaaatgcc gcagccgaaa acgtttggag aacttaaaaa tttaccgtta   60
ttaaacacag ataaaccggt tcaagctttg atgcgtattg cggatgaatt aggagaaatc   120
tttaaattcg aggcgcctgg ttcagtaacg atttacttat caagtcagcg tctaattaaa   180
gaagcatgcg atgaatcacg ctttgataaa aacttaagtc aggcgatgaa atttgcacgt   240
gattttctgg gagacgggtt agcaacaagc tggacgcatg aaccgaattg gaaaaagcg   300
cataatatct tacttccaag ctttagtcag caggcaatga aacgttatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta acagcttta ccgagatcag cctcatccat ttattgtgag tatggtcgtt   540
gcactggatg aagtaatgaa caagcgtcag cgagcaaatc cagacgaccc agcttatgat   600
gaaaacaagc gccagtgtca agaagatatc aaggtgatga acgaccagt agataaaatt   660
attgcagatc gcaaagcaag gggtgaacaa agccatgatt tattaacgca gatgctaaac   720
ggaaaagatc cagaaacggg tgagccgctt gatgacggga acattagcta tcaaattatt   780
acattcttaa ttgcgggaca cgaaacaaca gtggtctttt tatcatttgc gctgtatttc   840
ttagtgaaaa atccacatgt attacaaaaa gtagcagaag aagcagcacg agttctagta   900
gatcctgttc aagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttaaagaaa ggcgacgaag taaatgttct gattcctcag  1080
cttcaccgtg ataaaacaat ttggggagac gatgtggagg agttccgtcc agagcgtttt  1140
gaaaatccaa gtgcgattcc gcagcatgcg tttaaaccgt ttggaaacgg tcagcgtgcg  1200
tgtatccggtc agcagttcgc tcttcatgaa gcaacgctgg tacttggtat gatgctaaaa  1260
cactttgact ttgaagataa tacaaactac gagctcgata ttaaagaaac tttaacgtta  1320
aaacctgaag gctttgtggt aaaagcaaaa tcgaaaggta ttccgcttgg cggtattcct  1380
tcacctagca ctgaacagtc tgctaaaaaa gtacgcaaaa aggcagaaaa cgctcataat  1440
acgccgctgc ttgtgctata cggttcaaat gcggaacag ctgaaggaac ggcgcgtgat  1500
ttagcagata ttgcaatgag caaagattt gcaccgcagc tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa ctgggctgc tacgtatcaa  1740
aaagtgcctg cttttatcga tgaaacgctt gccgctaaag gggcagaaaa catcgctgac  1800
cgcggtgaag cagatgcaag cgacgacttt gaaggcacat atgaagaatg gcgtgatcat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattagc tcatttgcca  2220
ctcgctaaaa cagtatccgt agaagagctt ctgcaatacg tggagcttca agatcctgcg  2280
acgcgcacgc agcttcgcgc aatggctgct aaaacggtct gcccgccgca taaagtagag  2340
cttgaagcct tgcttgaaaa gcaagcctac aaagaacaag tgctggcaaa acgtttaaca  2400
atgcttgaac tgcttgaaaa ataccgggcg tgtgaaatga attcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cgggaacagg cgtcgcgccg tttagaggct ttgtgcaggc cgcaaacag  2760
ctaaaagaac aaggacagtc acttggagaa gcacatttat acttcggctg ccgttcacct  2820
catgagact atctgtatca agaagagctt gaaaacgccc aaagcgaagg catcattacg  2880
cttcataccg cttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                   3150

SEQ ID NO: 40              moltype = AA  length = 1049
FEATURE                    Location/Qualifiers
REGION                     1..1049
                           note = synthetic P450-BM3 variant polypeptide
```

```
source                  1..1049
                        mol_type = protein
                        organism = synthetic construct
SEQUENCE: 40
MTIKEMPQPK TFGELKNLPL LNTDKPVQAL MRIADELGEI FKFEAPGSVT IYLSSQRLIK    60
EACDESRFDK NLSQAMKFAR DFLGDGLATS WTHEPNWKKA HNILLPSFSQ QAMKRYHAMM  120
VDIAVQLVQK WERLNADEHI EVSEDMTRLT LDTIGLCGFN YRFNSFYRDQ PHPFIVSMVR  180
ALDEVMNKRQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLKK GDEVNVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKGIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWAATYQ KVPAFIDETL AAKGAENIAD  600
RGEADASDDF EGTYEEWRDH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPA TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049

SEQ ID NO: 41           moltype = DNA   length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 41
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa atttgcacgt   240
gattttgcag gagacgggtt ggtgacaagc tggacgcatg aaataaattg gaaaaaagcg   300
cataatatct tacttccaag ctttagtcag caggcaatga aaggctatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtcttg cggctttaac   480
tatcgcttta acagcttta ccgagatcag cctcatccat ttattataag tatggtccgt   540
gcactggatg aagtaatgaa caagctgcag cgagcaaatc cagacgaccc agcttatgat   600
gaaaacaagc gccagtgtca agaagatatc aaggtgatga cgaccagtag ataaaaatt   660
attgctgca gaaaagcaag gggtgaacaa agcgctaat tattaacgca gatgctaaac   720
ggaaaagatc cagaaacggg tgagccgctt gatgacggga acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag agaatatcc tttagaaaaa ggcgacgaag taatggttct gattcctcag  1080
cttcaccgtg ataaaacaat tgggggagac gatgtggagg agttccgtcc agagcgtttt  1140
gaaaatccaa gtgcgattcc gcagcatgcg tttaaaccgt ttggaaacgg tcagcgtgca  1200
tgtatcggtc agcagttcgc tcttcatgaa gcaacgctgg tacttggtat gatgctaaaa  1260
cactttgact tgaagatca tacaaactac gagctcgata ttaaagaaac tttaacgtta  1320
aaacctgaag gctttgtggt aaaagcaaaa tcgaaaaaa ttccgcttgg cggtattcct  1380
tcacctagca ctgaacagtc tgctaaaaaa gtaccgaaaa aggcagaaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccgaaaatc ttccgcgcga aggagctgta ttaattgtaa cggcgtctta taacggtcat  1620
ccgcctgata acgcaaagca atttgtcgac tggttagacc aagctctgc tgatgaagta  1680
aaaggcgttc gctactccgt atttggatgc ggcgataaaa actgggctac tacgtatcaa  1740
aaagtgcctg ctttttatcga tgaaacgctt gccgctaaag gggcagaaaa catcgctgac  1800
cgcggtgaag cagatgcaag cgacgacttt gaaggcacat atgaagaatg cgtgaacat  1860
atgtggagtg acgtagcagc ctactttaac ctcgacattg aaaacagtga agataataaa  1920
tctactcttt cacttcaatt tgtcgacagc gccgcgaata tgccgcttgc gaaaatgcac  1980
ggtgcgtttt caacgaacgt cgtagcaagc aaagaactt c aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaaa aaaaattagc tcatttgcca  2220
ctcgctaaaa cagtatccgt agaagcttca gaactgttg agatcctgtt  2280
acgcgcacgc agcttcgcgc aatggctgct aaaacggtct gcccgccgca taaagtagag  2340
cttgaagcct tgcttgaaaa gcaagcctac aagaacaag tgctggcaaa cgtttaaca  2400
atgcttgaac tgcttgaaaa ataccc ggcg tgtgaaatga attcagcga tttatcgcc  2460
cttctgccaa gcatacgccc gcgctattac tcgatttctt catcacctcg tgtcgatgaa  2520
aaacaagcaa gcatcacggt ttgtgtc tcaggagaag cgtggagcgg atatggagaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cgggaacagg cgtcgcgccc tttagaggct tgtgcaggc gcgcaaacag  2760
ctaaagaac aaggacagtc acttggagaa gcacatttat acttcggctg ccgttcacct  2820
catgaagact atctgtatca agaagagctt gaaaacgccc aaagcgaagg catcattacg  2880
```

```
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                    3150
```

SEQ ID NO: 42              moltype = AA   length = 1049
FEATURE                    Location/Qualifiers
REGION                     1..1049
                           note = synthetic P450-BM3 variant polypeptide
source                     1..1049
                           mol_type = protein
                           organism = synthetic construct
SEQUENCE: 42

```
MTIKEMPQPK TFGELKNLPL LNTDKPVQAL MKIADELGEI FKFEAPGCVT RYLSSQRLIK    60
EACDESRFDK NLSQALKFAR DFAGDGLVTS WTHEINWKKA HNILLPSFSQ QAMKGYHAMM   120
VDIAVQLVQK WERLNADEHI EVSEDMTRLT LDTIGLCGFN YRFNSFYRDQ PHPFIISMVR   180
ALDEVMNKLQ RANPDDPAYD ENKRQCQEDI KVMNDLVDKI IADRKARGEQ SDDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                    1049
```

SEQ ID NO: 43              moltype = DNA   length = 3150
FEATURE                    Location/Qualifiers
misc_feature               1..3150
                           note = synthetic P450-BM3 variant polynucleotide
source                     1..3150
                           mol_type = other DNA
                           organism = synthetic construct
SEQUENCE: 43

```
atgacaataa aggaaatgcc gcagccgaaa acgtttggag aacttaaaaa tttaccgtta     60
ttaaacacag ataaaccggt tcaagctttg atgaaaattg ccgatgaatt aggagaaatc    120
tttaaattcg aggcgcctgg ttgtgtaacg cgctacttat caagtcagcg tctaattaaa    180
gaagcatgcg atgaatcacg ctttgataaa aacttaagtc aagcgcttaa atttgcacgt    240
gattttgcag gagacgggtt ggtgacaagc tggacgcatg aaccgaattg gaaaaaagcg    300
cataatatct tacttccaag ctttagtcag caggcaatga aagctatca tgccatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta cagcttttta ccgagatcag cctcatccat ttattgtgag tatggtccgt    540
gcactggatg aagtaatgaa caagctgcag cgagcaaatc cagacgaccc agcttatgat    600
gaaaacaagc gccagtgtca agaagatatc aaggtgatga cgaccctagt agataaaatt    660
attgcagatc gcaaagcaag gggtgaacaa agccacgatt tattaacgca gatgctaaac    720
ggaaaagatc cagaaacggg tgagccgctt gatgacggga cattagctca tcaaattatt    780
acattcttaa ttgcgggaca cgaaacaaca agtggtcttt tatcatttgc gctgtatttc    840
ttagtgaaaa atccacatgt attacaaaaa gtagcgaaga agcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taatggttct gattcctcaa   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaagaaaac tttaacgtta   1320
aaacctgaag gctttgttgt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagctctgc tgatgaagta   1680
aaaggcgttc gctactccgt atttggatgc ggcgataaaa actgggctac tacgtatcaa   1740
aaagtgcctg cttttatcga tgaaacgctt gccgctaaag ggcagaaaa catcgctgac   1800
cgcggtgaag cagatgcaag cgacgacttt gaaggcacat atgaagaatg cgtgaacat   1860
atgtggagtg acgtagcagc ctactttaac ctcgacattg aaacagtga gataataaa    1920
tctactcttt cacttcaatt tgtcgacagc gccgcgaata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctgaa gcagaagaag aaaaattagc tcatttgcca   2220
ctcgctaaaa cagtatccgt agaagagctt ctgcaatacg tggagcttca agatcctgtt   2280
```

```
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa ataccgggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaaa aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaacgcccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag agcgcacttc tatatttgc   3000
gggaggcggaa gccaaatggc acctgccgtt gaagcaacgc ttatgaaaag ctatgctgac   3060
gttcaccaag tgagtgaagc agacgctcgc ttatggctgc agcagctaga gaaaaaggc   3120
cgatacgcaa aagacgtgtg ggctgggtaa                                     3150

SEQ ID NO: 44              moltype = AA length = 1049
FEATURE                    Location/Qualifiers
REGION                     1..1049
                           note = synthetic P450-BM3 variant polypeptide
source                     1..1049
                           mol_type = protein
                           organism = synthetic construct
SEQUENCE: 44
MTIKEMPQPK TFGELKNLPL LNTDKPVQAL MKIADELGEI FKFEAPGCVT RYLSSQRLIK    60
EACDESRFDK NLSQALKFAR DFAGDGLVTS WTHEPNWKKA HNILLPSFSQ QAMKRYHAMM   120
VDIAVQLVQK WERLNADEHI EVSEDMTRLT LDTIGLCGFN YRFNSFYRDQ PHPFIVSMVR   180
ALDEVMNKLQ RANPDDPAYD ENKRQCQEDI KVMNDLVDKI IADRKARGEQ SHDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                    1049

SEQ ID NO: 45              moltype = DNA length = 3150
FEATURE                    Location/Qualifiers
misc_feature               1..3150
                           note = synthetic P450-BM3 variant polynucleotide
source                     1..3150
                           mol_type = other DNA
                           organism = synthetic construct
SEQUENCE: 45
atgacaataa aggaaatgcc gcagccgaaa acgtttggag aacttaaaaa tttaccgtta     60
ttaaacacag ataaaccggt tcaagctttg atgcgcattg cggatgaatt aggagaaatc    120
tttaaattcg aggcgcctgg ttgtgtaacg cgctacttat caagtcagcg tctaattaaa    180
gaagcatgcg atgaatcacg cttttgataaa aacttaagtc aagcgcttaa atttgcacgt    240
gattttgcag gagacgggtt ggtgacaagc tggacgcatg aaccgaattg gaaaaaagcg    300
cataatatct tacttccaag cttttagtcag caggcaatga aacgctatca tgcgatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagctttta ccgagatcag cctcatccat ttattgtgag tatggtccgt    540
gcactggatg aagtaatgaa caagctgcag cgagcaaatc cagacgaccc agcttatgat    600
gaaaacaagc gccagtgtca agaagatatc aaggtgatga cgaccagtg agataaaatt    660
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tcatttgc gctgtatttc    840
ttagtgaaaa atccacatgt attacaaaaa gtagcagaag agcagcacg agttctagta    900
gatcctgttc caagctacaa acaagtcaaa cagcttaaat atgtcggcat ggtcttaaac    960
gaagcgctgc gcttatggcc aactgctcct gcgtttccc tatatgcaaa agaagatacg   1020
gtgcttggag gagaatatcc tttagaaaaa ggcgacgaag taatggttct gattcctcaa   1080
cttcaccgtg ataaaacaat tggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaagaaac tttaacgtta   1320
aaacctgaag gctttgtggt aaaagcaaa tcgaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat gccggaacag ctgaaggaac ggcgcgtgat   1500
ttagcagata ttgcaatgag caaaggattt gcaccgcagg tcgcaacgct tgattcacac   1560
gccgaaaatc ttccgcgcga aggagctgta ttaattgtaa cggcgtctta taacggtcat   1620
ccgcctgata acgcaaagca atttgtcgac tggttagacc aagcgtctgc tgatgaagta   1680
```

-continued

```
aaaggcgttc gctactccgt atttggatgc ggcgataaaa actgggctac tacgtatcaa  1740
aaagtgcctg cttttatcga tgaaacgctt gccgctaaag gggcagaaaa catcgctgac  1800
cgcggtgaag cagatgcaag cgacgacttt gaaggcacat atgaagaatg gcgtgaacat  1860
atgtggagtg acgtagcagc ctactttaac ctcgacattg aaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattgac tcatttgcca  2220
ctcgctaaaa cagtatccgt agaagagctt ctgcaatacg tggagcttca agatcctgtt  2280
acgcgcacgc agcttcgcgc aatggctgct aaaacggtct gcccgccgca taagtagag  2340
cttgaagcct tgcttgaaaa gcaagcctac aagaacaag tgctggcaaa acgtttaaca  2400
atgcttgaac tgcttgaaaa atcccggcg tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttattcca caccgcagtc agaatttacg ctgccaaaag accctgaaac gccgcttatc  2700
atggtcggac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg cttttctcg catgccaaat cagccgaaaa catacgttca gcacgtaatg  2940
gaacaggacg gcaagaaatt gattgaactt ctgatcaag gagcgcactt ctatatttcg  3000
ggagacggaa gccaaatggc acctgccgtt gaagcaacgc ttatgaaaag ctatgctgac  3060
gttcaccaag tgagtgaagc agacgctcgc ttatggctgc agcagctaga gaaaaaggc  3120
cgatacgcaa aagacgtgtg ggctgggtaa                                    3150
```

SEQ ID NO: 46        moltype = AA  length = 1049
FEATURE              Location/Qualifiers
REGION               1..1049
                     note = synthetic P450-BM3 variant polypeptide
source               1..1049
                     mol_type = protein
                     organism = synthetic construct
SEQUENCE: 46

```
MTIKEMPQPK TFGELKNLPL LNTDKPVQAL MRIADELGEI FKFEAPGCVT RYLSSQRLIK   60
EACDESRFDK NLSQALKFAR DFAGDGLVTS WTHEPNWKKA HNILLPSFSQ QAMKRYHAMM  120
VDIAVQLVQK WERLNADEHI EVSEDMTRLT LDTIGLCGFN YRFNSFYRDQ PHPFIVSMVR  180
ALDEVMNKLQ RANPDDPAYD ENKRQCQEDI KVMNDLVDKI IADRKARGEQ SDDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPYY SISSSPRVDE   840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049
```

SEQ ID NO: 47        moltype = DNA  length = 3150
FEATURE              Location/Qualifiers
misc_feature         1..3150
                     note = synthetic P450-BM3 variant polynucleotide
source               1..3150
                     mol_type = other DNA
                     organism = synthetic construct
SEQUENCE: 47

```
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa atttgcacgt   240
gattttgcag gagacgggtt ggtgacaagc tggacacatg aaccgaattg gaaaaaagcg   300
cataatatct tacttccaag cttagtcag caggcaatga acgctatca tgcgatgatg   360
gtcgatatcg ccgtgcagct tgttcaaaag tgggagcgtc taaatgcaga tgagcatatt   420
gaagtatcga aagacatgac acgtttaacg cttgatacaa ttggtcttg cggcttaac   480
tatcgcttta acagcttta ccgagatcag cctcatcat ttattataag tatggtccgt   540
gcactggatg aagtaatgaa caagctgcag cgagcaaatc cagacgaccc agcttatgat   600
gaaacaagc gccagtgtca agaagatatc aaggtgatga cgaccgtagt agataaaatt   660
attgcagatc gcaaagcaag gggtgaacaa acgcgatgatt tattaacgca gatgctaaac   720
ggaaaaagat cagcagcggg tgagccgctt gatgacgagc aattagcta tcaaattatt   780
acattccttaa ttgcgggaca cgaaacaaca agtggtcttt tcatttgc gctgtatttc   840
ttagtgaaaaa tccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaag taatggttct gattcctcag  1080
```

-continued

```
cttcaccgtg ataaaacaat ttggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact ttgaagatca tacaaactac gagctcgata ttaaagaaac tttaacgtta  1320
aaacctgaag gctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat gccggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa actgggctac tacgtatcaa  1740
aaagtgcctg cttttatcga tgaaacgctt gccgctaaag gggcagaaaa catcgctgac  1800
cgcggtgaag cagatgcaag cgacgacttt gaaggcacat atgaagaatg gcgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattagc tcatttgcca  2220
ctcgctaaaa cagtatccgt agaagagctt ctgcaatacg tggagcttca agatcctgtt  2280
acgcgcacgc agcttcgcgc aatggctgct aaaacggtct gcccgccgca taagtagag  2340
cttgaagcct tgcttgaaaa gcaagcctac aaagaacaag tgctggcaaa acgtttaaca  2400
atgcttgaac tgcttgaaaa ataccccggcg tgtgaaatga aattcagcga atttatcgcc  2460
cttctgccaa gcatacgccc cgcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtcg  2640
tttatttcca caccgcagtc agaatttacg ctgccaaaaa accctgaaac gccgcttatc  2700
atggtcggac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg cttttttctcg catgccaaat cagccgaaaa catacgttca gcacgtaatg  2940
gaacaagacg gcaagaaatt gattgaactt ctttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                   3150
```

SEQ ID NO: 48        moltype = AA  length = 1049
FEATURE               Location/Qualifiers
REGION                1..1049
                         note = synthetic P450-BM3 variant polypeptide
source                1..1049
                         mol_type = protein
                         organism = synthetic construct
SEQUENCE: 48

```
MTIKEMPQPK TFGELKNLPL LNTDKPVQAL MKIADELGEI FKFEAPGCVT RYLSSQRLIK    60
EACDESRFDK NLSQALKFAR DFAGDGLVTS WTHEPNWKKA HNILLPSFSQ QAMKRYHAMM   120
VDIAVQLVQK WERLNADEHI EVSEDMTRLT LDTIGLCGFN YRFNSFYRDQ PHPFIISMVR   180
ALDEVMNKLQ RANPDDPAYD ENKRQCQEDI KVMNDLVDKI IADRKARGEQ SDDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN AGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDSQMAPAV EATLMKSYAD   1020
VHQVSEADAR LWLQQLEEKG RYAKDVWAG                                   1049
```

SEQ ID NO: 49        moltype = DNA  length = 3150
FEATURE               Location/Qualifiers
misc_feature        1..3150
                         note = synthetic P450-BM3 variant polynucleotide
source                1..3150
                         mol_type = other DNA
                         organism = synthetic construct
SEQUENCE: 49

```
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg ttgtgtaacg cgctacttga caagtcagcg tctaattaaa   180
gaagcatgcg atgaatcacg ctttgataaa aacttaagtc aagcgcttaa atttgcacgt   240
gattttgcag gagacgggtt ggtgacaagc tggacgcatg aaccgaattg gaaaaaagcg   300
cataatatct tacttccaag ctttagtcag caggcaatga aacgctatca tgcgatgatg   360
gtcgatatcg ccgtgcagct tgttcaaaag tgggagcgtc taaatgcaga tgagcatatt   420
gaagtatcgg aagacatgac acgtttaacg cttgataaa ttggtctttg cggctttaac   480
```

```
tatcgcttta acagctttta ccgagatcag cctcatccat ttattgtgag tatggtccgt   540
gcactggatg aagtaatgaa caagctgcag cgagcaaatc cagacgaccc agcttatgat   600
gaaaacaagc gccagtgtca agaagatatc aaggtgatga acgacctagt agataaaatt   660
attgcagatc gcaaagcaag gggtgaacaa agccacgatt tattaacgca gatgctaaac   720
ggaaaagatc cagaaacggg tgagccgctt gatgacgagg acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaag taatggttct gattcctcag  1080
cttcaccgtg ataaacaat ttggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact ttgaagatca tacaaactac gagctcgata ttaaagaaac tttaacgtta  1320
aaacctgaag gctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat gccggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa actgggctac tacgtatcaa  1740
aaagtgcctg ctttttatcga tgaaacgctt gccgctaaag gggcagaaaa catcgctgac  1800
cgcggtgaag cagatgcaag cgacgacttt gaaggcacat atgaagaatg cgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattagc tcatttgcca  2220
ctcgctaaaa cagtatccgt agaagagctt ctgcaatacg tggagcttca agatcctgtt  2280
acgcgcacgc agcttcgcgc aatggctgct aaaacggtct gcccgccgca taaagtagag  2340
cttgaagcct tgcttgaaaa gcaagcctac aaagaacaag tgctggcaaa cgtttaaca  2400
atgcttgaac tgcttgaaaa atacccggcg tgtgaaatga attcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cgggaacagg cgtcgcgccg tttagaggct ttgtgcaggc gcgcaaacag  2760
ctaaaagaac aaggacagtc acttggagaa gcacattta acttcggctg ccgttcacct  2820
catgaagact atctgtatca agaagagctt gaaaacgccc aaagcgaagg catcattacg  2880
cttcataccg cttttctcg catgccaaat cagccgaaaa catacgttca gcacgtaatg  2940
gaacaagacg gcaagaaatt gattgaactt cttgatcaag agcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                   3150
```

| SEQ ID NO: 50 | moltype = AA   length = 1049 |
|---|---|
| FEATURE | Location/Qualifiers |
| REGION | 1..1049 |
| | note = synthetic P450-BM3 variant polypeptide |
| source | 1..1049 |
| | mol_type = protein |
| | organism = synthetic construct |

SEQUENCE: 50
```
MTIKEMPQPK TFGELKNLPL LNTDKPVQAL MKIADELGEI FKFEAPGCVT RYLSSQRLIK    60
EACDESRFDK NLSQALKFAR DFAGDGLVTS WTHEPNWKKA HNILLPSFSQ QAMKRYHAMM  120
VDIAVQLVQK WERLNADEHI EVSEDMTRLT LDTIGLCGFN YRFNSFYRDQ PHPFIVSMVR  180
ALDEVMNKLQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049
```

| SEQ ID NO: 51 | moltype = DNA  length = 3150 |
|---|---|
| FEATURE | Location/Qualifiers |
| misc_feature | 1..3150 |
| | note = synthetic P450-BM3 variant polynucleotide |
| source | 1..3150 |
| | mol_type = other DNA |

```
                    organism = synthetic construct
SEQUENCE: 51
atgacaataa aggaaatgcc gcagccgaaa acgtttggag aacttaaaaa tttaccgtta    60
ttaaacacag ataaaccggt tcaagctttg atgcgcattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa atttgcacgt   240
gattttgcag gagacgggtt ggtgacaagc tggacgcatg aaataaattg gaaaaaagcg   300
cataatatct tacttccaag ctttagtcag caggcaatga aacgctatca tgcgatgatg   360
gtcgatatcg ccgtgcagct tgttcaaaag tgggagcgtc taaatgcaga tgagcatatt   420
gaagtatcgg aagacatgac acgtttaacg cttgatcaa ttggtctttg cggctttaac   480
tatcgcttta acagcttta ccgagatcag cctcatccat ttattataag tatggtccgt   540
gcactggatg aagtaatgaa caagctgcag cgagcaaatc cagacgaccc agcttatgat   600
gaaacaagc gccagtgtca agaagatatc aaggctgatga acgacctagt agataaaatt   660
attgcagatc gcaaagcaag gggtgaacaa agccacgatt tattaacgca gatgctaaac   720
ggaaaagatc cagaaacggg tgagccgctt gatgacggga acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaag taatggttct gattcctcag  1080
cttcaccgtg ataaaacaat tggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact tgaagatcaa tacaaactac gagctcgata ttaaagaaac tttaacgtta  1320
aaacctgaag ctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat gccggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgataagta  1680
aaaggcgttc gctactccgt atttggatgc ggcgataaaa actgggctac tacgtatcaa  1740
aaagtgcctg cttttatcga tgaaacgctt gccgctaaag gggcagaaaa catcgctgac  1800
cgcggtgaag cagatgcaag cgacgacttt gaaggcacat atgaagaatg cgtgaacat  1860
atgtggagtg acgtagcagc ctactttaac ctcgacattg aaaacagtga agataaataa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattagc tcatttgcca  2220
ctcgctaaaa cagtatccgt agaagagctt ctgcaatacg tggagcttca agatcctgtt  2280
acgcgcacgc agcttcgcgc aatggctgct aaaacggtct gccgccgca taagtagag  2340
cttgaagcct tgcttgaaaa gcaagcctac aagaacaag tgctggcaaa acgtttaaca  2400
atgcttgaac tgcttgaaaa aatcccggcg tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatgagaa  2580
tataaaggaa ttgcgtcgaa ctatcttgcc gagctgcaag aaggagatac gattacgtgc  2640
tttatttcca caccgcagtc agaatttacg ctgccaaaca accctgaaac gccgcttatc  2700
atggtcggac cgggaacagg cgtcgcgccg tttagaggct tgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcatacg ctttttctcg catgccaaat cagccgaaca catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                    3150

SEQ ID NO: 52         moltype = AA  length = 1049
FEATURE               Location/Qualifiers
REGION                1..1049
                      note = synthetic P450-BM3 variant polypeptide
source                1..1049
                      mol_type = protein
                      organism = synthetic construct
SEQUENCE: 52
MTIKEMPQPK TFGELKNLPL LNTDKPVQAL MRIADELGEI FKFEAPGCVT RYLSSQRLIK    60
EACDESRFDK NLSQALKFAR DFAGDGLVTS WTHEINWKKA HNILLPSFSQ QAMKRYHAMM   120
VDIAVQLVQK WERLNADEHI EVSEDMTRLT LDTIGLCGFN YRFNSFYRDQ PHPFIISMVR   180
ALDEVMNKLQ RANPDDPAYD ENKRQCQEDI KVMNDLVDKI IADRKARGEQ SHDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN AGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPYY SISSSPRVDE   840
KQASITVSVV SGEAWSGYGE YKGIASNYLA ELQEGDTITC FISTPQSEFT LPKDPETPLI   900
```

-continued

```
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 53           moltype = DNA   length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 53
atgacaataa aggaaatgcc gcagccgaaa acgtttggag aacttaaaaa tttaccgtta    60
ttaaacacag ataaaccggt tcaagctttg atgcgcattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa atttgcacgt   240
gattttgcag agacgggttt ggtgacaagc tggacgcatg aaataaattg gaaaaaagcg   300
cataatatct tacttccaag ctttagtcag caggcaatga aacgctatca tgccgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgctttta acagctttta ccgagatcag cctcatccat ttattataag tatggtccgt   540
gcactggatg aagtaatgaa caagctgcag cgagcaaatc cagacgaccc agcttatgat   600
gaaaacaagc gccagtgtca agaagatatc aaggtgatga acgacctagt agataaaatt   660
attgcagatc gcaaagcaag gggtgaacaa agcgatgatt tattaacgca gatgctaaac   720
ggaaaagatc cagaaacggg tgagccgctt gatgacggga acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaag taatggttct gattcctcag  1080
cttcaccgtg ataaaacaat ttggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact ttgaagatca tacaaactac gagctgatta caaagaaac tttaacgtta  1320
aaacctgaag gctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaaggcgttc gctactccgt atttggatgc ggcgataaaa actgggctac tacgtatcaa  1740
aaagtgcctg cttttatcga tgaaacgctt gtcgctaaag gggcagaaaa catcgctgac  1800
cgcggtgaag cagatgcaag cgacgacttt gaaggcacat atgaagaatg gcgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aaagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctgaaa gcagaagaag aaaaaattag tcatttgcca  2220
ctcgctaaaa cagtatccgt agaagagctt ctgcaatacg tggagcttca agatcctgtt  2280
acgcgcacgc agcttcgcgc aatgcgcgct aaaacggtct gcccgccgca taagtagag  2340
cttgaagcct tgcttgaaaa gcaagcctac aaagaacaag tgctggcaaa acgtttaaca  2400
atgcttgaac tgcttgaaaa ataccccggcg tgtgaaatga aattcagcga attatcgcc  2460
cttctgccaa gcatacgccc gcgctattac tcgatttctt catcacctcg tgtcgatgaa  2520
aaacaagcaa gcatcacggt cagcgttgtc tcaggaggaa cgtggagcgg atatgggaga  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cgggaacagg cgtcgcgccg tttagaggct tgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg ctttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa agacgtgtgg gctgggtaa                                    3150

SEQ ID NO: 54           moltype = AA    length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 54
MTIKEMPQPK TFGELKNLPL LNTDKPVQAL MRIADELGEI FKFEAPGCVT RYLSSQRLIK    60
EACDESRFDK NLSQALKFAR DFAGDGLVTS WTHEINWKKA HNILLPSFSQ QAMKRYHAMM   120
VDIAVQLVQK WERLNADEHI EVSEDMTRLT LDTIGLCGFN YRFNSFYRDQ PHPFIISMVR   180
ALDEVMNKLQ RANPDDPAYD ENKRQCQEDI KVMNDLVDKI IADRKARGEQ SDDLLTQMLN   240
GKDPETGEPL DDGNISYQII TFLIAGHETT SGLLSFALYF LVKNPHVLQK VAEEEAARVLV  300
```

```
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL VAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                   1049

SEQ ID NO: 55               moltype = DNA   length = 3150
FEATURE                     Location/Qualifiers
misc_feature                1..3150
                            note = synthetic P450-BM3 variant polynucleotide
source                      1..3150
                            mol_type = other DNA
                            organism = synthetic construct
SEQUENCE: 55
atgacaataa aggaaatgcc gcagccgaaa acgtttggag aacttaaaaa tttaccgtta   60
ttaaacacag ataaaccggt tcaagctttg atgcgcattg cggatgaatt aggagaaatc  120
tttaaattcg aggcgcctgg ttgtgtaacg cgctacttat caagtcagcg tctaattaaa  180
gaagcatgcg atgaatcacg ctttgataaa aacttaagtc aagcgcttaa atttgcacgt  240
gattttgcag gagacgggtt ggtgacaagc tggacgcatg aaccgaattg gaaaaaagcg  300
cataatatct tacttccaag cttttagtcag caggcaatga aacgtatca tgcgatgatg  360
gtcgatatcg ccgtgcagct tgttcaaaag tgggagcgtc taaatgcaga tgagcatatt  420
gaagtatcgg aagacatgac cgtttaacg cttgatacaa ttggtctttg cggctttaac  480
tatcgctttta acagcttttta ccgagatcag cctcatccat ttattataag tatggtccgt  540
gcactggatg aagtaatgaa caagctgcag cgagcaaatc cagacgaccc agcttatgat  600
gaaaacaagc gccagtgtca agaagatatc aaggtgatga acgaccagtt agatataaatt  660
attgcagatc gcaaagcaag gggtgaacaa agccacgatt tattaacgca gatgctaaac  720
ggaaaagatc cagaaacggg tgagccgctt gatgacggga acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgttttccc tatatgcaaa agaagatacg 1020
gtgcttggag gagaatatcc tttagaaaaa ggcgacgaag taatggttct gattcctcag 1080
cttcaccgtg ataaacaat ttggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttgtgat gatgctaaaa 1260
cactttgact tgaagatca tacaaactac gagctcgata ttaaagaaac tttaacgtta 1320
aaacctgaag gctttgtggt aaaagcaaaa tcgaaaaaaa ttccgcttgg cggtattcct 1380
tcacctgcag ctgaacagtc tgctaaaaaa gtacgcaaaa aggcagaaaa cgctcataat 1440
acgccgctgc ttgtgctata cggttcaaat gccggaacag ctgaaggaac ggcgcgtgat 1500
ttagcagata ttgcaatgag caaaggattt gcaccgcagg tcgcaacgct tgattcacac 1560
gccgaaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg ctttttatcga tgaaacgctt gccgctaaag gggcagaaaa catcgctgac 1800
cgcggtgaag cagatgcaag cgacgacttt gaaggcacat atgaagaatg cgtgaacat 1860
atgtggagtc acgtagcagc ctactttaac ctcgacattg aaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctgaaa gcagaagaaa aaaaattagc tcatttgcca 2220
ctcgctaaaa cagtatccgt tgaagagctt ctgcaatacg tggagcttca agatcctgtt 2280
acgcgcacgc agcttcgcgc aatggctgct aaaacggtct gcccgccgca taagtagag 2340
cttgaagcct tgcttgaaaa gcaagcctac aagaacaag tgctggcaaa acgtttaaca 2400
atgcttgaac tgcttgaaaa ataccccggcg tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggagaag cgtggagcgg atatggagaa 2580
tataaaggaa ttgcgtcgaa ctatcttgcc gagctgcaag aaggagatac gattacgtgc 2640
tttatttcca caccgcagtc agaatttacg ctgccaaaag accctgaaac gccgcttatc 2700
atggtcggac cgggaacagg cgtcgcgccg tttagaggct ttgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcataccg cttttttctcg catgccaaat cagccgaaaa catacgttca gcacgtaatg 2940
gaacaagacg gcaagaaatt gattgaactt cttgatcaag agcgcacttt ctatatttgc 3000
ggagacggaa gccaaatggc acctgccgtt gaagcaacgc ttatgaaaag ctatgctgac 3060
gttcaccaag tgagtgaagc agacgctcgc ttatggctgc agcagctaga agaaaaaggc 3120
cgatacgcaa aagacgtgtg ggctgggtaa                                 3150

SEQ ID NO: 56               moltype = AA    length = 1049
FEATURE                     Location/Qualifiers
REGION                      1..1049
```

```
                        note = synthetic P450-BM3 variant polypeptide
source                  1..1049
                        mol_type = protein
                        organism = synthetic construct
SEQUENCE: 56
MTIKEMPQPK  TFGELKNLPL  LNTDKPVQAL  MRIADELGEI  FKFEAPGCVT  RYLSSQRLIK   60
EACDESRFDK  NLSQALKFAR  DFAGDGLVTS  WTHEPNWKKA  HNILLPSFSQ  QAMKRYHAMM  120
VDIAVQLVQK  WERLNADEHI  EVSEDMTRLT  LDTIGLCGFN  YRFNSFYRDQ  PHPFIISMVR  180
ALDEVMNKLQ  RANPDDPAYD  ENKRQCQEDI  KVMNDLVDKI  IADRKARGEQ  SHDLLTQMLN  240
GKDPETGEPL  DDGNISYQII  TFLIAGHETT  SGLLSFALYF  LVKNPHVLQK  VAEEAARVLV  300
DPVPSYKQVK  QLKYVGMVLN  EALRLWPTAP  AFSLYAKEDT  VLGGEYPLEK  GDEVMVLIPQ  360
LHRDKTIWGD  DVEEFRPERF  ENPSAIPQHA  FKPFGNGQRA  CIGQQFALHE  ATLVLGMMLK  420
HFDFEDHTNY  ELDIKETLTL  KPEGFVVKAK  SKKIPLGGIP  SPSTEQSAKK  VRKKAENAHN  480
TPLLVLYGSN  AGTAEGTARD  LADIAMSKGF  APQVATLDSH  AGNLPREGAV  LIVTASYNGH  540
PPDNAKQFVD  WLDQASADEV  KGVRYSVFGC  GDKNWATTYQ  KVPAFIDETL  AAKGAENIAD  600
RGEADASDDF  EGTYEEWREH  MWSDVAAYFN  LDIENSEDNK  STLSLQFVDS  AADMPLAKMH  660
GAFSTNVVAS  KELQQPGSAR  STRHLEIELP  KEASYQEGDH  LGVIPRNYEG  IVNRVTARFG  720
LDASQQIRLE  AEEEKLAHLP  LAKTVSVEEL  LQYVELQDPV  TRTQLRAMAA  KTVCPPHKVE  780
LEALLEKQAY  KEQVLAKRLT  MLELLEKYPA  CEMKFSEFIA  LLPSIRPRYY  SISSSPRVDE  840
KQASITVSVV  SGEAWSGYGE  YKGIASNYLA  ELQEGDTITC  FISTPQSEFT  LPKDPETPLI  900
MVGPGTGVAP  FRGFVQARKQ  LKEQGQSLGE  AHLYFGCRSP  HEDYLYQEEL  ENAQSEGIIT  960
LHTAFSRMPN  QPKTYVQHVM  EQDGKKLIEL  LDQGAHFYIC  GDGSQMAPAV  EATLMKSYAD  1020
VHQVSEADAR  LWLQQLEEKG  RYAKDVWAG                                       1049

SEQ ID NO: 57           moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 57
atgacaataa  aggaaatgcc  gcagccgaaa  acgtttggag  aacttaaaaa  tttaccgtta    60
ttaaacacag  ataaaccggt  tcaagctttg  atgcgcattg  cggatgaatt  aggagaaatc   120
tttaaattcg  aggcgcctgg  ttgtgtaacg  cgctactat   caagtcagcg  tctaattaaa   180
gaagcatgcg  atgaatcacg  ctttgataaa  aacttaagtc  aagcgcttaa  atttgcacgt   240
gattttgcag  gagacgggtt  ggtgacaagc  tggacgcatg  aaccgaattg  gaaaaaagcg   300
cataatatct  tacttccaag  ctttagtcag  caggcaatga  aacgctatca  tgcgatgatg   360
gtcgatatcg  ccgtgcagct  tgttcaaaag  tgggagcgtc  taaatgcaga  tgagcatatt   420
gaagtatcgg  aagacatgac  acgtttaacg  cttgatacaa  ttggtctttg  cggctttaac   480
tatcgcttta  acagctttta  ccgagatcag  cctcatccat  ttattgtgag  tatggttccgt   540
gcactggatg  aagtaatgaa  caagctgcag  cgagcaaatc  cagacgaccc  agcttatgat   600
gaaaacaagc  gccagtgtca  agaagatatc  aaggtagtta  acgacctagt  agataaaatt   660
attcagatc   gcaaagcaag  gggtgaacaa  agccacgatt  tattaacgca  gatgctaaat   720
ggaaaagatc  cagaaacggg  tgagccgctt  gatgacggga  acattagcta  tcaaattatt   780
acattcttaa  ttgcgggaca  cgaaacaaca  agtggtcttt  tatcatttgc  gctgtatttc   840
ttagtgaaaa  atccacatgt  attacaaaaa  gtagcagaag  aagcagcacg  agttctagta   900
gatcctgttc  caagctacaa  acaagtcaaa  cagcttaaat  atgtcggcat  ggtcttaaac   960
gaagcgctgc  gcttatggcc  aactgctcct  gcgttttccc  tatatgcaaa  agaagatacg  1020
gtgcttggag  gagaatatcc  tttagaaaaa  ggcgacgaag  taatggttct  gattcctcag  1080
cttcaccgtg  ataaaacaat  ttggggagac  gatgtggagg  agttccgtcc  agagcgtttt  1140
gaaaatccaa  gtgcgattcc  gcagcatgcg  tttaaaccgt  ttggaaacgg  tcagcgtgcg  1200
tgtatcggtc  agcagttcgc  tcttcatgaa  gcaacgctgg  tacttggtat  gatgctaaaa  1260
cactttgact  tgaagatca   tacaaactac  gagctcgata  ttaaagaaac  tttaacgtta  1320
aaacctgaag  gctttgtggt  aaaagcaaa   tcgaaaaaaa  ttccgcttgg  cggtattcct  1380
tcacctagca  ctgaacagtc  tgctaaaaaa  gtacgcaaaa  aggcagaaaa  cgctcataat  1440
acgccgctgc  ttgtgctata  cggttcaaat  gccggaacag  ctgaaggaac  ggcgcgtgat  1500
ttagcagata  ttgcaatgag  caaaggattt  gcaccgcagg  tcgcaacgct  tgattcacac  1560
gccggaaatc  ttccgcgcga  aggagctgta  ttaattgtaa  cggcgtctta  taacggtcat  1620
ccgcctgata  acgcaaagca  atttgtcgac  tggttagacc  aagcgtctgc  tgatgaagta  1680
aaaggcgttc  gctactccgt  atttggatgc  ggcgataaaa  actgggctac  tacgtatcaa  1740
aaagtgcctg  cttttatcga  tgaaacgctt  gccgctaaag  ggcagaaaaa  catcgctgac  1800
cgcggtgaag  cagatgcaag  cgacgacttt  gaaggcacat  atgaagaatg  gcgtgaacat  1860
atgtggagtg  acgtagcagc  ctactttaac  ctcgacattg  aaaacagtga  agataataaa  1920
tctactcttt  cacttcaatt  tgtcgacagc  gccgcggata  tgccgcttgc  gaaaatgcac  1980
ggtgcgtttt  caacgaacgt  cgtagcaagc  aaagaacttc  aacagccagg  cagtgcacga  2040
agcacgcgac  atcttgaaat  tgaacttcca  aagaagcttc  ttatcaagag  aggagatcat  2100
ttaggtgtta  ttcctcgcaa  ctatgaagga  atagtaaacc  gtgtaacagc  aaggttcggc  2160
ctagatgcat  cacagcaaat  ccgtctgaa   gcagaagaa   aaaaattagc  tcatttgcca  2220
ctcgctaaaa  cagtatccgt  agaagagctt  ctgcaatacg  tggagcttca  agatcctgtt  2280
acgcgcacgc  agcttcgcgc  aatgctgct   aaaacggtct  gccgccgca   taagtagag   2340
cttgaagcct  tgcttgaaaa  gcaagcctac  aagaacaag   tgctggcaaa  cgtttaaca   2400
atgcttgaac  tgcttgaaaa  atacccggcg  tgtgaaatga  aattcagcga  atttatcgcc  2460
cttctgccaa  gcatacgccc  tcgctattac  tcgattcctt  catcacctcg  ttcgagcggg  2520
aaacaagcaa  gcatcacggt  cagcgttgtc  tcaggagaa   cgtcggagcgg  atatggagaa  2580
tataaaggaa  ttgcgtcgaa  ctatcttgcc  gagctgcaag  aaggagatac  gattacgtgc  2640
tttatttcca  caccgcagtc  agaatttacg  ctgccaaaag  accctgaaac  gccgcttatc  2700
atggtcggac  cgggaacagg  cgtcgcgccg  tttagaggct  tgtgtcaggc  gcgcaaacag  2760
ctaaagagaac  aaggacagtc  acttggagaa  gcacatttat  acttcggctg  ccgttcacct  2820
```

```
catgaagact atctgtatca agaagagctt gaaaacgccc aaagcgaagg catcattacg  2880
cttcataccg ctttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
cgatacgcaa aagacgtgtg ggctgggtaa                                   3150

SEQ ID NO: 58           moltype = AA   length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 58
MTIKEMPQPK TFGELKNLPL LNTDKPVQAL MRIADELGEI FKFEAPGCVT RYLSSQRLIK   60
EACDESRFDK NLSQALKFAR DFAGDGLVTS WTHEPNWKKA HNILLPSFSQ QAMKRYHAMM  120
VDIAVQLVQK WERLNADEHI EVSEDMTRLT LDTIGLCGFN YRFNSFYRDQ PHPFIVSMVR  180
ALDEVMNKLQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049

SEQ ID NO: 59           moltype = DNA   length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 59
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg ttgtgtaacg cgctactat caagtcagcg tctaattaaa  180
gaagcatgcg atgaatcacg ctttgataaa aacttaagtc aagcgcttaa atttgcacgt  240
gattttgcag gagacggggt ggtgacaagc tggacgcatg aaatacattg gaaaaaagcg  300
cataatatct tacttccaag ctttagtcag caggcaatga aacgctatca tgcgatgatg  360
gtcgatatcg ccgtgcagct tgttcaaaag tgggagcgtc taaatgcaga tgagcatatt  420
gaagtatcgg aagacatgac acgtttaacg cttgatacaa ttggtcttgtg cggctttaac  480
tatcgcttta acagctttta ccgagatcag cctcatccat ttattgtgag tatggtcgta  540
gcactggatg aagtaatgaa caagctgcag cgagcaaatc cagacgaccc agcttatgat  600
gaaaacaagc gccagtgtca agaagatatc aaggtgatga cgaccagtg agataaaatt  660
attgcagatc gcaaagcaag gggtgaacaa agccacgatt tattaacgca gatgctaaac  720
ggaaaagatc cagaaacggg tgagccgctt gatgacgtgga acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgtttttcc tatatgcaaa agaagatacg 1020
gtgcttggag gagaatatcc tttagaaaaa ggcgacgaag taatggttct gattcctcag 1080
cttcaccgtg ataaacaat tggggagac gatgtggagg agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cacttggact ttgaagatca tacaaactac gagctgataa ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat gccggaacag ctgaaggaac ggcgcgtgat 1500
ttagcagata ttgcaatgag caaaggattt gcaccgcagg tcgcaacgct tgattcacac 1560
gccgaaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggcta tacgtatcaa 1740
aaagtgcctg cttttatcga tgaaacgctt gccgctaaag ggcagaaaa catcgctgac 1800
cgcggtgaag cagatgcaag cgacgacttt gaaggcacat atgaagaatg gcgtgaacat 1860
atgtggagtg acgtagcagc ctactttaac ctcgacatcg aaaacagtga agataataaa 1920
tctactcttt cacttcaatt tgtcgacagc gccgcggata tgccgcttgc gaaaatgcac 1980
ggtgcgttt caacgaacgt cgtagcagc aaagaacttc aacagccagg cagtgcacga 2040
agcacgcgac atcttgaaat tgaacttcca aagaagcttc ttatcaagaa ggagatcat 2100
ttaggtgtta ttcctcgcaa ctatgaagga atagtaaacc gtgtaacagc aaggttcggc 2160
ctagatgcat cacagcaaat ccgtctggaa gcagaagaag aaaaattagc tcatttgcca 2220
```

-continued

```
ctcgctaaaa cagtatccgt agaagagctt ctgcaatacg tggagcttca agatcctgtt     2280
acgcgcacgc agcttcgcgc aatggctgct aaaacggtct gcccgccgca taaagtagag     2340
cttgaagcct tgcttgaaaa gcaagcctac aaagaacaag tgctggcaaa acgtttaaca     2400
atgcttgaac tgcttgaaaa ataccccggcg tgtgaaatga aattcagcga atttatcgcc     2460
cttctgccaa gcatacgccc gcgctattac tcgatttctt catcacctcg tgtcgatgaa     2520
aaacaagcaa gcatcacggt cagcgttgtc tcaggagaag cgtggagcgg atatggagaa     2580
tataaaggaa ttgcgtcgaa ctatcttgcc gagctgcaag aaggagatac gattacgtgc     2640
tttatttcca caccgcagtc agaatttacg ctgccaaaag accctgaaac gccgcttatc     2700
atggtcggac cgggaacagg cgtcgcgccg tttagaggct ttgtgcaggc gcgcaaacag     2760
ctaaaagaac aaggacagtc acttggagaa gcacatttat acttcggctg ccgttcacct     2820
catgaagact atctgtatca agaagagctt gaaaacgccc aaagcgaagg catcattacg     2880
cttcataccg cttttctcg catgccaaat cagccgaaaa catacgttca gcacgtaatg     2940
gaacaagacg gcaagaaatt gattgaactt cttgatcaag gagcgcactt ctatatttgc     3000
ggagacggaa gccaaatggc acctgccgtt gaagcaacgc ttatgaaaag ctatgctgac     3060
gttcaccaag tgagtgaagc agacgctcgc ttatggctgc agcagctaga agaaaaaggc     3120
cgatacgcaa aagacgtgtg ggctgggtaa                                      3150

SEQ ID NO: 60           moltype = AA  length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 60
MTIKEMPQPK TFGELKNLPL LNTDKPVQAL MKIADELGEI FKFEAPGCVT RYLSSQRLIK    60
EACDESRFDK NLSQALKFAR DFAGDGLVTS WTHEINWKKA HNILLPSFSQ QAMKRYHAMM   120
VDIAVQLVQK WERLNADEHI EVSEDMTRLT LDTIGLCGFN YRFNSFYRDQ PHPFIVSMVR   180
ALDEVMNKLQ RANPDDPAYD ENKRQCQEDI KVMNDLVDKI IADRKARGEQ SHDLLTQMLN   240
GKDPETGEPL DDGNISYQII TFLIAGHETT SGLLSFALYF LVKNPHVLQK VAEEAARVLV   300
DPVPSYKQVK QLKYVGMVLN EALRLWPTAP AFSLYAKEDT VLGGEYPLEK GDEVMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN AGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                    1049

SEQ ID NO: 61           moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 61
atgacaataa aggaaatgcc gcagccgaaa acgtttggag aacttaaaaa tttaccgtta     60
ttaaacacag ataaaccggt tcaagctttg atgaaaattg cggatgaatt aggagaaatc    120
tttaaattcg aggcgcctgg ttgtgtaacg cgctacttat caagtcagcg tctaattaaa    180
gaagcatgcg atgaatcacg ctttgataaa aacttaagtc aagcgcttaa atttgcacgt    240
gattttgcag gagacgggtt ggtgacaagc tggacgcatg aaataaattg gaaaaaagcg    300
cataatatct tacttccaag ctttagtcag caggcaatga aaggctatca tgcgatgatg    360
gtcgatatcg ccgtgcagct tgttcaaaag tgggagcgtc taaatgcaga tgagcatatt    420
gaagtatcgg aagacatgac acgtttaacg cttgatcaaa ttggtctttg cggctttaac    480
tatcgctttta acagcttta ccgagatcag cctcatccat ttattgtgag tatggtccgt    540
gcactggatg aagtaatgaa caagctgcag cgagcaaatc cagacgaccc agcttatgat    600
gaaaacaagc gccagtgtca agaagatatc aaggtgatga cgaccctagt agataaaatt    660
attgctgaca gcaaagcaag gggtgaacaa agcgataatt attaacgaca gatgctaaaa    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgtag aatggttct gattcctcag   1080
cttcaccgtg ataaaacaat tgggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat gccggaacag ctgaaggaac ggcgcgtgat   1500
ttagcagata ttgcaatgag caaggagttt gcaccgcagg tcgcaacgct tgattcacac   1560
gccggaaatc ttccgcgcga aggagctgta ttaattgtaa cggcgtctta taacggtcat   1620
```

```
ccgcctgata acgcaaagca atttgtcgac tggttagacc aagcgtctgc tgatgaagta  1680
aaaggcgttc gctactccgt atttggatgc ggcgataaaa actgggctac tacgtatcaa  1740
aaagtgcctg cttttatcga tgaaacgctt gccgctaaag gggcagaaaa catcgctgac  1800
cgcggtgaag cagatgcaag cgacgacttt gaaggcacat atgaagaatg gcgtgaacat  1860
atgtggagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctggaa gcagaagaag aaaaattagc tcatttgcca  2220
ctcgctaaaa cagtatccgt agaagagctt ctgcaatacg tggagcttca agatcctgtt  2280
acgcgcacgc agcttcgcgc aatggctgct aaaacggtct gccgccgca taagtagag  2340
cttgaagcct gccttgaaaa gcaagcctac aaagaacaag tgctggcaaa acgtttaaca  2400
atgcttgaac tgcttgaaaa atacccggcg tgtgaaatga aattcagcga atttatcgcc  2460
cttctgccaa gcatacgccc gcgctattac tcgatttctt catcacctcg tgtcgatgaa  2520
aaacaagcaa gcatcacggt cagcgttgtc tcaggagaag cgtggagcgg atatggagaa  2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcggac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg ctttttctcg catgccaaat cagccgaaaa catcgttca cgcgtaatg  2940
gaacaagacg gcaagaaatt gattgaactt cttgatcaag agcgcacttt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga gaaaaaggc  3120
cgatacgcaa aagacgtgtg ggctgggtaa                                   3150

SEQ ID NO: 62           moltype = AA  length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 62
MTIKEMPQPK TFGELKNLPL LNTDKPVQAL MKIADELGEI FKFEAPGCVT RYLSSQRLIK   60
EACDESRFDK NLSQALKFAR DFAGDGLVTS WTHEINWKKA HNILLPSFSQ QAMKGYHAMM  120
VDIAVQLVQK WERLNADEHI EVSEDMTRLT LDTIGLCGFN YRFNSFYRDQ PHPFIVSMVR  180
ALDEVMNKLQ RANPDDPAYD ENKRQCQEDI KVMNDLVDKI IADRKARGEQ SDDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQELQK LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049

SEQ ID NO: 63           moltype = DNA  length = 3150
FEATURE                 Location/Qualifiers
misc_feature            1..3150
                        note = synthetic P450-BM3 variant polynucleotide
source                  1..3150
                        mol_type = other DNA
                        organism = synthetic construct
SEQUENCE: 63
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg ttgtgtaacg cgctacttat caagtcagcg tctaattaaa  180
gaagcatgcg atgaatcacg cttttgataaa aacttaagtc aagcgcttaa atttgcacgt  240
gattttgcag gagacgggtt ggtgacaagc tggacgcatg aaccgaattg gaaaaagcg  300
cataatatct tacttccaag ctttagtcag caggcaatga aacgctatca tgccatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta acagcttta ccgagatcag cctcatccat ttattataag tatggtccgt  540
gcactggatg aagtaatgaa caagctgcag cgagcaaatc cagacgaccc agcttatgat  600
gaaaacaagc gccagtgtca agaagatatc aaggtgatga cgacctagt agataaaatt  660
attgctgaca gcaaagcaag gggtgaacaa agcacgtatt gataacgca gatgctaaac  720
ggaaaagatc cagaaacggg tgagccgctt gatgacggga acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttaat atgtcggcat ggtcttaaac  960
gaagcgctgc gcttatggcc aactgctcct gcgttttccc tatatgcaaa agaagatacg 1020
```

```
gtgcttggag gagaatatcc tttagaaaaa ggcgacgaag taatggttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatgcctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa ataccgcggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggaaga   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                    3150

SEQ ID NO: 64         moltype = AA  length = 1049
FEATURE               Location/Qualifiers
REGION                1..1049
                      note = synthetic P450-BM3 variant polypeptide
source                1..1049
                      mol_type = protein
                      organism = synthetic construct
SEQUENCE: 64
MTIKEMPQPK TFGELKNLPL LNTDKPVQAL MKIADELGEI FKFEAPGCVT RYLSSQRLIK   60
EACDESRFDK NLSQALKFAR DFAGDGLVTS WTHEPNWKKA HNILLPSFSQ QAMKRYHAMM  120
VDIAVQLVQK WERLNADEHI EVSEDMTRLT LDTIGLCGFN YRFNSFYRDQ PHPFIISMVR  180
ALDEVMNKLQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPYYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD 1020
VHQVSEADAR LWLQQLEEKG RYAKDVWAG                                   1049

SEQ ID NO: 65         moltype = DNA  length = 3150
FEATURE               Location/Qualifiers
misc_feature          1..3150
                      note = synthetic P450-BM3 variant polynucleotide
source                1..3150
                      mol_type = other DNA
                      organism = synthetic construct
SEQUENCE: 65
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa atttgcacgt   240
gattttgcag gagacgggtt ggtgacaagc tggacgcatg aaccgaattg gaaaaaagcg   300
cataatatct tacttccaag ctttgtcag caggcaatga aacgctatca tgcgatgatg   360
gtcgatatcg ccgtgcagct tgttcaaaag tgggagcgtc taaatgcaga tgagcatatt   420
```

```
gaagtatcgg aagacatgac acgtttaacg cttgatacaa ttggtctttg cggctttaac    480
tatcgcttta acagctttta ccgagatcag cctcatccat ttattgtgag tatggtccgt    540
gcactggatg aagtaatgaa caagctgcag cgagcaaatc cagacgaccc agcttatgat    600
gaaaacaagc gccagtgtca agaagatatc aaggtgatga acgacctagt agataaaatt    660
attgcagatc gcaaagcaag gggtgaacaa agccacgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taatggttct gattcctcag   1080
cttcaccgtg ataaacaat ttggggagac gatgtgagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaccgct tgattcacac   1560
gccgaaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tgtatatcaa   1740
aaagtgcctg cttttatcga tgaaacgctt gccgctaaaa gggcagaaaa catcgctgac   1800
cgcggtgaag cagatgcaag cgacgacttt gaaggcacat atgaagaatg cgtgaacat   1860
atgtggagtc acgtagcagc ctactttaac ctcgacattg aaacagtga agataataaa   1920
tctactcttt cacttcaatt tgtcgacagc gccgcggata tgccgcttgc gaaaatgcat   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctgaga gcagaagaaa aaaaattgac tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag   2340
cttgaagcct tgcttgaaaa gcaagcctac aaagaacaag tgctggcaaa acgtttaaca   2400
atgcttgaac tgcttgaaaa aatcccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggaagaa cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt ctggatcaag cacatttcta tatttgtggt   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                   3150
```

SEQ ID NO: 66          moltype = AA  length = 1049
FEATURE                Location/Qualifiers
REGION                 1..1049
                           note = synthetic P450-BM3 variant polypeptide
source                 1..1049
                           mol_type = protein
                           organism = synthetic construct SEQUENCE: 66
```
MTIKEMPQPK TFGELKNLPL LNTDKPVQAL MKIADELGEI FKFEAPGCVT RYLSSQRLIK      60
EACDESRFDK NLSQALKFAR DFAGDGLVTS WTHEPNWKKA HNILLPSFSQ QAMKRYHAMM    120
VDIAVQLVQK WERLNADEHI EVSEDMTRLT LDTIGLCGFN YRFNSFYRDQ PHPFIVSMVR    180
ALDEVMNKLQ RANPDDPAYD ENKRQCQEDI KVMNDLVDKI IADRKARGEQ SHDLLTQMLN    240
GKDPETGEPL DDGNISYQII TFLIAGHETT SGLLSFALYF LVKNPHVLQK VAEEEARVLV    300
DPVPSYKQVK QLKYVGMVLN EALRLWPTAP AFSLYAKEDT VLGGEYPLEK GDEVMVLIPQ    360
LHRDKTIWGD DVEEFRPERF ENPSAIPQHA FKPFGNGQRA CIGQQFALHE ATLVLGMMLK    420
HFDFEDHTNY ELDIKETLTL KPEGFVVKAK SKKIPLGGIP SPSTEQSAKK VRKKAENAHN    480
TPLLVLYGSN MGTAEGTARD LADIAMSKGF APQVAPLDSH AGNLPREGAV LIVTASYNGH    540
PPDNAKQFVD WLDQASADEV KGVRYSVFGC GDKNWATTYQ KVPAFIDETL AAKGAENIAD    600
RGEADASDDF EGTYEEWREH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LDASQQIRLE AEEEKLAHLP LAKTVSVEEL LQYVELQDPV TRTQLRAMAA KTVCPPHKVE    780
LEALLEKQAY KEQVLAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQAHFYIC GDGSQMAPAV EATLMKSYAD   1020
VHQVSEADAR LWLQQLEEKG RYAKDVWAG                                    1049
```

SEQ ID NO: 67          moltype = DNA  length = 3150
FEATURE                Location/Qualifiers
misc_feature        1..3150
                           note = synthetic P450-BM3 variant polynucleotide
source                 1..3150

```
                        mol_type = other DNA
                        organism = synthetic construct
SEQUENCE: 67
atgacaataa aggaaatgcc gcagccgaaa acgtttggag aacttaaaaa tttaccgtta   60
ttaaacacag ataaaccggt tcaagctttg atgaaaattg cggatgaatt aggagaaatc  120
tttaaattcg aggcgcctgg ttgtgtaacg cgctacttat caagtcagcg tctaattaaa  180
gaagcatgcg atgaatcacg ctttgataaa aacttaagtc aagcgcttaa atttgcacgt  240
gattttgcag gagacgggtt ggtgacaagc tggacgcatg aaccgaattg gaaaaaagcg  300
cataatatct tacttccaag cttttagtcag caggcaatga aaggctatca tgccgatgatg  360
gtcgatatcg ccgtgcagct tgttcaaaag tgggagcgtc taaatgcaga tgagcatatt  420
gaagtatcgg aagacatgac acgtttaacg cttgatacaa ttggtctttg cggctttaac  480
tatcgcttta acagctttta ccgagatcag cctcatccat ttattgtgag tatggtccgt  540
gcactggatg aagtaatgaa caagctgcag cgagccaaatc cagacgaccc agcttatgat  600
gaaaacaagc gccagtgtca agaagatatc aaggtgatga aaccgactag agataaaatt  660
attgcagatc gcaaagcaag gggtgaacaa agccacgatt tattaacgca gatgctaaac  720
ggaaaagatc cagaaacggg tgagccgctt gatgacggga acattagcta tcaaattatt  780
acattcttaa ttgcgggaca cgaaacaaca agtggtcttt tatcatttgc gctgtatttc  840
ttagtgaaaa atccacatgt attacaaaaa gtagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgttttccc tatatgcaaa agaagatacg 1020
gtgcttggag gagaatatcc tttagaaaaa ggcgacgaag taatggttct gattcctcag 1080
cttcaccgtg ataaaacaat ttggggagac gatgtggaag agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact tgaagatcat acaaactac gagctcgata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat gccggaacag ctgaaggaac ggcgcgtgat 1500
ttagcagata ttgcaatgag caaaggattt gcaccgcagg tcgcaacgct tgattcacac 1560
gccggaaatc ttccgcgcga aggagctgta ttaattgtaa ccgcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag gggcagaaaa catcgctgac 1800
cgcggtgaag cagatgcaag cgacgacttt gaaggcacat atgaagaatg gcgtgaacat 1860
atgtggagtg acgtagcagc ctactttaac ctcgacattg aaaacagtga agataataaa 1920
tctactcttt cacttcaatt tgtcgacagc gccgcggata tgccgcttgc gaaaatgcac 1980
ggtgcgtttt caacgaacgt cgtagcagcc aaagaacttc aacagccagg cagtgcacga 2040
agcacgcgac atcttgaaat tgaacttcca aagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctggaa gcagaagaag aaaaattagc tcatttgcca 2220
ctcgctaaaa cagtatccgt agaagagctt ctgcaatacg tggagcttca agatcctgtt 2280
acgcgcacgc agcttcgcgc aatggctgct aaaacggtct gcccgccgca taagtagag 2340
cttgaagcct tgcttgaaaa gcaagcctac aaagaacaag tgctggcaaa acgtttaaca 2400
atgcttgaac tgcttgaaaa ataccccggc tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggagaag cgtggagcgg atatggagaa 2580
tataaaggaa ttgcgtcgaa ctatcttgcc gagctgcaag aaggagatac gattacgtcg 2640
tttatttcca caccgcagtc agaatttacg ctgccaaaag accctgaaac gccgcttatc 2700
atggtcggac cgggaacagg cgtcgcgccg tttagaggct ttgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcataccg ctttttctcg catgccaaat cagccgaaaa catacgttca gcacgtaatg 2940
gaacaagacg gcaagaaatt gattgaactt cttgatcaag gagcgcactt ctatatttgc 3000
ggagacggaa gccaaatggc acctgccgtt gaagcaacgc ttatgaaaag ctatgctgac 3060
gttcaccaag tgagtgaagc agacgctcgc ttatggctgc agcagctaga agaaaaaggc 3120
cgatacgcaa aagacgtgtg ggctgggtaa                                 3150

SEQ ID NO: 68           moltype = AA  length = 1049
FEATURE                 Location/Qualifiers
REGION                  1..1049
                        note = synthetic P450-BM3 variant polypeptide
source                  1..1049
                        mol_type = protein
                        organism = synthetic construct
SEQUENCE: 68
MTIKEMPQPK TFGELKNLPL LNTDKPVQAL MKIADELGEI FKFEAPGCVT RYLSSQRLIK   60
EACDESRFDK NLSQALKFAR DFAGDGLVTS WTHEPNWKKA HNILLPSFSQ QAMKGYHAMM  120
VDIAVQLVQK WERLNADEHI EVSEDMTRLT LDTIGLCGFN YRFNSFYRDQ PHPFIVSMVR  180
ALDEVMNKLQ RANPDDPAYD ENKRQCQEDI KVMNDLVDKI IADRKARGEQ SHDLLTQMLN  240
GKDPETGEPL DDGNISYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN AGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
```

```
KQASITVSVV  SGEAWSGYGE  YKGIASNYLA  ELQEGDTITC  FISTPQSEFT  LPKDPETPLI   900
MVGPGTGVAP  FRGFVQARKQ  LKEQGQSLGE  AHLYFGCRSP  HEDYLYQEEL  ENAQSEGIIT   960
LHTAFSRMPN  QPKTYVQHVM  EQDGKKLIEL  LDQGAHFYIC  GDGSQMAPAV  EATLMKSYAD  1020
VHQVSEADAR  LWLQQLEEKG  RYAKDVWAG                                      1049
```

P450-BM3 VARIANTS WITH IMPROVED ACTIVITY

CROSS-REFERENCE TO RELATED APPLICATION

This application is a continuation of U.S. patent application Ser. No. 17/672,542 filed Feb. 15, 2022, now U.S. Pat. No. 11,807,874, which is a continuation of U.S. patent application Ser. No. 15/931,310, filed May 13, 2020, now U.S. Pat. No. 11,279,917 which is a continuation of U.S. patent application Ser. No. 16/131,252, filed Sep. 14, 2018, now U.S. Pat. No. 10,689,627, which is a continuation of US Pat. Appln. Ser. No. 15/619,176, filed Jun. 9, 2017, now U.S. Pat. No. 10,100,289, which is a Divisional of U.S. patent application Ser. No. 14/794,249, filed Jul. 8, 2015, now U.S. Pat. No. 9,708,587, which claims the benefit of U.S. Provisional Application Ser. No. 62/022,442, filed Jul. 9, 2014, the contents of each of which are incorporated herein by reference in their entireties and for all purposes.

FIELD OF THE INVENTION

The present invention provides improved P450-BM3 variants with improved activity. In some embodiments, the P450-BM3 variants exhibit improved activity over a wide range of substrates.

REFERENCE TO SEQUENCE LISTING, TABLE OR COMPUTER PROGRAM

The official copy of the Sequence Listing is submitted concurrently with the specification as an XML file, with a filename of "CX2_144USD1C4", a creation date of Sep. 25, 2023, and a size of 233,472 bytes. The ST26 Sequence Listing is part of the specification and is incorporated in its entirety by reference herein.

BACKGROUND OF THE INVENTION

The cytochrome P450 monooxgenases ("P450s") comprise a large group of widely-distributed heme enzymes that are ubiquitous in the natural world. Cytochrome P450-BM3 ("P450-BM3"), obtained from *Bacillus megaterium* catalyzes the NADPH-dependent hydroxylation of long-chain fatty acids, alcohols, and amides, as well as the epoxidation of unsaturated fatty acids (See e.g., Narhi and Fulco, J. Biol. Chem., 261:7160-7169 [1986]; and Capdevila et al., J. Biol. Chem., 271:2263-22671 [1996]). P450-BM3 is unique, in that the reductase (65 kDa) and monooxygenase (55 kDa) domains of the enzyme are fused and produced as a catalytically self-sufficient 120 kDa enzyme. Although these enzymes have been the subject of numerous studies, there remains a need in the art for improved P450s that exhibit high levels of enzymatic activity over a wide range of substrates.

SUMMARY OF THE INVENTION

The present invention provides improved P450-BM3 variants with improved activity. In some embodiments, the P450-BM3 variants exhibit improved activity over a wide range of substrates.

The present invention provides recombinant cytochrome P450-BM3 variants comprising the sequences set forth in SEQ ID NO:4, 6, 8, 10, 12, 14, 16, 18, 20, 22, 24, 26, 28, 30, 32, 34, 36, 38, 40, 44, 46, 48, 50, 52, 54, 56, 58, 60, 62, 64, 66, and 68. In some additional embodiments, the recombinant cytochrome P450-BM3 variant is set forth in SEQ ID NO:4, 6, 8, 10, 12, 14, 16, 18, 20, 22, 24, 26, 28, 30, 32, 34, 36, 38, 40, 44, 46, 48, 50, 52, 54, 56, 58, 60, 62, 64, 66, or 68. In some embodiments, the recombinant cytochrome P450-BM3 variant comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:4, 6, 8, 10, 12, 14, 16, 18, 20, 22, 24, 26, 28, 30, 32, 34, 36, 38, 40, 44, 46, 48, 50, 52, 54, 56, 58, 60, 62, 64, 66, and/or 68. In some embodiments, the recombinant cytochrome P450-BM3 variants oxidize at least three organic substrates. In some additional embodiments, the organic substrate is selected from nifedipine, propranolol, verapamil, diclofenac, and para-nitroanisol.

The present invention also provides isolated polynucleotide sequence encoding the recombinant cytochrome P450-BM3 variants. In some embodiments, the isolated polynucleotide sequence comprises SEQ ID NO:3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, or 67. In some additional embodiments, the isolated polynucleotide sequence is set forth in SEQ ID NO:3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, or 67. In some further embodiments, the isolated polynucleotide sequence comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, and/or 67.

The present invention also provides expression vectors comprising at least one polynucleotide sequence provided herein. In some additional embodiments, the vector comprises at least one polynucleotide sequence that is operably linked with at least one regulatory sequence suitable for expression of the polynucleotide sequence in a suitable host cell. In some embodiments, the host cell is a prokaryotic or eukaryotic cell. In some additional embodiments, the host cell is a prokaryotic cell. In some further embodiments, the host cell is *E. coli*. The present invention also provides host cells comprising the vectors provided herein.

The present invention also provides methods for producing at least one recombinant cytochrome P450-BM3 variant comprising culturing the host cell provided herein under conditions such that at least one of the recombinant cytochrome P450-BM3 variants provided herein is produced by the host cell. In some additional embodiments, the methods further comprise the step of recovering at least one recombinant cytochrome P450 variant.

DESCRIPTION OF THE INVENTION

Figure 1:
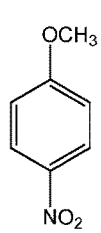
FIG. 1 provides the structures of the substrates used in the screening methods described herein. Diclofenac was used for HTP screening to detect/rank beneficial diversity. The remaining substrates were used to validate that the evolved BM3 variants were active on substrates that were not used for HTP screening.
Figure 1:
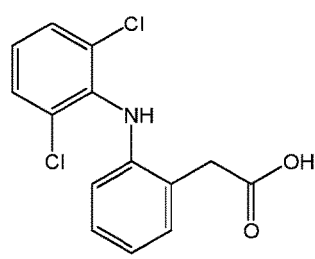
Figure 1:
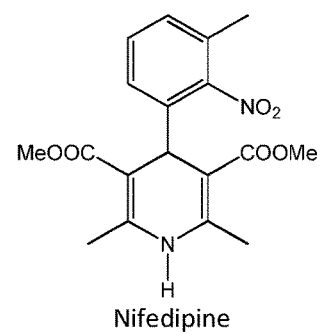
Figure 1:
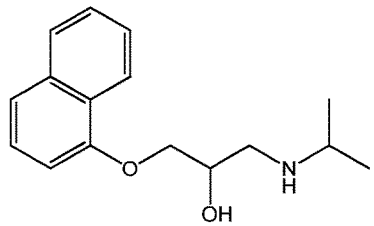
Figure 1:
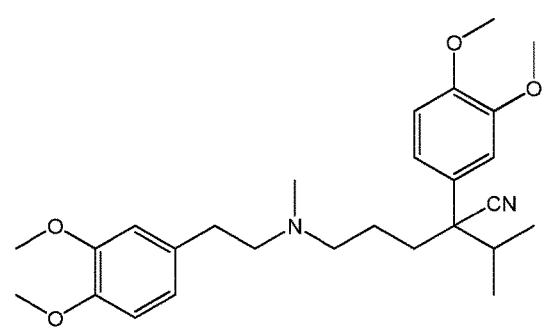

The present invention provides improved P450-BM3 variants with improved activity. In some embodiments, the P450-BM3 variants exhibit improved activity over a wide range of substrates. P450-BM3 enzymes exhibit the highest rate of catalysis amongst P450 monooxygenases due to the efficient electron transfer between the fused reductase and heme domains (See e.g., Noble et al., Biochem. J., 339:371-379 [1999]; and Munro et al., Eur. J. Biochem., 239:403-409 [2009]). Thus, P450-BM3 is a highly desirable enzyme for the manipulation of biotechnological processes (See e.g., Sawayama et al., Chem., 15:11723-11729 [2009]; Otey et al., Biotechnol. Bioeng., 93:494-499 [2006]; Damsten et al., Biol. Interact., 171:96-107 [2008]; and Di Nardo and Gilardi, Int. J. Mol. Sci., 13:15901-15924). However, there still remains a need in the art for P450 enzymes that exhibit activity over a broad range of substrates. The present invention provides P450-BM3 variants that have improved enzymatic activity over a broad range of substrates, as compared to a parental P450-BM3 sequence (i.e., SEQ ID NO:2).

In some embodiments, the present invention provides P450-BM3 variants that provide improved total percent conversion/turnover number for the oxidation of multiple organic substrates (e.g., diclofenac, para-nitroanisol, verpamil, nifedipine, and propranolol; See FIG. 1). In particular, during the development of the present invention, beneficial diversity was identified and recombined based on HTP screening results.

Abbreviations and Definitions

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances, "about" means within 0.05%, 0.5%, 1.0%, or 2.0%, of a given value range. In some instances, "about" means within 1, 2, 3, or 4 standard deviations of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein "cytochrome P450-BM3" and "P450-BM3" refer to the cytochrome P450 enzyme obtained from *Bacillus megaterium* that catalyzes the NADPH-dependent hydroxylation of long-chain fatty acids, alcohols, and amides, as well as the epoxidation of unsaturated fatty acids.

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The term "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example, a wild-type polypeptide or polynucleotide sequence is a sequence present in an organism that can be isolated from a source in nature and which has not been intentionally modified by human manipulation.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See, Altschul et al., J. Mol. Biol., 215: 403-410 [1990]; and Altschul et al., 1977, Nucl. Acids Res., 3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison WI), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. "Comparison window" refers to a conceptual segment of at least about 20 contiguous nucleotide positions or amino acid residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered P450-BM3, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X93 as compared to SEQ ID NO:2" refers to a difference of the amino acid residue at the polypeptide position corresponding to position 93 of SEQ ID NO:2. Thus, if the reference polypeptide of SEQ ID NO:2 has a serine at position 93, then a "residue difference at position X93 as compared to SEQ ID NO:2" an amino acid substitution of any residue other than serine at the position of the polypeptide corresponding to position 93 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in Table 2-1), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X307H/X307P or X307H/P). The present application includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered P450-BM3 enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

A "functional fragment" or a "biologically active fragment" used interchangeably herein refers to a polypeptide that has an amino-terminal and/or carboxy-terminal deletion(s) and/or internal deletions, but where the remaining amino acid sequence is identical to the corresponding positions in the sequence to which it is being compared (e.g., a full-length engineered P450-BM3 of the present invention) and that retains substantially all of the activity of the full-length polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The recombinant P450-BM3 polypeptides may be present within a cell, present in the cellular medium, or prepared in various forms, such as lysates or isolated preparations. As such, in some embodiments, the recombinant P450-BM3 polypeptides can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. However, in some embodiments, the composition comprising P450-BM3 comprises P450-BM3 that this less than 50% pure (e.g., about 10%, about 20%, about 30%, about 40%, or about 50%) Generally, a substantially pure P450-BM3 composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant P450-BM3 polypeptides are substantially pure polypeptide compositions.

"Improved enzyme property" refers to an engineered P450-BM3 polypeptide that exhibits an improvement in any enzyme property as compared to a reference P450-BM3 polypeptide and/or a wild-type P450-BM3 polypeptide or another engineered P450-BM3 polypeptide. Improved properties include but are not limited to such properties as increased protein expression, increased thermoactivity, increased thermostability, increased pH activity, increased stability, increased enzymatic activity, increased substrate specificity or affinity, increased specific activity, increased resistance to substrate or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, and altered temperature profile.

"Increased enzymatic activity" or "enhanced catalytic activity" refers to an improved property of the engineered P450-BM3 polypeptides, which can be represented by an increase in specific activity (e.g., product produced/time/weight protein) or an increase in percent conversion of the substrate to the product (e.g., percent conversion of starting amount of substrate to product in a specified time period using a specified amount of P450-BM3) as compared to the reference P450-BM3 enzyme. Exemplary methods to determine enzyme activity are provided in the Examples. Any property relating to enzyme activity may be affected, including the classical enzyme properties of $K_m$, $V_{max}$, or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring P450-BM3 or another engineered P450-BM3 from which the P450-BM3 polypeptides were derived.

"Conversion" refers to the enzymatic conversion (or biotransformation) of a substrate(s) to the corresponding product(s). "Percent conversion" refers to the percent of the substrate that is converted to the product within a period of time under specified conditions. Thus, the "enzymatic activity" or "activity" of a P450-BM3 polypeptide can be expressed as "percent conversion" of the substrate to the product in a specific period of time.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the P450-BM3 enzymes may be codon optimized for optimal production from the host organism selected for expression.

"Control sequence" refers herein to include all components, which are necessary or advantageous for the expression of a polynucleotide and/or polypeptide of the present application. Each control sequence may be native or foreign to the nucleic acid sequence encoding the polypeptide. Such control sequences include, but are not limited to, a leader, polyadenylation sequence, propeptide sequence, promoter sequence, signal peptide sequence, initiation sequence and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refers to those conditions in the enzymatic conversion reaction solution (e.g., ranges of enzyme loading, substrate loading, temperature, pH, buffers, co-solvents, etc.) under which a P450-BM3 polypeptide of the present application is capable of converting a substrate to the desired product compound, Exemplary "suitable reaction conditions" are provided in the present application and illustrated by the Examples. "Loading", such as in "compound loading" or "enzyme loading" refers to the concentration or amount of a component in a reaction mixture at the start of the reaction. "Substrate" in the context of an enzymatic conversion reaction process refers to the compound or molecule acted on by the P450-BM3 polypeptide. "Product" in the context of an enzymatic conversion process refers to the compound or molecule resulting from the action of the P450-BM3 polypeptide on a substrate.

As used herein the term "culturing" refers to the growing of a population of microbial cells under any suitable conditions (e.g., using a liquid, gel or solid medium).

Recombinant polypeptides can be produced using any suitable methods known in the art. Genes encoding the wild-type polypeptide of interest can be cloned in vectors, such as plasmids, and expressed in desired hosts, such as *E. coli*, etc. Variants of recombinant polypeptides can be generated by various methods known in the art. Indeed, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant P450-BM3 polypeptides" (also referred to herein as "engineered P450-BM3 polypeptides," "variant P450-BM3 enzymes," and "P450-BM3 variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., the polynucleotides encoding the P450-BM3 variants). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues means polypeptides that contain one or more non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

Engineered P450-BM3 Polypeptides:

In some embodiments, engineered P450-BM3 polypeptides are produced by cultivating a microorganism comprising at least one polynucleotide sequence encoding at least one engineered P450-BM3 polypeptide under conditions which are conducive for producing the engineered P450-BM3 polypeptide(s). In some embodiments, the engineered P450-BM3 polypeptide is recovered from the resulting culture medium and/or cells.

The present invention provides exemplary engineered P450-BM3 polypeptides having P450-BM3 activity. The Examples provide Tables showing sequence structural information correlating specific amino acid sequence features with the functional activity of the engineered P450-BM3 polypeptides. This structure-function correlation information is provided in the form of specific amino acid residues differences relative to a reference engineered polypeptide, as indicated in the Examples. The Examples further provide experimentally determined activity data for the exemplary engineered P450-BM3 polypeptides.

In some embodiments, the engineered P450-BM3 polypeptides of the invention having P450-BM3 activity comprise: a) an amino acid sequence having at least 85% sequence identity to reference sequence SEQ ID NO:2; b) an amino acid residue difference as compared to SEQ ID NO:2 at one or more amino acid positions; and c) which exhibits an improved property selected from i) enhanced catalytic activity, ii) reduced proteolytic sensitivity, iii) increased tolerance to acidic pH, iv) reduced aggregation, v) increased activity on a range of substrates (i.e., enzymes with a broad substrate range), or a combination of any of i), ii), iii) or iv), as compared to the reference sequence.

In some embodiments the engineered P450-BM3 which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:2, and an amino acid residue difference as compared to SEQ ID NO:2, at one or more amino acid positions (such as at 1, 2, 3, 4, 5, 6, 7, 8, 9, 10, 11, 12, 14, 15, 20 or more amino acid positions compared to SEQ ID NO:2, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2). In some embodiment the residue difference as compared to SEQ ID NO:2, at one or more positions will include at least 1, 2, 3, 4, 5, 6, 7, 8, 9, 10 or more conservative amino acid substitutions. In some embodiments, the engineered P450-BM3 polypeptide is a polypeptide listed in Table 2-1.

In some embodiments the engineered P450-BM3 which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:2

In some embodiments, the engineered P450-BM3 polypeptide comprises a functional fragment of an engineered P450-BM3 polypeptide encompassed by the invention. Functional fragments have at least 95%, 96%, 97%, 98%, or 99% of the activity of the engineered P450-BM3 polypeptide from which is was derived (i.e., the parent engineered P450-BM3). A functional fragment comprises at least 90%, 91%, 92%, 93%, 94%, 95%, 96%, 97%, 98% and even 99% of the parent sequence of the engineered P450-BM3. In some embodiments the functional fragment is truncated by less than 5, less than 10, less than 15, less than 10, less than 25, less than 30, less than 35, less than 40, less than 45, and less than 50 amino acids.

Variants with Improved Activity:

In some embodiments, the engineered P450-BM3 polypeptides of the invention having P450-BM3 activity comprise a) an amino acid sequence having at least 85% sequence identity to reference sequence SEQ ID NO:2, or a fragment thereof; b) an amino acid residue difference as compared to SEQ ID NO:2, at one or more amino acid positions; and c) which exhibits improved activity, as compared to SEQ ID NO:2.

In some embodiments, the engineered P450-BM3 that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2 and an amino acid residue difference as compared to SEQ ID NO:2, at one or more amino acid positions (such as at 1, 2, 3, 4, 5, 6, 7, 8, 9, 10, 11, 12, 14, 15, 20 or more amino acid positions compared to SEQ ID NO:2, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2.

In some embodiments, when all other assay conditions are essentially the same, the engineered P450-BM3 polypeptide has improved activity as compared to a reference P450-BM3 polypeptide. In some embodiments this activity can be measured under conditions that monitor enzymatic activity using any suitable assay system to assess the maximum activity of the enzyme (e.g., the $k_{cat}$). In other embodiments this activity can be measured under substrate concentrations resulting in one-half, one-fifth, one-tenth or less of maximal activity. Under either method of analysis, the engineered polypeptide has improved activity levels about 1.0 fold, 1.5-fold, 2-fold, 5-fold, 10-fold, 20-fold, 25-fold, 50-fold, 75-fold, 100-fold, or more of the enzymatic activity of the reference P450-BM3 In some embodiments, the engineered P450-BM3 polypeptide having improved activity as compared to a reference P450-BM3 when measured by any standard assay, including, but not limited to the assays described in the Examples.

In light of the guidance provided herein, it is further contemplated that any of the exemplary engineered polypeptides can be used as the starting amino acid sequence for synthesizing other engineered P450-BM3 polypeptides, for example by subsequent rounds of evolution by adding new combinations of various amino acid differences from other polypeptides and other residue positions described herein. Further improvements may be generated by including amino acid differences at residue positions that had been maintained as unchanged throughout earlier rounds of evolution.

Polynucleotides Encoding Engineered Polypeptides, Expression Vectors and Host Cells:

The present invention provides polynucleotides encoding the engineered P450-BM3 polypeptides described herein. In some embodiments, the polynucleotides are operatively linked to one or more heterologous regulatory sequences that control gene expression to create a recombinant polynucleotide capable of expressing the polypeptide. Expression constructs containing a heterologous polynucleotide encoding the engineered P450-BM3 polypeptides can be introduced into appropriate host cells to express the corresponding P450-BM3 polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the engineered P450-BM3 polypeptide. Thus, having knowledge of a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made encoding the polypeptides described herein by selecting combinations based on the possible codon choices, and all such variations are to be considered specifically disclosed for any polypeptide described herein, including the variants provided in Table 2-1, as well as SEQ ID NO:2.

In various embodiments, the codons are preferably selected to fit the host cell in which the protein is being produced. For example, preferred codons used in bacteria are used for expression in bacteria. Consequently, codon optimized polynucleotides encoding the engineered P450-BM3 polypeptides contain preferred codons at about 40%, 50%, 60%, 70%, 80%, or greater than 90% of codon positions of the full length coding region.

In some embodiments, as described above, the polynucleotide encodes an engineered polypeptide having P450-BM3 activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence (e.g., SEQ ID NO:2), or the amino acid sequence of any variant as disclosed in Table 2-1, and one or more residue differences as compared to the reference polypeptide of SEQ ID NO:2 or the amino acid sequence of any variant as disclosed in Table 2-1 (for example 1, 2, 3, 4, 5, 6, 7, 8, 9, 10 or more amino acid residue positions). In some embodiments, the reference sequence is selected from SEQ ID NO:2.

In some embodiments, the polynucleotides are capable of hybridizing under highly stringent conditions to a reference polynucleotide sequence selected from SEQ ID NO:1, or a complement thereof, or a polynucleotide sequence encoding any of the variant P450-BM3 polypeptides provided herein. In some embodiments, the polynucleotide capable of hybridizing under highly stringent conditions encodes a P450-BM3 polypeptide comprising an amino acid sequence that has one or more residue differences as compared to SEQ ID NO:2.

In some embodiments, an isolated polynucleotide encoding any of the engineered P450-BM3 polypeptides provided herein is manipulated in a variety of ways to provide for expression of the polypeptide. In some embodiments, the polynucleotides encoding the polypeptides are provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

In some embodiments, the control sequences include among other sequences, promoters, leader sequences, polyadenylation sequences, propeptide sequences, signal peptide sequences, and transcription terminators. As known in the art, suitable promoters can be selected based on the host cells used. For bacterial host cells, suitable promoters for directing transcription of the nucleic acid constructs of the present application, include, but are not limited to the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/ glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice finds use in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is a suitable leader sequence, a non-translated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are also known in the art (See e.g., Guo and Sherman, Mol. Cell. Bio., 15:5983-5990 [1995]).

In some embodiments, the control sequence is a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region that directs the expressed polypeptide into the secretory pathway of a host cell of choice finds use for expression of the engineered P450-BM3 polypeptides provided herein. Effective signal peptide coding regions for bacterial host cells include, but are not limited to the signal peptide coding regions obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is a propeptide coding region that codes for an amino acid sequence positioned at the amino terminus of a polypeptide. The resultant polypeptide is referred to as a "proenzyme," "propolypeptide," or "zymogen," in some cases). A propolypeptide can be converted to a mature active polypeptide by catalytic or autocatalytic cleavage of the propeptide from the propolypeptide. The propeptide coding region includes, but is not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention also provides a recombinant expression vector comprising a polynucleotide encoding an engineered P450-BM3 polypeptide, and one or more expression regulating regions such as a promoter and a terminator, a replication origin, etc., depending on the type of hosts into which they are to be introduced. in some embodiments, the various nucleic acid and control sequences described above are joined together to produce a recombinant expression vector which includes one or more convenient restriction sites to allow for insertion or substitution of the nucleic acid sequence encoding the variant P450-BM3 polypeptide at such sites. Alternatively, the polynucleotide sequence(s) of the present invention are expressed by inserting the polynucleotide sequence or a nucleic acid construct comprising the polynucleotide sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), that can be conveniently subjected to recombinant DNA procedures and can result in the expression of the variant P450-BM3 polynucleotide sequence. The choice of the vector will typically depend on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the expression vector preferably contains one or more selectable markers, which permit easy selection of transformed cells. A "selectable marker" is a gene the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In another aspect, the present invention provides a host cell comprising a polynucleotide encoding at least one engineered P450-BM3 polypeptide of the present application, the polynucleotide being operatively linked to one or more control sequences for expression of the engineered P450-BM3 enzyme(s) in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* and *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Exemplary host cells are *Escherichia coli* strains (such as W3110 (ΔfhuA) and BL21).

Accordingly, in another aspect, the present invention provides methods for producing the engineered P450-BM3 polypeptides, where the methods comprise culturing a host cell capable of expressing a polynucleotide encoding the engineered P450-BM3 polypeptide under conditions suitable for expression of the polypeptide. In some embodiments, the methods further comprise the steps of isolating and/or purifying the P450-BM3 polypeptides, as described herein.

Appropriate culture media and growth conditions for the above-described host cells are well known in the art. Polynucleotides for expression of the P450-BM3 polypeptides may be introduced into cells by various methods known in the art. Techniques include, among others, electroporation, biolistic particle bombardment, liposome mediated transfection, calcium chloride transfection, and protoplast fusion.

The engineered P450-BM3 with the properties disclosed herein can be obtained by subjecting the polynucleotide encoding the naturally occurring or engineered P450-BM3 polypeptide to mutagenesis and/or directed evolution methods known in the art, and as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,303,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254:157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; WO 2009/152336, and U.S. Pat. No. 6,537,746. all of which are incorporated herein by reference).

In some embodiments, the enzyme clones obtained following mutagenesis treatment are screened by subjecting the enzymes to a defined temperature (or other assay conditions, such as testing the enzyme's activity over a broad range of substrates) and measuring the amount of enzyme activity remaining after heat treatments or other assay conditions. Clones containing a polynucleotide encoding a P450-BM3 polypeptide are then sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tetra. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer), purified, annealed, ligated and cloned in appropriate vectors.

Accordingly, in some embodiments, a method for preparing the engineered P450-BM3 polypeptide can comprise: (a) synthesizing a polynucleotide encoding a polypeptide comprising an amino acid sequence selected from the amino acid sequence of any variant provided in Table 2-1, as well as SEQ ID NO:2, and (b) expressing the P450-BM3 polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered P450-BM3 polypeptide can be measured for any desired improved property (e.g., activity, selectivity, stability, acid tolerance, protease sensitivity, etc.), using any suitable assay known in the art, including but not limited to the assays and conditions described herein.

In some embodiments, any of the engineered P450-BM3 polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the P450-BM3 polypeptides include, among others, reverse phase chromatography high performance liquid chromatography, ion exchange chromatography, hydrophobic interaction chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved variant P450-BM3 enzymes. In some embodiments utilizing affinity chromatography purification, any antibody which specifically binds the variant P450-BM3 polypeptide finds use. For the production of antibodies, various host animals, including but not limited to rabbits, mice, rats, etc., are immunized by injection with a P450-BM3 polypeptide (e.g., a P450-BM3 variant), or a fragment thereof. In some embodiments, the P450-BM3 polypeptide or fragment is attached to a suitable carrier, such as BSA, by means of a side chain functional group or linkers attached to a side chain functional group.

In some embodiments, the engineered P450-BM3 polypeptide is produced in a host cell by a method comprising culturing a host cell (e.g., an E. coli strain) comprising a polynucleotide sequence encoding an engineered P450-BM3 polypeptide as described herein under conditions conducive to the production of the engineered P450-BM3 polypeptide and recovering the engineered P450-BM3 polypeptide from the cells and/or culture medium.

In some embodiments, the engineered P450-BM3 polypeptides are recovered from the recombinant host cells or cell culture and they are further purified by any suitable method(s) known in the art. In some additional embodiments, the purified P450-BM3 polypeptides are combined with other ingredients and compounds to provide compositions and formulations comprising the engineered P450-BM3 polypeptide as appropriate for different applications and uses (e.g., pharmaceutical compositions).

The foregoing and other aspects of the invention may be better understood in connection with the following non-limiting examples. The examples are provided for illustrative purposes only and are not intended to limit the scope of the present invention in any way.

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); CDS (coding sequence); DNA (deoxyribonucleic acid); RNA (ribonucleic acid); NA (nucleic acid; polynucleotide); AA (amino acid; polypeptide); E. coli W3110 (commonly used laboratory E. coli strain, available from the Coli Genetic Stock Center [CGSC], New Haven, CT); HPLC (high pressure liquid chromatography); SDS-PAGE (sodium dodecyl sulfate polyacrylamide gel electrophoresis); PES (polyethersulfone); CFSE (carboxyfluorescein succinimidyl ester); IPTG (isopropyl beta-D-1-thiogalactopyranoside); PMBS (polymyxin B sulfate); NADPH (nicotinamide adenine dinucleotide phosphate); GDH (glucose dehydrogenase); FIOPC (fold improvement over positive control); ESI (electrospray ionization); LB (Luria broth); TB (terrific broth); MeOH (methanol); Athens Research (Athens Research Technology, Athens, GA); ProSpec (ProSpec Tany Technogene, East Brunswick, NJ); Sigma-Aldrich (Sigma-Aldrich, St. Louis, MO); Ram Scientific (Ram Scientific, Inc., Yonkers, NY); Pall Corp. (Pall, Corp., Pt. Washington, NY); Millipore (Millipore, Corp., Billerica MA); Difco (Difco Laboratories, BD Diagnostic Systems, Detroit, MI); Molecular Devices (Molecular Devices, LLC, Sunnyvale, CA); Kuhner (Adolf Kuhner, AG, Basel, Switzerland); Cambridge Isotope Laboratories, (Cambridge Isotope Laboratories, Inc., Tewksbury, MA); Applied Biosystems (Applied Biosystems, part of Life Technologies, Corp., Grand Island, NY), Agilent (Agilent Technologies, Inc., Santa Clara, CA); Thermo Scientific (part of Thermo Fisher Scientific, Waltham, MA); Fisher (Fisher Scientific, Waltham, MA); Corning (Corning, Inc., Palo Alto, CA); Waters (Waters Corp., Milford, MA); GE Healthcare (GE Healthcare Bio-Sciences, Piscataway, NJ); Pierce (Pierce Biotechnology (now part of Thermo Fisher Scientific), Rockford, IL); Phenomenex (Phenomenex, Inc., Torrance, CA); Optimal (Optimal Biotech Group, Belmont, CA); and Bio-Rad (Bio-Rad Laboratories, Hercules, CA).

Example 1

P450-BM3 Gene Acquisition and Construction of Expression Vectors

Libraries of P450-BM3 variants were produced using standard methods known in the art, based on the parental sequence of SEQ ID NO:2 (SEQ ID NO:1 is the corresponding polynucleotide sequence) and SEQ ID NO:42 (SEQ ID NO:41 is the corresponding polynucleotide sequence). These variants, cloned into an IPTG-inducible vector were transformed into E. coli BL21 strain and plated on LB agar plates supplemented with chloramphenicol (30 μg/mL). The plates were grown at 37° C. for 16 hrs before single clones were picked and added to 96-well AXYGEN® plates (Corning), containing LB medium (250 μL/well) supplemented with chloramphenicol (30 μg/mL). After the plates were shaken at 250 rpm, 30° C., and 85% humidity for 20-24 h to grow the cultures to saturation, an aliquot (50 μL) was used to inoculate 2 mL 96-well COSTAR® deep plates (Corning) containing TB medium (900 μL) supplemented with chloramphenicol (30 μg/mL), trace element solution (740 ug/L ammonium molybdate tetrahydrate, 5.8 mgs/L zinc sulfate heptahydrate, 620 ug/L boric acid anhydrous, 1 mg/L copper sulfate pentahydrate, and 4 mgs/L manganese chloride tetrahydrate), and 0.05 g/L ammonium iron (III) citrate. After being shaken at 250 rpm, 30° C., and 85% humidity to an $OD_{600}$ of 0.8-1.2, P450 expression was induced by addition of IPTG (500 uM) and the heme precursor 5-aminolevulinic acid (5-ALA) to a final concentration of 500 uM. The cultures were shaken at 250 rpm, 26° C., 85% humidity for 24 hrs before the cells were centrifuged and stored at −80° C.

Cell lysis was accomplished by resuspending cell pellets in 96-well COSTAR® plates (Corning) with lysis buffer (200-300 µL/well) containing potassium phosphate, pH 8.0 (100 mM), MgSO$_4$ (10 mM), DTT (1 mM), lysozyme (1 mg/mL), PMBS (0.5 mg/mL), and DNAseI (3 µgs/mL). The lysis reactions were shaken using a Thermo Scientific titer shaker (model 4625 and setting 8-10) at room temperature for 1-2 hrs. The lysis reaction was centrifuged to pellet cellular debris and the supernatant was used in the activity assays described in Example 2.

For the production of lyophilized protein powders, LB agar plates supplemented with chloramphenicol (30 µg/mL) were streaked with E. coli containing a desired B. megaterium P450-BM3 variant in the IPTG-inducible pCK200 vector. The plates were grown at 37° C. for 16 hrs before single clones were selected to inoculate a 15 mL FALCON™ tube (Fisher) containing TB media (3 mL) supplemented with chloramphenicol (30 µg/mL). The tube was shaken at 200 rpm, 30° C., and 85% humidity for 20-24 h to grow the cultures to saturation. Then, 2.5 mL of the overnight culture was used to inoculate sterile 1 L flasks containing TB medium (250 mL) supplemented with chloramphenicol (30 µg/mL), trace element solution (as indicated above), and 0.05 g/L ammonium iron (III) citrate. After being shaken at 250 rpm, 30° C., and 85% humidity to an OD$_{600}$ of 0.8-1.2, P450 expression was induced by addition of IPTG (500 uM) and the heme precursor 5-aminolevulinic acid (5-ALA) to a final concentration of 500 uM. The cultures were centrifuged in pre-weighed 250 mL centrifuge bottles for 20 minutes at 4000 rpm, 4° C. The supernatants were discarded, and the centrifuge bottles containing cell pellets were weighed. The pellets were resuspended in 50 mM potassium phosphate buffer with 2 mM DTT, pH 8.0 (5 mL of buffer per gram of cell pellet). The cells were lysed using a microfluidics homogenizer, and the suspension of cells and lysate was collected in sterile 50 mL centrifuge tubes. The samples were centrifuged for 30 minutes at 10,000 rpm, 4° C. The clarified lysate was collected into a plastic petri plate and frozen at −80° C. prior to lyophilization. The enzyme-containing lysates were lyophilized using standard methods known in the art.

Example 2

Assay Systems & Results

In this Example, the test systems used to assess the activities and generalist properties (i.e., activity on a broad substrate range) are described.

I. Activity-Based High Throughput Screening (HTP) for Enzymatic Activity:

Diclofenac (See, FIG. 1) was used as a substrate for high throughput (HTP) screening assays to detect variants with improved activity. Enzymatic activity screens were initiated by adding 60 µL lysate and 120 µL of the reaction mixture to each well of a 96-well (2 mL) plate. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (3 mM diclofenac). The reactions were shaken at 250 rpm, 30° C., 85% humidity for 4-24 hrs. The reactions were quenched by the addition of acetonitrile (400 µL to 1 ml) to each well. The quenched reactions were centrifuged to remove precipitated proteins prior to analysis with HPLC and LCMS, as described below.

II. Validation of Generalist Properties:

Lyophilized powders produced as described in Example 1, were dissolved in 100 mM potassium phosphate buffer, pH 7.5 (~12 mgs/mL), and the UV-visible absorption spectrum of each variant was determined. The stock solution of each variant was normalized to ~6 µM. In a 96-well (2 mL) plate, enzymatic activity screens were initiated by adding 50 µL of each lyophilized powder solution (1 µM final) and 250 µL of the reaction mixture to each well. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (0.6-3 mM). Lyophilized protein powders were first validated using diclofenac to confirm the observations in HTP. Nifedipine, verapamil, and propranolol were selected as substrates to confirm that the BM3 mutants evolved for generalist properties (i.e., broad substrate range) were improved for substrates not used for HTP screening to identify beneficial diversity. The reactions were shaken at 250 rpm, 30° C., 85% humidity for 18 hrs. The reactions were quenched by the addition of acetonitrile (400-1000 µL) to each well. The quenched reactions were centrifuged to remove precipitated proteins prior to analysis with HPLC and LCMS, as described below.

III. HPLC and LCMS Analysis:

For analysis, 150 µL of the quenched reaction sample to be assessed were transferred to 96-well round bottom plates for analysis by HPLC on an Agilent 1200 series equipped with an autosampler. Then, a 10 µL aliquot of the quenched sample was injected onto an ONYX™ Monolithic C18 column (2×50 mm) (Phenomenex). The column was eluted at a constant flow rate of 0.5 mL/min; conditions with solvent A (0.1% formic acid v/v, in H$_2$O) and solvent B (0.1% formic acid v/v, in acetonitrile) used to elute the products of the reaction were: 0-1 min, A/B 90:10; 1-2 min, A/B 80:20; 2-4 min, A/B 70:30; 4-4.5 min, A/B 60:40; 4.5-4.9 min, A/B 10:90, and 4.9-5.3 min, A/B 90:10. The column eluent was monitored by UV at 270 nm.

Alternatively, analysis by LC-UV-MS was performed for some substrates on a Thermo LXQ ion trap system using a SURVEYOR PLUS™ LC-PDA (Thermo Scientific) system for sample separation. For this analysis 0.01 mL of quenched sample was injected into an XBRIDGE® C18 column (3×50 mm, 5µ) (Waters). The column was eluted at a constant flow rate of 0.5 mL/min; the conditions with solvent A (0.1% formic acid v/v, in H2O) and solvent B (0.1% formic acid v/v, in acetonitrile) used to elute the products of the reaction were: 0-1.5 min, A/B 90:10; 1.5-5.5 min, A/B 20:80; 5.5-6.0 min, A/B 1:99; 6.0-6.25 min, A/B 90:10; 6.25-7.5 min, A/B 90:10. Column eluent was monitored by PDA (200-600 nm) prior to MS analysis in positive ESI mode (capillary temperature 350° C., 5 kV spray voltage). The column eluent was diverted to waste for the first 1.5 minutes of the run. For the remainder of the LC run, both MS (m/z 125-1000 scan range) and MS/MS were collected. MS/MS spectra were acquired in a data-dependent manner for the nth most intense ions employing dynamic exclusion for dominate ions after the 5th occurrence with an exclusion duration of 30 seconds. The data were analyzed using XCALIBUR™ software (Thermo Scientific) for substrate and product base peaks and MS/MS transitions.

Figure 2:
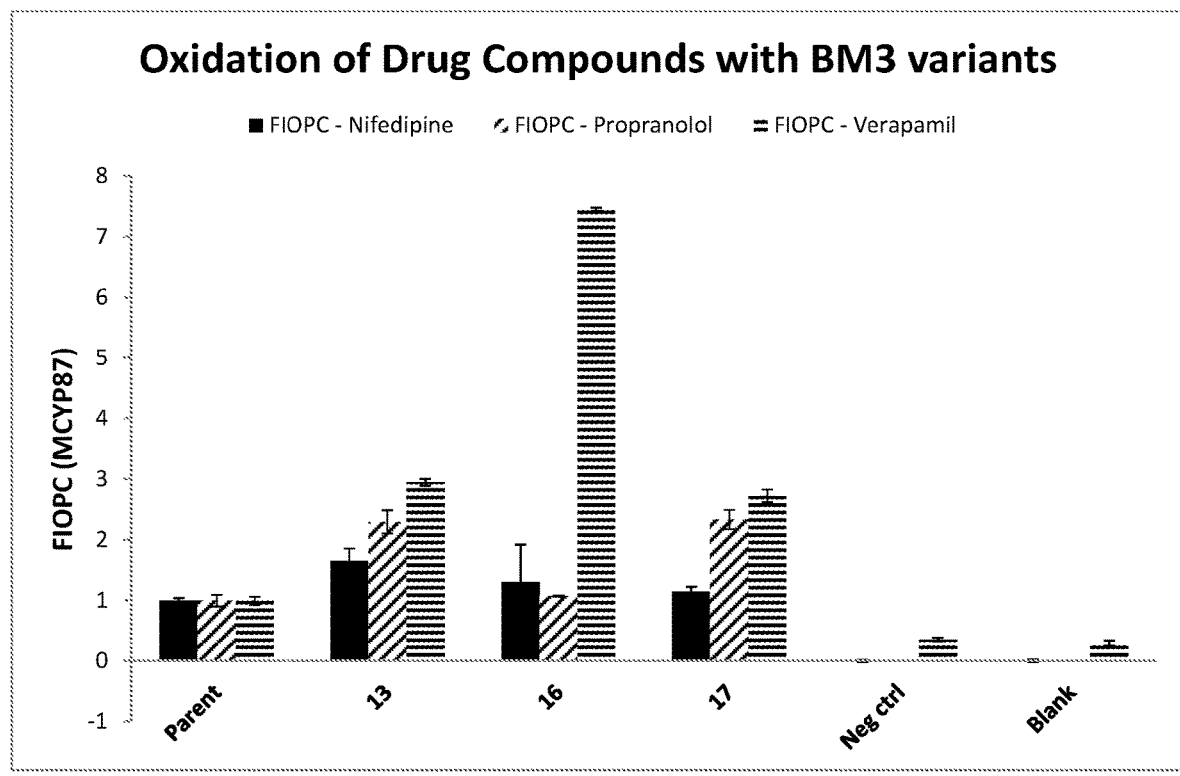
FIG. 2 provides a graph showing the performance of three BM3 variants and the positive control (i.e., the parental BM3 sequence; SEQ ID NO:2) on nifedipine, propranolol and verapamil.

IV. Results:

Variants of P450-BM3 were identified that improve the total % conversion/turnover number for the oxidation of multiple organic substrates (diclofenac, nifedipine, propranolol, and verapamil; See, FIG. 2). In FIG. 2, the fold improvement over positive control (FIOPC; positive control: SEQ ID NOS: 1/2) is plotted as a function of each enzyme's performance using nifedipine, propranolol, and verapamil as substrates. During the development of the present invention, beneficial diversity was identified and recombined as a result of HTP screening using diclofenac or p-nitroanisole as the substrate. Subsequently, lyophilized powders of the best performing BM3 variants were generated and validated using diclofenac as the substrate (enzyme samples were normalized to 1 µM). The results are provided in Table 2-1, below. For variants 1-16, the FIOPC is calculated using MCYP87 as the positive control/parental gene (SEQ ID NOS: 1/2). The FIOPC for variant 17 (SEQ ID NO: 35/36) is calculated using variant 13 (SEQ ID NOS: 15/16) as the positive control/parental gene. The FIOPC for variants 18 and 19 (SEQ ID NOS: 37/38 and 39/40) is calculated using variant 17 (SEQ ID NOS: 35/36) as the positive control/parental gene. Then, a subset of these variants (variants 13, 16, and 17; SEQ ID NOS: 15/16, 33/34, and 35/36) were screened against additional substrates (i.e., substrates that were not used to rank diversity) to determine their performance when screened against additional substrates (FIG. 2).

In Table 2-1, the results are shown based on the following:

TABLE 2-1

| % Conversion | Notation | FIOPC | Notation |
|---|---|---|---|
| 5-10 | + | 0.7-1.0 | * |
| 10.01-15 | ++ | 1.01-1.50 | ** |
| 15.01-20 | +++ | 1.51-2.0 | *** |
| 20.01-25 | ++++ | 2.01-2.5 | **** |
| 25.01-30 | +++++ | 2.51-3.0 | ***** |
| >30 | ++++++ | >3.0 | ****** |

Results for P450-BM3 Variants

| Substrate-Conc. | Variant # | % Conv. | FIOPC | Mutations (Compared to SEQ ID NO: 2); SEQ ID NOS: (NA/AA) |
|---|---|---|---|---|
| Diclofenac-1 mM | 1 | +++++ | **** | K32R; I95P; G115R; D232H; E349H (SEQ ID NOS: 5/6) |
| Diclofenac-1 mM | 2 | ++++ | *** | I95P; L105G; D232H; S724P; A1009T (SEQ ID NOS: 13/14) |
| Diclofenac-1 mM | 3 | ++++ | **** | L105A; Q110H; K114I; L216Y; Y346W; E349R; Q547N; T613R; L729V (SEQ ID NOS: 21/22) |
| Diclofenac-1 mM | 4 | ++++ | *** | L105A; Q110H; Y346W; T577H; T613R; L729V (SEQ ID NOS: 23/24) |
| Diclofenac-1 mM | 5 | +++ | ** | I176Q; D218Q; P347Q; E349S; G458F; D550R; T577P; D600R (SEQ ID NOS: 25/26) |
| Diclofenac-1 mM | 6 | + | * | P347Q; E349S; G458F; D550R; K771T; A1027Y (SEQ ID NOS: 27/28) |
| Diclofenac-1 mM | 7 | ++++ | *** | I176V; S231R; E349A; T577A; T613N; D722G; L795M; D992G; A1048M (SEQ ID NOS: 29/30) |
| Diclofenac-1 mM | 8 | ++++ | **** | S231R; D433K; T613N; A1048M (SEQ ID NOS: 31/32) |
| Diclofenac-1 mM | 9 | +++++ | **** | K32R; I95P; L105G; A198R; D232H; D433V; T577G; N597L; T613P; L795S; A1009T (SEQ ID NOS: 7/8) |
| Diclofenac-1 mM | 10 | ++++ | ++++ | I95P; D232H; L795S (SEQ ID NOS: 9/10) |
| Diclofenac-1 mM | 11 | +++ | *** | I95P; L105G; G115R; D232H; T577G; N597L; T613P; S724P (SEQ ID NOS: 3/4) |
| Diclofenac-1 mM | 12 | ++ | ** | K32R; I95P; A198R; D232H; S724P; A1009T (SEQ ID NOS: 11/12) |
| Diclofenac-1 mM | 13 | +++++ | ***** | K32R; G115R; D232H (SEQ ID NOS: 15/16) |
| Diclofenac-1 mM | 14 | +++ | **** | I95P; L105G; A198R; Q547G; T577G; N597L; S724P (SEQ ID NOS: 17/18) |
| Diclofenac-1 mM | 15 | +++++ | ****** | K32R; I95P; L105G; D232H; D433V; T577G; N597L; K791H (SEQ ID NOS: 19/20) |
| Diclofenac-1 mM | 16 | ++++++ | ****** | Y52F; L216Y; K219R; D433R; E616V (SEQ ID NOS: 33/34) |
| Diclofenac-2 mM | 17 | ++++ | *** | K32R; I95P; G115R; I176V; D232H; M491A (SEQ ID NOS: 35/36) |

TABLE 2-1-continued

| | | | | |
|---|---|---|---|---|
| Diclofenac-2 mM | 18 | +++++ | ** | K32R; L48S; Y52F; I95P; G115R; I176V; L216Y; D232H; E349K; M491A; N574T; T577A; E619D (SEQ ID NOS: 37/38) |
| Diclofenac-2 mM | 19 | +++++ | ** | K32R; L48S; I95P; G115R; I176V; D232H; E349K; K453G; M491A; T577A; E619D (SEQ ID NOS: 39/40) |

Example 3

Assay Systems & Results

In this Example, the test systems used to assess the activities and generalist properties (i.e., activity on a broad substrate range) transferred to a parental backbone differing by at least 7 mutations compared to the parental gene defined in Example 2 are described.

I. Activity-Based High Throughput Screening (HTP) for Enzymatic Activity:

Diclofenac (See, FIG. 1) was used as a substrate for high throughput (HTP) screening assays to detect variants with improved activity. Enzymatic activity screens were initiated by adding 60 µL lysate and 120 µL of the reaction mixture to each well of a 96-well (2 mL) plate. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (3 mM diclofenac). The reactions were shaken at 250 rpm, 30° C., 85% humidity for 4-24 hrs. The reactions were quenched by the addition of acetonitrile (400 µL to 1 ml) to each well. The quenched reactions were centrifuged to remove precipitated proteins prior to analysis with HPLC and LCMS, as described below.

II. Validation of Generalist Properties:

Lyophilized powders produced as described in Example 1 were dissolved in 100 mM potassium phosphate buffer, pH 7.5 (~12 mg/mL), and the UV-visible absorption spectrum of each variant was determined. The stock solution of each variant was normalized to ~6 µM. In a 96-well (2 mL) plate, enzymatic activity screens were initiated by adding 50 µL of each lyophilized powder solution (1 µM final) and 250 µL of the reaction mixture to each well. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (0.6-3 mM). Lyophilized protein powders were first validated using diclofenac to confirm the observations in HTP. Nifedipine, verapamil, and propranolol were selected as substrates to confirm that the beneficial diversity for generalist properties (i.e., applicable to a broad substrate range) transferred to a different parental backbone retained the property of being improved on substrates not used for HTP screening. The reactions were shaken at 250 rpm, 30° C., 85% humidity for 18 hrs. The reactions were quenched by the addition of acetonitrile (400-1000 µL) to each well. The quenched reactions were centrifuged to remove precipitated proteins prior to analysis with HPLC and LCMS, as described below.

III. HPLC and LCMS Analysis:

For analysis, 150 µL of the quenched reaction sample to be assessed were transferred to 96-well round bottom plates for analysis by HPLC on an Agilent 1200 series equipped with an autosampler. Then, a 10 µL aliquot of the quenched sample was injected onto an ONYX™ Monolithic C18 column (2×50 mm) (Phenomenex). The column was eluted at a constant flow rate of 0.5 mL/min; conditions with solvent A (0.1% formic acid v/v, in $H_2O$) and solvent B (0.1% formic acid v/v, in acetonitrile) used to elute the products of the reaction were: 0-1 min, A/B 90:10; 1-2 min, A/B 80:20; 2-4 min, A/B 70:30; 4-4.5 min, A/B 60:40; 4.5-4.9 min, A/B 10:90, and 4.9-5.3 min, A/B 90:10. The column eluent was monitored by UV at 270 nm.

Alternatively, analysis by LC-UV-MS was performed for some substrates on a Thermo LXQ ion trap system using a SURVEYOR PLUS™ LC-PDA (Thermo Scientific) system for sample separation. For this analysis 0.01 mL of quenched sample was injected into an XBRIDGE® C18 column (3×50 mm, 5µ) (Waters). The column was eluted at a constant flow rate of 0.5 mL/min; the conditions with solvent A (0.1% formic acid v/v, in $H_2O$) and solvent B (0.1% formic acid v/v, in acetonitrile) used to elute the products of the reaction were: 0-1.5 min, A/B 90:10; 1.5-5.5 min, A/B 20:80; 5.5-6.0 min, A/B 1:99; 6.0-6.25 min, A/B 90:10; 6.25-7.5 min, A/B 90:10. Column eluent was monitored by PDA (200-600 nm) prior to MS analysis in positive ESI mode (capillary temperature 350° C., 5 kV spray voltage). The column eluent was diverted to waste for the first 1.5 minutes of the run. For the remainder of the LC run, both MS (m/z 125-1000 scan range) and MS/MS were collected. MS/MS spectra were acquired in a data-dependent manner for the nth most intense ions employing dynamic exclusion for dominate ions after the $5^{th}$ occurrence with an exclusion duration of 30 seconds. The data were analyzed using X™ software (Thermo Scientific) for substrate and product base peaks and MS/MS transitions.

IV. Results:

Diversity beneficial for broadening the substrate scope was previously identified over several rounds of evolution leading to the variant MCYP87 (SEQ ID NO:2). Six beneficial mutations were identified and combinations of these mutations were transferred to MCYP P-1.2-A07 (SEQ ID NO: 42) as the parental gene. MCYP P-1.2-A07 differs from MCYP87 by seven mutations, including mutations in the active site and substrate channel that have a significant impact on substrate recognition. The ability to transfer diversity to a different yet related backbone is significant owing to the fact that the identification of beneficial diversity is often rather specific to the reference backbone. The demonstration of transferrable beneficial diversity is important as initial improvements may be manifest without the requirement of initial directed evolution-based HTP screening.

Figure 3:
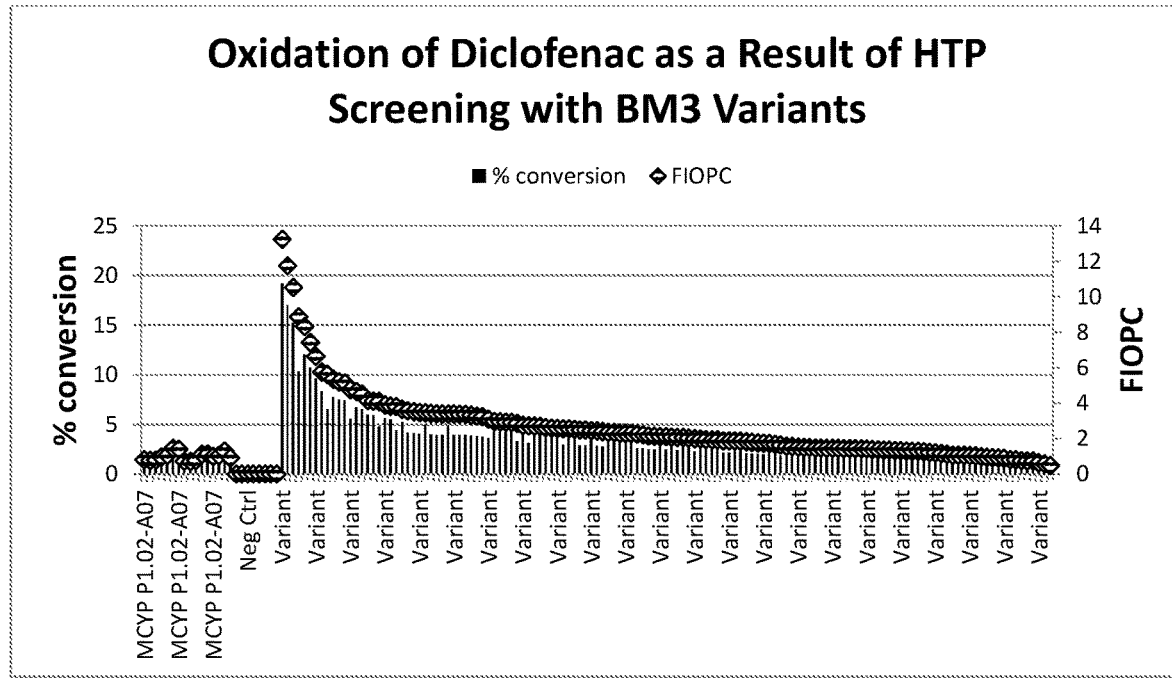
FIG. 3 provides a graph showing the HTP performance of 135 BM3 variants, the negative control (pCK200 vector only), and the positive control (i.e., the parental BM3 sequence; SEQ ID NO:42) on diclofenac.
Figure 4:
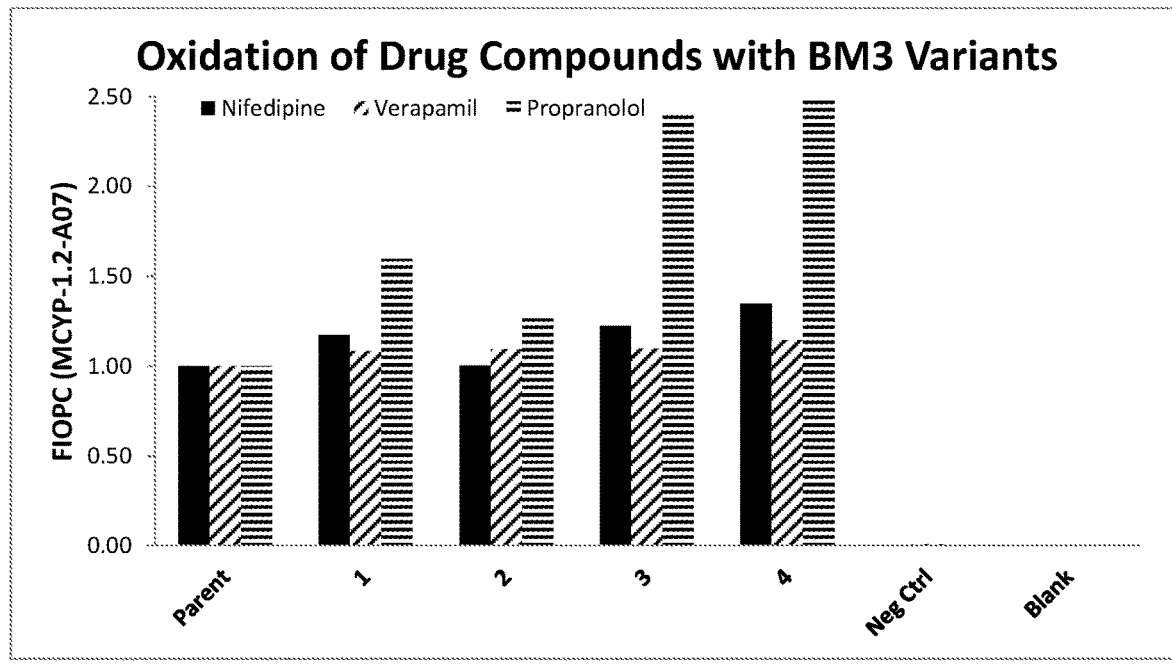
FIG. 4 provides a graph showing the performance of four BM3 variants and the positive control (i.e., the parental BM3 sequence; SEQ ID NO:42) on nifedipine, propranolol and verapamil.

HTP screening of variants of MCYP P1.2-A07 (i.e., SEQ ID NO: 42) was completed using diclofenac as the substrate to test the transferability of the diversity (See, FIG. 1 and FIG. 3). The results are provided in Table 3-1, below. The FIOPC in table 3-1 were calculated using MCYP-1.2-A07 (SEQ ID NOS: 41/42) as the positive control. Then, lyophilized protein powders for a subset of these variants (variants 1, 2, 3, and 4; SEQ ID NOS: 43/44, 45/46, 47/48, and 49/50) were generated and screened against multiple organic substrates (nifedipine, propranolol, and verapamil; See, FIG. 4). These variants of P450-BM3 retain their ability to improve the total % conversion/turnover number for the oxidation of the substrates evaluated. In FIG. 4, the fold improvement over positive control (FIOPC, as compared to MCYP P1.2-A07 [SEQ ID NO:42]) is plotted as a function of each enzyme's performance using nifedipine, propranolol, and verapamil as substrates.

In Table 3-1, the results are shown based on the following:

TABLE 3-1

| % Conversion | Notation | FIOPC | Notation |
|---|---|---|---|
| 0-5.00 | + | 1.0-3.0 | * |
| 5.01-10.00 | ++ | 3.01-5.0 | ** |
| 10.01-15.00 | +++ | 5.01-10.0 | *** |
| 15.01-20.00 | ++++ | 10.01-15.00 | **** |

| Results for P450-BM3 Variants | | | | |
|---|---|---|---|---|
| Substrate-Conc. | Variant # | % Conv. | FIOPC | Mutations (Compared to SEQ ID NO: 42)[a] |
| Diclofenac-2 mM | [b]1 | ++++ | **** | I95P; G115R; I176V; D232H (SEQ ID NOS: 43/44) |
| Diclofenac-2 mM | [b]2 | ++++ | *** | K32R; I95P; G115R; I176V; M491A (SEQ ID NOS: 45/46) |
| Diclofenac-2 mM | [b]3 | ++++ | **** | I95P; G115R; M491A (SEQ ID NOS: 47/48) |
| Diclofenac-2 mM | [b]4 | ++++ | *** | I95P; G115R; I176V; D232H; M491A (SEQ ID NOS: 49/50) |
| Diclofenac-2 mM | 5 | + | * | K32R; G115R; D232H; M491A (SEQ ID NOS: 51/52) |
| Diclofenac-2 mM | 6 | + | * | K32R; G115R; M491A (SEQ ID NOS: 53/54) |
| Diclofenac-2 mM | 7 | + | * | K32R; I95P; G115R; D232H; M491A (SEQ ID NOS: 55/56) |
| Diclofenac-2 mM | 8 | ++++ | *** | K32R; I95P; G115R; I176V; D232H; M491A (SEQ ID NOS: 57/58) |
| Diclofenac-2 mM | 9 | + | * | G115R; I176V; D232H; M491A (SEQ ID NOS: 59/60) |
| Diclofenac-2 mM | 10 | + | * | I176V; M491A; (SEQ ID NOS: 61/62) |
| Diclofenac-2 mM | 11 | + | ** | I95P; G115R; D232H (SEQ ID NOS: 63/64) |
| Diclofenac-2 mM | 12 | ++ | ** | I95P; G115R; I176V; D232H; T516P (SEQ ID NOS: 65/66) |
| Diclofenac-2 mM | 13 | + | * | I95P; I176V; D232H; M491A (SEQ ID NOS: 67/68) |

[a]Sequence ID NO: 42 corresponds to MCYP-1.2-A07.
[b]Shake flask powders validated.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

What is claimed is:

1. A recombinant cytochrome P450-BM3 variant comprising the amino acid sequence of SEQ ID NO: 34.

2. The recombinant cytochrome P450-BM3 variant of claim 1, wherein said variant oxidizes at least three organic substrates.

3. The recombinant cytochrome P450-BM3 variant of claim 2, wherein the at least three organic substrates are selected from the group consisting of nifedipine, propranolol, verapamil, and diclofenac.

4. An isolated polynucleotide comprising a nucleotide sequence encoding the recombinant cytochrome P450-BM3 variant of claim 1.

5. The isolated polynucleotide of claim 4, wherein said nucleotide sequence comprises the nucleotide sequence of SEQ ID NO: 33.

6. An expression vector comprising the polynucleotide of claim 4.

7. The expression vector of claim 6, wherein said polynucleotide is operably linked with regulatory sequences for expression of said polynucleotide in a host cell.

8. The expression vector of claim 7, wherein said host cell is a prokaryotic or eukaryotic cell.

9. The expression vector of claim 8, wherein said host cell is a prokaryotic cell.

10. The expression vector of claim 8, wherein said host cell is *E. coli*.

11. A host cell comprising the expression vector of claim 6.

12. A method for producing at least one recombinant cytochrome P450-BM3 variant comprising culturing the host cell of claim 11 under conditions such that the at least one recombinant cytochrome P450-BM3 variant is produced.

13. The method of claim 12, further comprising the step of recovering said at least one recombinant cytochrome P450-BM3 variant.

* * * * *